US010370423B2

(12) United States Patent
Sahin et al.

(10) Patent No.: US 10,370,423 B2
(45) Date of Patent: Aug. 6, 2019

(54) CLAUDIN-6-SPECIFIC IMMUNORECEPTORS AND T CELL EPITOPES

(71) Applicants: BioNTech Cell & Gene Therapies GmbH, Mainz (DE); TRON-Translationale Onkologie an der Universitätsmedizin der Johannes Gutenberg-Universität Mainz gemeinnützige GmbH, Mainz (DE); Universitätsmedizin der Johannes Gutenberg-Universität Mainz, Mainz (DE); Ganymed Pharmaceuticals AG, Mainz (DE)

(72) Inventors: Ugur Sahin, Mainz (DE); Özlem Türeci, Mainz (DE); Petra Simon, Mainz (DE); Tana Omokoko, Mainz (DE); Holger Hoff, Mainz (DE); Ralf-Holger Voss, Ingelheim (DE); Andrea Breitkreuz, Worms (DE); Kathleen Hobohm, Kelkheim i. Ts (DE); Karolina Anna Mroz, Wiesbaden (DE)

(73) Assignees: Biotech Cell & Gene thrapies GMBH, Mainz (DE); Tron—Translationale Onkologie Ander Universitata tsmedizin Der Johannes Gutenberg-Universitat Main, Mainz (DE); Ganymed Pharmceuticals AG, Mainz (DE)

( * ) Notice: Subject to any disclaimer, the term of this patent is extended or adjusted under 35 U.S.C. 154(b) by 169 days.

(21) Appl. No.: 15/124,640

(22) PCT Filed: Mar. 30, 2015

(86) PCT No.: PCT/EP2015/056899
§ 371 (c)(1),
(2) Date: Sep. 8, 2016

(87) PCT Pub. No.: WO2015/150327
PCT Pub. Date: Oct. 8, 2015

(65) Prior Publication Data
US 2017/0015720 A1  Jan. 19, 2017

(30) Foreign Application Priority Data

Apr. 1, 2014  (WO) .................. PCT/EP2014/000868
Oct. 24, 2014  (WO) .................. PCT/EP2014/072864

(51) Int. Cl.
*C07K 14/47* (2006.01)
*C07K 14/725* (2006.01)
*A61K 39/00* (2006.01)
*G01N 33/50* (2006.01)
*G01N 33/569* (2006.01)
*G01N 33/574* (2006.01)
*C07K 14/705* (2006.01)
*C07K 14/74* (2006.01)
*C07K 16/28* (2006.01)
*A61K 38/00* (2006.01)
*A61K 35/17* (2015.01)

(52) U.S. Cl.
CPC ...... *C07K 14/4748* (2013.01); *A61K 39/0011* (2013.01); *C07K 14/7051* (2013.01); *C07K 14/70521* (2013.01); *C07K 14/70539* (2013.01); *C07K 16/28* (2013.01); *G01N 33/505* (2013.01); *G01N 33/56972* (2013.01); *G01N 33/574* (2013.01); *A61K 35/17* (2013.01); *A61K 38/00* (2013.01); *A61K 39/00* (2013.01); *A61K 2039/5156* (2013.01); *A61K 2039/5158* (2013.01); *C07K 2317/56* (2013.01); *C07K 2317/622* (2013.01); *C07K 2319/02* (2013.01); *C07K 2319/03* (2013.01); *C07K 2319/30* (2013.01)

(58) Field of Classification Search
None
See application file for complete search history.

(56) References Cited

FOREIGN PATENT DOCUMENTS

| EP | 2 103 628 A1 | 9/2009 | |
|---|---|---|---|
| EP | 2 138 576 A1 | 12/2009 | |
| WO | WO 2010/094499 A1 | 8/2010 | |
| WO | WO 2011/057788 A1 | 5/2011 | |
| WO | WO 2011/113546 A1 | 9/2011 | |
| WO | WO 2012/156018 | * 11/2012 | ............. C07K 16/30 |
| WO | WO 2012/156018 A1 | 11/2012 | |

OTHER PUBLICATIONS

Lamers et al. (Molecular Therapy, 21(4): 904-912, 2013).*
Lamers et al. (Cytotherapy, 8(6): 542-553, 2006).*
Jena et al. (Blood, 116(7): 1035-1044, 2010).*
Sonja Offner et al: "Epithelial tight junction proteins as potential antibody targets for pancarcinoma therapy", Cancer Immunology, Immunotherapy, vol. 54, No. 5, May 1, 2005, pp. 431-445.
Morita Kazumasa et al: "Claudin multigene family encoding four-transmembrane domain protein components of tight junction strands", Proceedings of the National Academy of Sciences, National Academy of Sciences, vol. 96, No. 2, Jan. 19, 1999, pp. 511-516.
M Lal-Nag et al: "Claudin-6: a novel receptor for CPE-mediated cytotoxicity in ovarian cancer", Oncogenesis, vol. I, No. 11, Nov. 1, 2012, p. e33.
J. S. Mattsson et al: "Abstract A37: Ectopic claudin 6 and 18.2 expression as potential treatment target in non-small cell lung cancer", Clinical Cancer Research, vol. 20, No. 2 Supplement, Jan. 15, 2014, pp. A37-A37.

(Continued)

*Primary Examiner* — Nelson B Moseley, II
(74) *Attorney, Agent, or Firm* — Leason Ellis LLP

(57) ABSTRACT

The present invention provides Claudin-6-specific immunoreceptors (T cell receptors and artificial T cell receptors (chimeric antigen receptors; CARs)) and T cell epitopes which are useful for immunotherapy.

8 Claims, 37 Drawing Sheets
Specification includes a Sequence Listing.

(56) References Cited

OTHER PUBLICATIONS

International Search Report and Written Opinion in corresponding PCT Application No. PCT/EP2015/056899, dated Jun. 10, 2015.
International Preliminary Report on Patentability corresponding PCT Application No. PCT/EP2015/056899 dated Oct. 13, 2016.
Lal-Nag et al. "The claudins", *Genome Biology*, 2009, 10:235.
Pinthus et al., Immuno-Gene Therapy of Established Prostate Tumors Using Chimeric Receptor-redirected Human Lymphocytes, May 15, 2003, Cancer Research, 63: 2470-2476.
Beyer et al., Overcoming Physical Barriers in Cancer Therapy, Jan./Feb./Mar. 2013, Tissue Barriers 1:1 e23647.
Furuse et al., A single Gene Product, Claudin-1 or -2, Reconstitutes Tight Junction Strands and Recruits Occludin in Fibroblasts, Oct. 19, 1998, J. Cell Biol. 143(2): 391-401.
Klein et al., Examination of the contributions of size and avidity to the neutralization mechanisms of the anti-HIV antibodies b12 and 4E10, May 5, 2009, PNAS 106(18): 7385-7390.
Strokotov et al., Is there a difference between T- and B-lymphocyte morphology, Nov./Dec. 2009, J. biomed optics 14(6):064036.
Tsukita et al., Multifunctional Strands in Tight Junctions, Apr. 2001, Nature Reviews. Mol cell biol. 2:285-293.

\* cited by examiner

A)

A) (continued)

B)

B) (continued)

A)

B)

A)

A)

Figure 21:
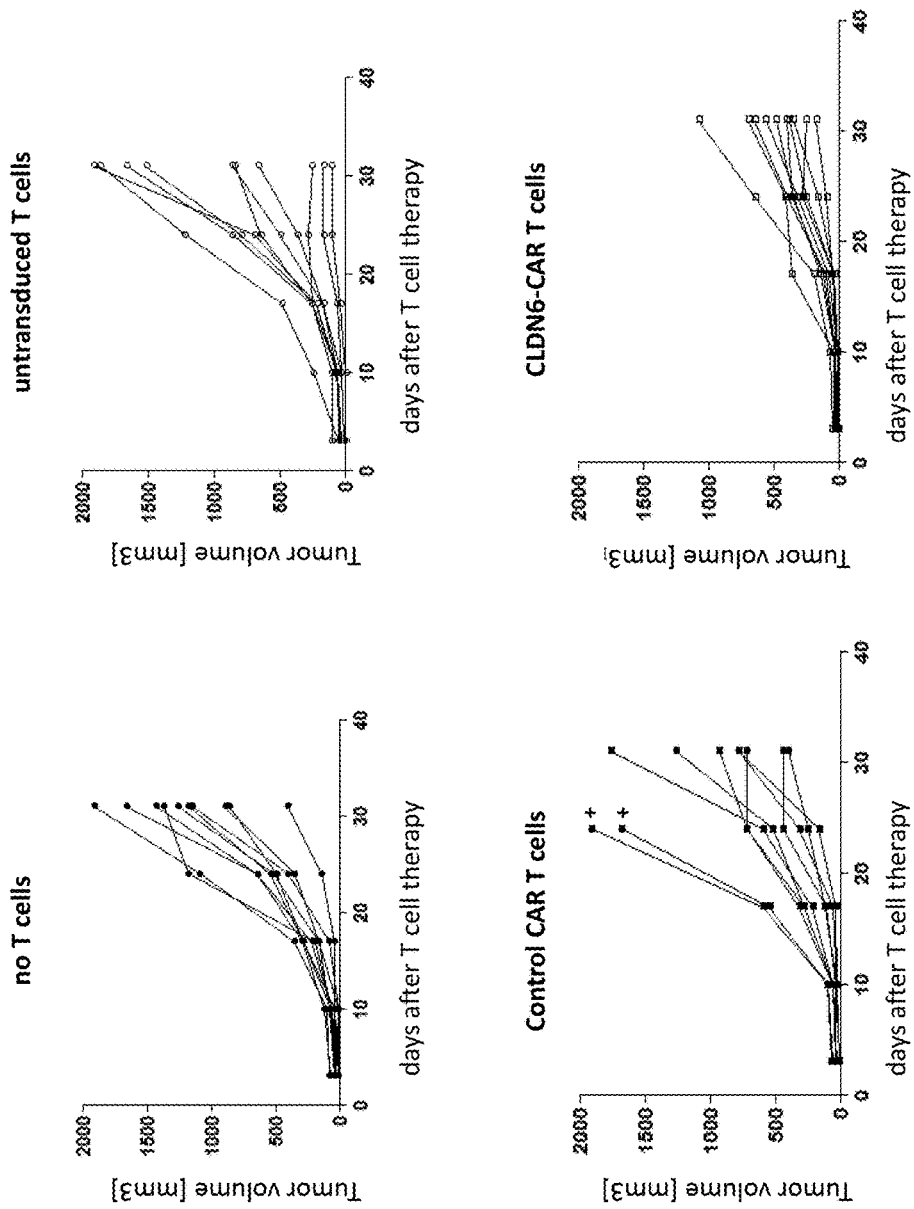

Figure 21
A)
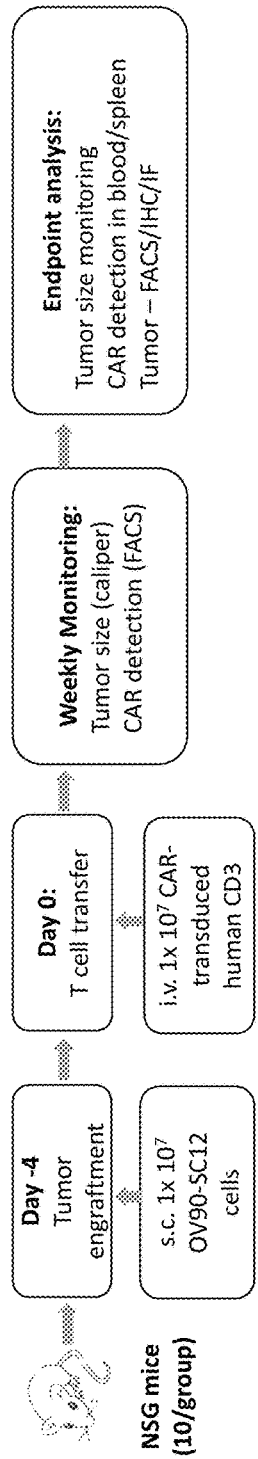
B)
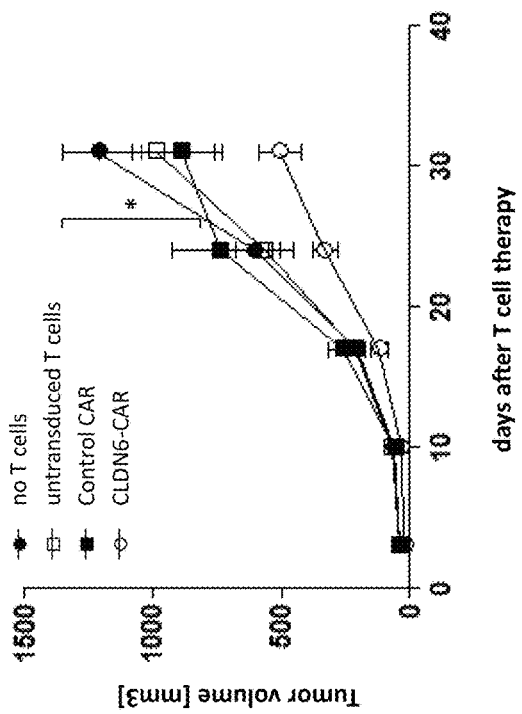

c)

A) CLDN6-CAR

B)

SEQUENCE LISTING

```
<160> NUMBER OF SEQ ID NOS: 46

<210> SEQ ID NO 1
<211> LENGTH: 220
<212> TYPE: PRT
<213> ORGANISM: Homo sapiens

<400> SEQUENCE: 1

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205
```

Arg Gly Pro Ser Glu Tyr Pro Thr Lys Asn Tyr Val
    210                 215                 220

<210> SEQ ID NO 2
<211> LENGTH: 220
<212> TYPE: PRT
<213> ORGANISM: Homo sapiens

<400> SEQUENCE: 2

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 3
<211> LENGTH: 9
<212> TYPE: PRT
<213> ORGANISM: Artificial Sequence
<220> FEATURE:
<223> OTHER INFORMATION: T cell epitope

<400> SEQUENCE: 3

Ala Leu Phe Gly Leu Leu Val Tyr Leu
1               5

<210> SEQ ID NO 4
<211> LENGTH: 9
<212> TYPE: PRT
<213> ORGANISM: Artificial Sequence
<220> FEATURE:
<223> OTHER INFORMATION: T cell epitope

<400> SEQUENCE: 4

Thr Leu Leu Gly Trp Val Asn Gly Leu
1               5

<210> SEQ ID NO 5
<211> LENGTH: 9
<212> TYPE: PRT
<213> ORGANISM: Artificial Sequence
<220> FEATURE:
<223> OTHER INFORMATION: T cell epitope

<400> SEQUENCE: 5

Gln Ile Leu Gly Val Val Leu Thr Leu
1               5

<210> SEQ ID NO 6
<211> LENGTH: 269
<212> TYPE: PRT
<213> ORGANISM: Homo sapiens

<400> SEQUENCE: 6

Met Leu Leu Ala Leu Leu Ser Val Leu Gly Ile His Phe Leu Leu Arg
1               5                   10                  15

Asp Ala Gln Ala Gln Ser Val Thr Gln Pro Asp Ala Arg Val Thr Val
                20                  25                  30

Ser Glu Gly Ala Ser Leu Gln Leu Arg Cys Lys Tyr Ser Tyr Phe Gly
            35                  40                  45

Thr Pro Tyr Leu Phe Trp Tyr Val Gln Tyr Pro Arg Gln Gly Leu Gln
        50                  55                  60

Leu Leu Leu Lys Tyr Tyr Pro Gly Asp Pro Val Val Gln Gly Val Asn
65                  70                  75                  80

Gly Phe Glu Ala Glu Phe Ser Lys Ser Asn Ser Ser Phe His Leu Arg
                85                  90                  95

Lys Ala Ser Val His Trp Ser Asp Trp Ala Val Tyr Phe Cys Ala Val
            100                 105                 110

Ser Met Ser Ser Gly Thr Tyr Gln Arg Phe Gly Thr Gly Thr Lys Leu
        115                 120                 125

Gln Val Val Pro Asn Ile Gln Asn Pro Glu Pro Ala Val Tyr Gln Leu
130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 7
<211> LENGTH: 304
<212> TYPE: PRT
<213> ORGANISM: Homo sapiens

<400> SEQUENCE: 7

Met Arg Val Arg Leu Ile Ser Ala Val Val Leu Cys Phe Leu Gly Thr
1               5                   10                  15

Gly Leu Val Asp Met Lys Val Thr Gln Met Pro Arg Tyr Leu Ile Lys
            20                  25                  30

Arg Met Gly Glu Asn Val Leu Leu Glu Cys Gly Gln Asp Met Ser His
        35                  40                  45

Glu Thr Met Tyr Trp Tyr Arg Gln Asp Pro Gly Leu Gly Leu Gln Leu
    50                  55                  60

Ile Tyr Ile Ser Tyr Asp Val Asp Ser Asn Ser Glu Gly Asp Ile Pro
65                  70                  75                  80

Lys Gly Tyr Arg Val Ser Arg Lys Lys Arg Glu His Phe Ser Leu Ile
                85                  90                  95

Leu Asp Ser Ala Lys Thr Asn Gln Thr Ser Val Tyr Phe Cys Ala Ser
            100                 105                 110

Ser Ser Gln Asn Gln Asp Thr Gln Tyr Phe Gly Pro Gly Thr Arg Leu
        115                 120                 125

Leu Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Gly Leu Val Leu Met Ala Met Val Lys Lys Lys Asn Ser
    290                 295                 300

<210> SEQ ID NO 8
<211> LENGTH: 268
<212> TYPE: PRT
<213> ORGANISM: Homo sapiens

<400> SEQUENCE: 8

Met Asp Ser Phe Pro Gly Phe Val Ala Val Ile Leu Leu Ile Leu Gly
1               5                   10                  15

Arg Thr His Gly Asp Ser Val Thr Gln Thr Glu Gly Gln Val Thr Val
            20                  25                  30

Ser Glu Ser Lys Ser Leu Ile Ile Asn Cys Thr Tyr Ser Ala Thr Ser
        35                  40                  45

Ile Gly Tyr Pro Asn Leu Phe Trp Tyr Val Arg Tyr Pro Gly Glu Gly
    50                  55                  60

```
Leu Gln Leu Leu Leu Lys Val Ile Thr Ala Gly Gln Lys Gly Ser Ser
 65                  70                  75                  80

Arg Gly Phe Glu Ala Thr Tyr Asn Lys Glu Ala Thr Ser Phe His Leu
                 85                  90                  95

Gln Lys Ala Ser Val Gln Glu Ser Asp Ser Ala Val Tyr Tyr Cys Ala
            100                 105                 110

Leu Asn Asn Gln Gly Lys Leu Ile Phe Gly Gln Gly Thr Lys Leu Ser
            115                 120                 125

Ile Lys Pro Asn Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 9
<211> LENGTH: 303
<212> TYPE: PRT
<213> ORGANISM: Homo sapiens

<400> SEQUENCE: 9

Met Gly Ser Arg Leu Phe Phe Val Leu Ser Ser Leu Leu Cys Ser Lys
 1               5                  10                  15

His Met Glu Ala Ala Val Thr Gln Ser Pro Arg Asn Lys Val Ala Val
            20                   25                  30

Thr Gly Gly Lys Val Thr Leu Ser Cys Asn Gln Thr Asn Asn His Asn
         35                  40                  45

Asn Met Tyr Trp Tyr Arg Gln Asp Thr Gly His Gly Leu Arg Leu Ile
 50                  55                  60

His Tyr Ser Tyr Gly Ala Gly Ser Thr Glu Lys Gly Asp Ile Pro Asp
 65                  70                  75                  80

Gly Tyr Lys Ala Ser Arg Pro Ser Gln Glu Asn Phe Ser Leu Ile Leu
                 85                  90                  95

Glu Leu Ala Thr Pro Ser Gln Thr Ser Val Tyr Phe Cys Ala Ser Gly
            100                 105                 110

Gly Asp Ser Gln Asn Thr Leu Tyr Phe Gly Ala Gly Thr Arg Leu Ser
            115                 120                 125

Val Leu Glu Asp Leu Arg Asn Val Thr Pro Pro Lys Val Ser Leu Phe
130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175
```

```
Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
            195                 200                 205

Ser Ala Thr Phe Trp His Asn Pro Arg Asn His Phe Arg Cys Gln Val
210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
                260                 265                 270

Ile Leu Tyr Glu Ile Leu Leu Gly Lys Ala Thr Leu Tyr Ala Val Leu
                275                 280                 285

Val Ser Gly Leu Val Leu Met Ala Met Val Lys Lys Lys Asn Ser
                290                 295                 300

<210> SEQ ID NO 10
<211> LENGTH: 273
<212> TYPE: PRT
<213> ORGANISM: Homo sapiens

<400> SEQUENCE: 10

Met Leu Ile Leu Ser Leu Leu Gly Ala Ala Phe Gly Ser Ile Cys Phe
1               5                   10                  15

Ala Thr Ser Met Ala Gln Lys Val Thr Gln Thr Gln Thr Ser Ile Ser
            20                  25                  30

Val Val Glu Lys Thr Thr Val Thr Met Asp Cys Val Tyr Glu Thr Arg
        35                  40                  45

Asp Ser Ser Tyr Phe Leu Phe Trp Tyr Lys Gln Thr Ala Ser Gly Glu
    50                  55                  60

Ile Val Phe Leu Ile Arg Gln Asp Ser Tyr Lys Lys Glu Asn Ala Thr
65                  70                  75                  80

Val Gly His Tyr Ser Leu Asn Phe Gln Lys Pro Lys Ser Ser Ile Gly
                85                  90                  95

Leu Ile Ile Thr Ala Thr Gln Ile Glu Asp Ser Ala Val Tyr Phe Cys
            100                 105                 110

Ala Met Arg Glu Ala Ala Asn Ser Gly Thr Tyr Gln Arg Phe Gly Thr
        115                 120                 125

Gly Thr Lys Leu Gln Val Val Pro Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
```

```
                        245                 250                 255
Leu Lys Val Ala Gly Phe Asn Leu Leu Met Thr Leu Arg Leu Trp Ser
                260                 265                 270
Ser
```

<210> SEQ ID NO 11
<211> LENGTH: 305
<212> TYPE: PRT
<213> ORGANISM: Homo sapiens

<400> SEQUENCE: 11

```
Met Gly Ser Ile Phe Leu Ser Cys Leu Ala Val Cys Leu Leu Val Ala
1               5                   10                  15
Gly Pro Val Asp Pro Lys Ile Ile Gln Lys Pro Lys Tyr Leu Val Ala
            20                  25                  30
Val Thr Gly Ser Glu Lys Ile Leu Ile Cys Glu Gln Tyr Leu Gly His
        35                  40                  45
Asn Ala Met Tyr Trp Tyr Arg Gln Ser Ala Lys Lys Pro Leu Glu Phe
    50                  55                  60
Met Phe Ser Tyr Ser Tyr Gln Lys Leu Met Asp Asn Gln Thr Ala Ser
65                  70                  75                  80
Ser Arg Phe Gln Pro Gln Ser Ser Lys Lys Asn His Leu Asp Leu Gln
                85                  90                  95
Ile Thr Ala Leu Lys Pro Asp Asp Ser Ala Thr Tyr Phe Cys Ala Ser
            100                 105                 110
Ser Gln Gln Asn Ser Gly Asn Thr Leu Tyr Phe Gly Glu Gly Ser Arg
        115                 120                 125
Leu Ile Val Val Glu Asp Leu Arg Asn Val Thr Pro Pro Lys Val Ser
    130                 135                 140
Leu Phe Glu Pro Ser Lys Ala Glu Ile Ala Asn Lys Gln Lys Ala Thr
145                 150                 155                 160
Leu Val Cys Leu Ala Arg Gly Phe Phe Pro Asp His Val Glu Leu Ser
                165                 170                 175
Trp Trp Val Asn Gly Lys Glu Val His Ser Gly Val Ser Thr Asp Pro
            180                 185                 190
Gln Ala Tyr Lys Glu Ser Asn Tyr Ser Tyr Cys Leu Ser Ser Arg Leu
        195                 200                 205
Arg Val Ser Ala Thr Phe Trp His Asn Pro Arg Asn His Phe Arg Cys
    210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                245                 250                 255
Ala Asp Cys Gly Ile Thr Ser Ala Ser Tyr Gln Gln Gly Val Leu Ser
            260                 265                 270
Ala Thr Ile Leu Tyr Glu Ile Leu Leu Gly Lys Ala Thr Leu Tyr Ala
        275                 280                 285
Val Leu Val Ser Thr Leu Val Val Met Ala Met Val Lys Arg Lys Asn
    290                 295                 300
Ser
305
```

<210> SEQ ID NO 12
<211> LENGTH: 270
<212> TYPE: PRT

<213> ORGANISM: Homo sapiens

<400> SEQUENCE: 12

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Thr Cys Thr Tyr Thr Asp
        35                  40                  45

Pro Asn Ser Tyr Tyr Phe Phe Trp Tyr Lys Gln Glu Pro Gly Ala Ser
    50                  55                  60

Leu Gln Leu Leu Met Lys Val Phe Ser Ser Thr Glu Ile Asn Glu Gly
65                  70                  75                  80

Gln Gly Phe Thr Val Leu Leu Asn Lys Lys Asp Lys Arg Leu Ser Leu
                85                  90                  95

Asn Leu Thr Ala Ala His Pro Gly Asp Ser Ala Ala Tyr Phe Cys Ala
            100                 105                 110

Val Glu Ser Ser Ser Phe Ser Lys Leu Val Phe Gly Gln Gly Thr Ser
        115                 120                 125

Leu Ser Val Val Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 13
<211> LENGTH: 307
<212> TYPE: PRT
<213> ORGANISM: Homo sapiens

<400> SEQUENCE: 13

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
            20                  25                  30

Gly Gln Gly Gln Lys Ala Lys Met Arg Cys Ile Pro Glu Lys Gly His
        35                  40                  45

Pro Val Val Phe Trp Tyr Gln Gln Asn Lys Asn Asn Glu Phe Lys Phe
    50                  55                  60

Leu Ile Asn Phe Gln Asn Gln Glu Val Leu Gln Gln Ile Asp Met Thr
65                  70                  75                  80

Glu Lys Arg Phe Ser Ala Glu Cys Pro Ser Asn Ser Pro Cys Ser Leu

```
                    85                  90                  95
Glu Ile Gln Ser Ser Glu Ala Gly Asp Ser Ala Leu Tyr Leu Cys Ala
                100                 105                 110

Ser Ser Leu Thr Gly Gly Ala Gln Asp Thr Gln Tyr Phe Gly Pro Gly
            115                 120                 125

Thr Arg Leu Leu Val Leu Glu Asp Leu Arg Asn Val Thr Pro Pro Lys
        130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
    290                 295                 300

Lys Asn Ser
305

<210> SEQ ID NO 14
<211> LENGTH: 266
<212> TYPE: PRT
<213> ORGANISM: Homo sapiens

<400> SEQUENCE: 14

Met Gln Arg Asn Leu Val Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Gly Ser Ala Leu Arg Cys Asn Phe Thr Thr Thr
        35                  40                  45

Met Arg Ala Val Gln Trp Phe Arg Lys Asn Ser Arg Gly Ser Leu Ile
    50                  55                  60

Asn Leu Phe Tyr Leu Ala Ser Gly Thr Lys Glu Asn Gly Arg Leu Lys
65                  70                  75                  80

Ser Ala Phe Asp Ser Lys Glu Arg Tyr Ser Thr Leu His Ile Arg Asp
                85                  90                  95

Ala Gln Leu Glu Asp Ser Gly Thr Tyr Phe Cys Ala Ala Glu Gly Gly
                100                 105                 110

Gly Asn Tyr Lys Pro Thr Phe Gly Lys Gly Thr Ser Leu Val Val His
            115                 120                 125

Pro Tyr Ile Gln Asn Pro Glu Pro Ala Val Tyr Gln Leu Lys Asp Pro
        130                 135                 140
```

```
Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Thr Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Ser Val Met Gly Leu Arg Ile Leu Leu Leu Lys Val Ala Gly Phe Asn
                245                 250                 255

Leu Leu Met Thr Leu Arg Leu Trp Ser Ser
            260                 265

<210> SEQ ID NO 15
<211> LENGTH: 302
<212> TYPE: PRT
<213> ORGANISM: Homo sapiens

<400> SEQUENCE: 15

Met Leu Tyr Ser Leu Leu Ala Phe Leu Leu Gly Met Phe Leu Gly Val
1               5                   10                  15

Ser Ala Gln Thr Ile His Gln Trp Pro Val Ala Glu Ile Lys Ala Val
            20                  25                  30

Gly Ser Pro Leu Ser Leu Gly Cys Thr Ile Lys Gly Lys Ser Ser Pro
        35                  40                  45

Asn Leu Tyr Trp Tyr Trp Gln Ala Thr Gly Gly Thr Leu Gln Gln Leu
    50                  55                  60

Phe Tyr Ser Ile Thr Val Gly Gln Val Glu Ser Val Val Gln Leu Asn
65                  70                  75                  80

Leu Ser Ala Ser Arg Pro Lys Asp Asp Gln Phe Ile Leu Ser Thr Glu
                85                  90                  95

Lys Leu Leu Leu Ser His Ser Gly Phe Tyr Leu Cys Ala Trp Ser Pro
            100                 105                 110

Pro Ile Asn Thr Glu Val Phe Phe Gly Lys Gly Thr Arg Leu Thr Val
        115                 120                 125

Val Glu Asp Leu Arg Asn Val Thr Pro Pro Lys Val Ser Leu Phe Glu
    130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
    210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255
```

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
            275                 280                 285

Ser Thr Leu Val Val Met Ala Met Val Lys Arg Lys Asn Ser
            290                 295                 300

<210> SEQ ID NO 16
<211> LENGTH: 271
<212> TYPE: PRT
<213> ORGANISM: Homo sapiens

<400> SEQUENCE: 16

Met Asp Ser Ser Pro Gly Phe Val Ala Val Ile Leu Leu Ile Leu Gly
1               5                   10                  15

Arg Thr His Gly Asp Ser Val Thr Gln Thr Glu Gly Pro Val Thr Val
            20                  25                  30

Ser Glu Ser Glu Ser Leu Ile Ile Asn Cys Thr Tyr Ser Ala Thr Ser
            35                  40                  45

Ile Ala Tyr Pro Asn Leu Phe Trp Tyr Val Arg Tyr Pro Gly Glu Gly
    50                  55                  60

Leu Gln Leu Leu Leu Lys Val Ile Thr Ala Gly Gln Lys Gly Ser Ser
65                  70                  75                  80

Arg Gly Phe Glu Ala Thr Tyr Asn Lys Glu Thr Thr Ser Phe His Leu
                85                  90                  95

Gln Lys Ala Ser Val Gln Glu Ser Asp Ser Ala Val Tyr Tyr Cys Ala
            100                 105                 110

Leu Gly Glu Thr Gly Ser Phe Asn Lys Leu Thr Phe Gly Ala Gly Thr
            115                 120                 125

Arg Leu Ala Val Cys Pro Tyr Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 17
<211> LENGTH: 304
<212> TYPE: PRT
<213> ORGANISM: Homo sapiens

<400> SEQUENCE: 17

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
            20                  25                  30

Gly Gln Gly Gln Lys Ala Lys Met Arg Cys Ile Pro Glu Lys Gly His
        35                  40                  45

Pro Val Val Phe Trp Tyr Gln Gln Asn Lys Asn Asn Glu Phe Lys Phe
50                  55                  60

Leu Ile Asn Phe Gln Asn Gln Glu Val Leu Gln Gln Ile Asp Met Thr
65                  70                  75                  80

Glu Lys Arg Phe Ser Ala Glu Cys Pro Ser Asn Ser Pro Cys Ser Leu
                85                  90                  95

Glu Ile Gln Ser Ser Glu Ala Gly Asp Ser Ala Leu Tyr Leu Cys Ala
            100                 105                 110

Ser Ser Leu Gly Ile Tyr Glu Gln Tyr Phe Gly Pro Gly Thr Arg Leu
        115                 120                 125

Thr Val Leu Glu Asp Leu Arg Asn Val Thr Pro Pro Lys Val Ser Leu
130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Gly Leu Val Leu Met Ala Met Val Lys Lys Lys Asn Ser
290                 295                 300

<210> SEQ ID NO 18
<211> LENGTH: 274
<212> TYPE: PRT
<213> ORGANISM: Homo sapiens

<400> SEQUENCE: 18

Met Leu Ile Leu Ser Leu Leu Gly Ala Ala Phe Gly Ser Ile Cys Phe
1               5                   10                  15

Ala Ala Thr Ser Met Ala Gln Lys Val Thr Gln Thr Gln Thr Ser Ile
            20                  25                  30

Ser Val Val Glu Lys Thr Thr Val Thr Met Asp Cys Val Tyr Glu Thr
        35                  40                  45

Arg Asp Ser Ser Tyr Phe Leu Phe Trp Tyr Lys Gln Thr Ala Ser Gly
        50                  55                  60

Glu Ile Val Phe Leu Ile Arg Gln Asp Ser Tyr Lys Lys Glu Asn Ala
65                  70                  75                  80

Thr Val Gly His Tyr Ser Leu Asn Phe Gln Lys Pro Lys Ser Ser Ile

```
            85                  90                  95
Gly Leu Ile Ile Thr Ala Thr Gln Ile Glu Asp Ser Ala Val Tyr Phe
            100                 105                 110

Cys Ala Met Arg Asp Ser Ser Gly Gly Asn Tyr Lys Pro Thr Phe Gly
            115                 120                 125

Lys Gly Thr Ser Leu Val Val His Pro Tyr Ile Gln Asn Pro Glu Pro
            130                 135                 140

Ala Val Tyr Gln Leu Lys Asp Pro Arg Ser Gln Asp Ser Thr Leu Cys
145                 150                 155                 160

Leu Phe Thr Asp Phe Asp Ser Gln Ile Asn Val Pro Lys Thr Met Glu
                165                 170                 175

Ser Gly Thr Phe Ile Thr Asp Lys Thr Val Leu Asp Met Lys Ala Met
                180                 185                 190

Asp Ser Lys Ser Asn Gly Ala Ile Ala Trp Ser Asn Gln Thr Ser Phe
                195                 200                 205

Thr Cys Gln Asp Ile Phe Lys Glu Thr Asn Ala Thr Tyr Pro Ser Ser
            210                 215                 220

Asp Val Pro Cys Asp Ala Thr Leu Thr Glu Lys Ser Phe Glu Thr Asp
225                 230                 235                 240

Met Asn Leu Asn Phe Gln Asn Leu Ser Val Met Gly Leu Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 19
<211> LENGTH: 307
<212> TYPE: PRT
<213> ORGANISM: Homo sapiens

<400> SEQUENCE: 19

Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
            20                  25                  30

Val Thr Gly Ser Glu Lys Ile Leu Ile Cys Glu Gln Tyr Leu Gly His
            35                  40                  45

Asn Ala Met Tyr Trp Tyr Arg Gln Ser Ala Lys Lys Pro Leu Glu Phe
        50                  55                  60

Met Phe Ser Tyr Ser Tyr Gln Lys Leu Met Asp Asn Gln Thr Ala Ser
65                  70                  75                  80

Ser Arg Phe Gln Pro Gln Ser Ser Lys Lys Asn His Leu Asp Leu Gln
                85                  90                  95

Ile Thr Ala Leu Lys Pro Asp Asp Ser Ala Thr Tyr Phe Cys Ala Ser
            100                 105                 110

Ser Gln Glu Asp Trp Gly Ser Gln Asn Thr Leu Tyr Phe Gly Ala Gly
            115                 120                 125

Thr Arg Leu Ser Val Leu Glu Asp Leu Arg Asn Val Thr Pro Pro Lys
            130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
```

```
            180                 185                 190
Asp Pro Gln Ala Tyr Lys Glu Ser Asn Tyr Ser Tyr Cys Leu Ser Ser
            195                 200                 205

Arg Leu Arg Val Ser Ala Thr Phe Trp His Asn Pro Arg Asn His Phe
        210                 215                 220

Arg Cys Gln Val Gln Phe His Gly Leu Ser Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
    290                 295                 300

Lys Asn Ser
305

<210> SEQ ID NO 20
<211> LENGTH: 269
<212> TYPE: PRT
<213> ORGANISM: Homo sapiens

<400> SEQUENCE: 20

Met Lys Arg Leu Val Cys Ser Leu Leu Gly Leu Leu Cys Thr Gln Val
1               5                   10                  15

Cys Trp Val Lys Gly Gln Gln Val Gln Gln Ser Pro Ala Ser Leu Val
            20                  25                  30

Leu Gln Glu Gly Glu Asn Ala Glu Leu Gln Cys Asn Phe Ser Ser Thr
        35                  40                  45

Ala Thr Arg Leu Gln Trp Phe Tyr Gln Arg Pro Gly Gly Ser Leu Val
    50                  55                  60

Ser Leu Leu Tyr Asn Pro Ser Gly Thr Lys His Thr Gly Arg Leu Thr
65                  70                  75                  80

Ser Thr Thr Val Thr Lys Glu Arg Arg Ser Ser Leu His Ile Ser Ser
                85                  90                  95

Ser Gln Thr Thr Asp Ser Gly Thr Tyr Phe Cys Ala Met Ser Ser Asn
            100                 105                 110

Ser Gly Gly Ser Asn Ala Lys Leu Thr Phe Gly Lys Gly Thr Lys Leu
        115                 120                 125

Ser Val Lys Ser Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240
```

Gln Asn Leu Ser Val Met Gly Leu Arg Ile Leu Leu Lys Val Ala
            245                 250                 255

Gly Phe Asn Leu Leu Met Thr Leu Arg Leu Trp Ser Ser
            260                 265

<210> SEQ ID NO 21
<211> LENGTH: 305
<212> TYPE: PRT
<213> ORGANISM: Homo sapiens

<400> SEQUENCE: 21

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr Arg Val Thr
            20                  25                  30

Arg Val Gly Asn Glu Val Ser Phe Asn Cys Glu Gln Thr Leu Asp His
        35                  40                  45

Asn Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Leu Glu Asp Ser Ala Val Tyr Leu Cys Ala Ser
            100                 105                 110

Ser Asp Trp Gly Asp Ser Tyr Glu Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300

Ser
305

<210> SEQ ID NO 22
<211> LENGTH: 274
<212> TYPE: PRT
<213> ORGANISM: Homo sapiens

<400> SEQUENCE: 22

Met Leu Ile Leu Ser Leu Leu Gly Ala Ala Phe Gly Ser Ile Cys Phe
1               5                   10                  15

Ala Ala Thr Ser Met Ala Gln Lys Val Thr Gln Thr Gln Thr Ser Ile
            20                  25                  30

Ser Val Val Glu Lys Thr Thr Val Thr Met Asp Cys Val Tyr Glu Thr
                35                  40                  45

Arg Asp Ser Ser Tyr Phe Leu Phe Trp Tyr Lys Gln Thr Ala Ser Gly
        50                  55                  60

Glu Ile Val Phe Leu Ile Arg Gln Asp Ser Tyr Lys Lys Glu Asn Ala
65                  70                  75                  80

Thr Val Gly His Tyr Ser Leu Asn Phe Gln Lys Pro Lys Ser Ser Ile
                85                  90                  95

Gly Leu Ile Ile Thr Ala Thr Gln Ile Glu Asp Ser Ala Val Tyr Phe
                100                 105                 110

Cys Ala Met Arg Val Ala Ser Ser Gly Ser Trp Gln Leu Ile Phe Gly
            115                 120                 125

Ser Gly Thr Gln Leu Thr Val Met Pro Asp Ile Gln Asn Pro Glu Pro
130                 135                 140

Ala Val Tyr Gln Leu Lys Asp Pro Arg Ser Gln Asp Ser Thr Leu Cys
145                 150                 155                 160

Leu Phe Thr Asp Phe Asp Ser Gln Ile Asn Val Pro Lys Thr Met Glu
                165                 170                 175

Ser Gly Thr Phe Ile Thr Asp Lys Thr Val Leu Asp Met Lys Ala Met
            180                 185                 190

Asp Ser Lys Ser Asn Gly Ala Ile Ala Trp Ser Asn Gln Thr Ser Phe
            195                 200                 205

Thr Cys Gln Asp Ile Phe Lys Glu Thr Asn Ala Thr Tyr Pro Ser Ser
        210                 215                 220

Asp Val Pro Cys Asp Ala Thr Leu Thr Glu Lys Ser Phe Glu Thr Asp
225                 230                 235                 240

Met Asn Leu Asn Phe Gln Asn Leu Ser Val Met Gly Leu Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 23
<211> LENGTH: 306
<212> TYPE: PRT
<213> ORGANISM: Homo sapiens

<400> SEQUENCE: 23

Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
            20                  25                  30

Val Thr Gly Ser Glu Lys Ile Leu Ile Cys Glu Gln Tyr Leu Gly His
                35                  40                  45

Asn Ala Met Tyr Trp Tyr Arg Gln Ser Ala Lys Lys Pro Leu Glu Phe
        50                  55                  60

Met Phe Ser Tyr Ser Tyr Gln Lys Leu Met Asp Asn Gln Thr Ala Ser
65                  70                  75                  80

Ser Arg Phe Gln Pro Gln Ser Lys Lys Asn His Leu Asp Leu Gln
            85                  90                  95

Ile Thr Ala Leu Lys Pro Asp Asp Ser Ala Thr Tyr Phe Cys Ala Ser
            100                 105                 110

Ser Gln Gly Asp Asn Asn Tyr Ala Glu Gln Phe Phe Gly Pro Gly Thr
            115                 120                 125

Arg Leu Thr Val Leu Glu Asp Leu Arg Asn Val Thr Pro Pro Lys Val
            130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
            165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
            210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
            245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Gly Leu Val Leu Met Ala Met Val Lys Lys Lys
            290                 295                 300

Asn Ser
305

<210> SEQ ID NO 24
<211> LENGTH: 268
<212> TYPE: PRT
<213> ORGANISM: Homo sapiens

<400> SEQUENCE: 24

Met Lys Thr Val Thr Gly Pro Leu Leu Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Ile Ile Ile Cys Thr Tyr Thr Asp
            35                  40                  45

Ser Ala Thr Ala Tyr Phe Ser Trp Tyr Lys Gln Glu Ala Gly Ala Gly
            50                  55                  60

Leu Gln Leu Leu Met Ser Val Leu Ser Asn Val Asp Arg Lys Glu Glu
65                  70                  75                  80

Gln Gly Leu Thr Val Leu Leu Asn Lys Lys Asp Lys Arg Leu Ser Leu
            85                  90                  95

Asn Leu Thr Ala Ala His Pro Gly Asp Ser Ala Val Tyr Phe Cys Ala
            100                 105                 110

Thr Asn Ala Gly Ala Lys Leu Thr Phe Gly Gly Gly Thr Arg Leu Thr
            115                 120                 125

Val Arg Pro Asp Ile Gln Asn Pro Glu Pro Ala Val Tyr Gln Leu Lys
            130                 135                 140

```
Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
        210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 25
<211> LENGTH: 306
<212> TYPE: PRT
<213> ORGANISM: Homo sapiens

<400> SEQUENCE: 25

Met Gly Cys Arg Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
            35                  40                  45

Asp Thr Met Tyr Trp Tyr Lys Gln Asp Ser Lys Lys Leu Leu Lys Ile
        50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Leu Tyr Trp Gly Asp Ser Tyr Glu Gln Tyr Phe Gly Pro Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
```

```
                      245                 250                 255
Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
        290                 295                 300

Asn Ser
305

<210> SEQ ID NO 26
<211> LENGTH: 277
<212> TYPE: PRT
<213> ORGANISM: Homo sapiens

<400> SEQUENCE: 26

Met Asp Lys Asn Leu Thr Ala Ser Phe Leu Leu Gly Leu His Leu
1               5                   10                  15

Ala Gly Val Ser Gly Gln Gln Glu Lys Arg Asp Gln Gln Val Arg
            20                  25                  30

Gln Ser Pro Gln Ser Leu Thr Val Trp Glu Gly Glu Thr Ala Ile Leu
        35                  40                  45

Asn Cys Ser Tyr Glu Asn Ser Ala Phe Asp Tyr Phe Pro Trp Tyr Gln
    50                  55                  60

Gln Phe Pro Gly Glu Gly Pro Ala Leu Leu Ile Ser Ile Leu Ser Val
65                  70                  75                  80

Ser Asp Lys Lys Glu Asp Gly Arg Phe Thr Ile Phe Phe Asn Lys Arg
                85                  90                  95

Glu Lys Lys Leu Ser Leu His Ile Ala Asp Ser Gln Pro Gly Asp Ser
            100                 105                 110

Ala Thr Tyr Phe Cys Ala Ala Ser Leu Ser Ser Gly Ser Trp Gln Leu
        115                 120                 125

Ile Phe Gly Ser Gly Thr Gln Leu Thr Val Met Pro Asp Ile Gln Asn
130                 135                 140

Pro Glu Pro Ala Val Tyr Gln Leu Lys Asp Pro Arg Ser Gln Asp Ser
145                 150                 155                 160

Thr Leu Cys Leu Phe Thr Asp Phe Asp Ser Gln Ile Asn Val Pro Lys
                165                 170                 175

Thr Met Glu Ser Gly Thr Phe Ile Thr Asp Lys Thr Val Leu Asp Met
            180                 185                 190

Lys Ala Met Asp Ser Lys Ser Asn Gly Ala Ile Ala Trp Ser Asn Gln
        195                 200                 205

Thr Ser Phe Thr Cys Gln Asp Ile Phe Lys Glu Thr Asn Ala Thr Tyr
    210                 215                 220

Pro Ser Ser Asp Val Pro Cys Asp Ala Thr Leu Thr Glu Lys Ser Phe
225                 230                 235                 240

Glu Thr Asp Met Asn Leu Asn Phe Gln Asn Leu Ser Val Met Gly Leu
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 27
<211> LENGTH: 305
```

<212> TYPE: PRT
<213> ORGANISM: Homo sapiens

<400> SEQUENCE: 27

```
Met Asp Ile Trp Leu Leu Gly Trp Ile Ile Phe Ser Phe Leu Glu Ala
1               5                   10                  15
Gly His Thr Gly Pro Lys Val Leu Gln Ile Pro Ser His Gln Ile Ile
            20                  25                  30
Asp Met Gly Gln Met Val Thr Leu Asn Cys Asp Pro Val Ser Asn His
        35                  40                  45
Leu Tyr Phe Tyr Trp Tyr Lys Gln Ile Leu Gly Gln Gln Met Glu Phe
    50                  55                  60
Leu Val Asn Phe Tyr Asn Gly Lys Val Met Glu Lys Ser Lys Leu Phe
65                  70                  75                  80
Lys Asp Gln Phe Ser Val Glu Arg Pro Asp Gly Ser Tyr Phe Thr Leu
                85                  90                  95
Lys Ile Gln Pro Thr Ala Leu Glu Asp Ser Ala Val Tyr Phe Cys Ala
            100                 105                 110
Ser Ser Leu Val Gly Gly Tyr Glu Gln Tyr Phe Gly Pro Gly Thr Arg
        115                 120                 125
Leu Thr Val Leu Glu Asp Leu Arg Asn Val Thr Pro Pro Lys Val Ser
    130                 135                 140
Leu Phe Glu Pro Ser Lys Ala Glu Ile Ala Asn Lys Gln Lys Ala Thr
145                 150                 155                 160
Leu Val Cys Leu Ala Arg Gly Phe Phe Pro Asp His Val Glu Leu Ser
                165                 170                 175
Trp Trp Val Asn Gly Lys Glu Val His Ser Gly Val Ser Thr Asp Pro
            180                 185                 190
Gln Ala Tyr Lys Glu Ser Asn Tyr Ser Tyr Cys Leu Ser Ser Arg Leu
        195                 200                 205
Arg Val Ser Ala Thr Phe Trp His Asn Pro Arg Asn His Phe Arg Cys
    210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                245                 250                 255
Ala Asp Cys Gly Ile Thr Ser Ala Ser Tyr His Gln Gly Val Leu Ser
            260                 265                 270
Ala Thr Ile Leu Tyr Glu Ile Leu Leu Gly Lys Ala Thr Leu Tyr Ala
        275                 280                 285
Val Leu Val Ser Gly Leu Val Leu Met Ala Met Val Lys Lys Lys Asn
    290                 295                 300
Ser
305
```

<210> SEQ ID NO 28
<211> LENGTH: 268
<212> TYPE: PRT
<213> ORGANISM: Homo sapiens

<400> SEQUENCE: 28

```
Met Asp Ser Phe Pro Gly Phe Met Thr Val Met Leu Leu Ile Phe Thr
1               5                   10                  15
Arg Ala His Gly Asp Ser Val Thr Gln Thr Glu Gly Gln Val Ala Leu
            20                  25                  30
```

```
Ser Glu Glu Asp Phe Leu Thr Ile His Cys Asn Tyr Ser Ala Ser Gly
         35                  40                  45

Tyr Pro Ala Leu Phe Trp Tyr Val Gln Tyr Pro Gly Glu Gly Pro Gln
 50                  55                  60

Phe Leu Phe Arg Ala Ser Arg Asp Lys Glu Lys Gly Ser Ser Arg Gly
65                   70                  75                  80

Phe Glu Ala Thr Tyr Asp Lys Gly Thr Thr Ser Phe His Leu Arg Lys
                 85                  90                  95

Ala Ser Val Gln Glu Ser Asp Ser Ala Val Tyr Tyr Cys Ala Leu Gly
            100                 105                 110

Asn Asn Tyr Ala Gln Gly Leu Thr Phe Gly Leu Gly Thr Arg Val Ser
            115                 120                 125

Val Phe Pro Tyr Ile Gln Asn Pro Glu Pro Ala Val Tyr Gln Leu Lys
        130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 29
<211> LENGTH: 302
<212> TYPE: PRT
<213> ORGANISM: Homo sapiens

<400> SEQUENCE: 29

Met Gly Ser Arg Leu Phe Phe Val Val Leu Ile Leu Leu Cys Ala Lys
1               5                   10                  15

His Met Glu Ala Ala Val Thr Gln Ser Pro Arg Ser Lys Val Ala Val
            20                  25                  30

Thr Gly Gly Lys Val Thr Leu Ser Cys His Gln Thr Asn Asn His Asp
        35                  40                  45

Tyr Met Tyr Trp Tyr Arg Gln Asp Thr Gly His Gly Leu Arg Leu Ile
 50                  55                  60

His Tyr Ser Tyr Val Ala Asp Ser Thr Glu Lys Gly Asp Ile Pro Asp
65                   70                  75                  80

Gly Tyr Lys Ala Ser Arg Pro Ser Gln Glu Asn Phe Ser Leu Ile Leu
                 85                  90                  95

Glu Leu Ala Ser Leu Ser Gln Thr Ala Val Tyr Phe Cys Ala Ser Ser
            100                 105                 110

Thr Gly Asn Glu Arg Leu Phe Phe Gly His Gly Thr Lys Leu Ser Val
            115                 120                 125

Leu Glu Asp Leu Arg Asn Val Thr Pro Pro Lys Val Ser Leu Phe Glu
        130                 135                 140
```

```
Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
            195                 200                 205

Ala Thr Phe Trp His Asn Pro Arg Asn His Phe Arg Cys Gln Val Gln
210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr Gln Gln Gly Val Leu Ser Ala Thr Ile
            260                 265                 270

Leu Tyr Glu Ile Leu Leu Gly Lys Ala Thr Leu Tyr Ala Val Leu Val
            275                 280                 285

Ser Thr Leu Val Val Met Ala Met Val Lys Arg Lys Asn Ser
            290                 295                 300

<210> SEQ ID NO 30
<211> LENGTH: 117
<212> TYPE: PRT
<213> ORGANISM: Artificial Sequence
<220> FEATURE:
<223> OTHER INFORMATION: Antibody fragment

<400> SEQUENCE: 30

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Tyr Val Leu Asp Tyr Trp Gly Gln Gly Thr Thr
            100                 105                 110

Leu Thr Val Ser Ser
        115

<210> SEQ ID NO 31
<211> LENGTH: 106
<212> TYPE: PRT
<213> ORGANISM: Artificial Sequence
<220> FEATURE:
<223> OTHER INFORMATION: Antibody fragment

<400> SEQUENCE: 31

Ile Val Leu Thr Gln Ser Pro Ala Ile Met Ser Ala Ser Pro Gly Glu
1               5                   10                  15

Lys Val Thr Ile Thr Cys Ser Ala Ser Ser Ser Val Ser Tyr Leu His
```

```
                 20                  25                  30

Trp Phe Gln Gln Lys Pro Gly Thr Ser Pro Lys Leu Trp Val Tyr Ser
            35                  40                  45

Thr Ser Asn Leu Pro Ser Gly Val Pro Ala Arg Phe Gly Gly Ser Gly
        50                  55                  60

Ser Gly Thr Ser Tyr Ser Leu Thr Ile Ser Arg Met Glu Ala Glu Asp
65                  70                  75                  80

Ala Ala Thr Tyr Tyr Cys Gln Gln Arg Ser Ile Tyr Pro Pro Trp Thr
                85                  90                  95

Phe Gly Gly Gly Thr Lys Leu Glu Ile Lys
            100                 105

<210> SEQ ID NO 32
<211> LENGTH: 117
<212> TYPE: PRT
<213> ORGANISM: Artificial Sequence
<220> FEATURE:
<223> OTHER INFORMATION: Antibody fragment

<400> SEQUENCE: 32

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ile Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser
        115

<210> SEQ ID NO 33
<211> LENGTH: 106
<212> TYPE: PRT
<213> ORGANISM: Artificial Sequence
<220> FEATURE:
<223> OTHER INFORMATION: Antibody fragment

<400> SEQUENCE: 33

Ile Val Leu Thr Gln Ser Pro Ser Ile Met Ser Val Ser Pro Gly Glu
1               5                   10                  15

Lys Val Thr Ile Thr Cys Ser Ala Ser Ser Ser Val Ser Tyr Met His
                20                  25                  30

Trp Phe Gln Gln Lys Pro Gly Thr Ser Pro Lys Leu Cys Ile Tyr Ser
            35                  40                  45

Thr Ser Asn Leu Ala Ser Gly Val Pro Ala Arg Phe Ser Gly Arg Gly
        50                  55                  60

Ser Gly Thr Ser Tyr Ser Leu Thr Ile Ser Arg Val Ala Ala Glu Asp
65                  70                  75                  80

Ala Ala Thr Tyr Tyr Cys Gln Gln Arg Ser Asn Tyr Pro Pro Trp Thr
                85                  90                  95
```

Phe Gly Gly Gly Thr Lys Leu Glu Ile Lys
                100                 105

<210> SEQ ID NO 34
<211> LENGTH: 117
<212> TYPE: PRT
<213> ORGANISM: Artificial Sequence
<220> FEATURE:
<223> OTHER INFORMATION: Antibody fragment

<400> SEQUENCE: 34

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Ile Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Phe Tyr Cys
                85                  90                  95

Ala Arg Asp Phe Gly Tyr Val Leu Asp Tyr Trp Gly Gln Gly Thr Thr
            100                 105                 110

Leu Thr Val Ser Ser
        115

<210> SEQ ID NO 35
<211> LENGTH: 106
<212> TYPE: PRT
<213> ORGANISM: Artificial Sequence
<220> FEATURE:
<223> OTHER INFORMATION: Antibody fragment

<400> SEQUENCE: 35

Ile Val Leu Thr Gln Ser Pro Ala Ile Met Ser Ala Ser Pro Gly Glu
1               5                   10                  15

Lys Val Thr Ile Thr Cys Ser Ala Ser Ser Ser Val Ser Tyr Met His
            20                  25                  30

Trp Phe Gln Gln Lys Pro Gly Thr Ser Pro Lys Leu Trp Ile Tyr Ser
        35                  40                  45

Thr Ser Asn Leu Ala Ser Gly Val Pro Ala Arg Phe Ser Gly Ser Gly
    50                  55                  60

Ser Gly Thr Ser Tyr Ser Leu Thr Ile Ser Arg Val Ala Ala Glu Asp
65                  70                  75                  80

Ala Ala Thr Tyr Tyr Cys Gln Gln Arg Ser Thr Tyr Pro Pro Trp Thr
                85                  90                  95

Phe Gly Gly Gly Thr Lys Leu Glu Ile Lys
                100                 105

<210> SEQ ID NO 36
<211> LENGTH: 117
<212> TYPE: PRT
<213> ORGANISM: Artificial Sequence
<220> FEATURE:
<223> OTHER INFORMATION: Antibody fragment

<400> SEQUENCE: 36

Glu Val Gln Leu Gln Gln Ser Arg Pro Glu Leu Val Lys Pro Gly Ala

```
            1               5                   10                  15
        Ser Met Lys Ile Ser Cys Lys Ala Ser Gly Tyr Ser Phe Thr Gly Tyr
                        20                  25                  30

Thr Leu Asn Trp Val Lys Gln Ser His Gly Lys Asn Leu Glu Trp Ile
                        35                  40                  45

Gly Leu Ile Asn Pro Tyr Asn Gly Gly Ser Ser Tyr Asn Gln Lys Phe
                        50                  55                  60

Lys Asp Lys Ala Thr Leu Thr Val Asp Lys Ser Ser Ser Thr Ala Tyr
         65                 70                  75                  80

Met Glu Leu Leu Ser Leu Thr Ser Glu Asp Ser Ala Val Tyr Tyr Cys
                        85                  90                  95

Ala Arg Asp Tyr Gly Tyr Val Phe Asp Tyr Trp Gly Gln Gly Thr Thr
                        100                 105                 110

Leu Thr Val Ser Ser
                        115

<210> SEQ ID NO 37
<211> LENGTH: 106
<212> TYPE: PRT
<213> ORGANISM: Artificial Sequence
<220> FEATURE:
<223> OTHER INFORMATION: Antibody fragment

<400> SEQUENCE: 37

Ile Val Leu Thr Gln Ser Pro Ala Ile Met Ser Ala Ser Pro Gly Glu
         1                  5                   10                  15

Lys Val Thr Ile Thr Cys Ser Ala Ser Ser Ser Val Asn Tyr Met His
                        20                  25                  30

Trp Phe Gln Leu Lys Pro Gly Thr Ser Pro Lys Leu Leu Ile Tyr Ser
                        35                  40                  45

Thr Ser Asn Leu Ala Ser Gly Val Pro Ala Arg Phe Ser Gly Arg Gly
                        50                  55                  60

Ser Gly Thr Ser Tyr Ser Leu Thr Ile Ser Arg Met Glu Ala Glu Asp
         65                 70                  75                  80

Ala Ala Thr Tyr Tyr Cys Gln Gln Arg Asn Asn Tyr Pro Pro Trp Thr
                        85                  90                  95

Phe Gly Gly Gly Thr Lys Leu Glu Ile Lys
                        100                 105

<210> SEQ ID NO 38
<211> LENGTH: 106
<212> TYPE: PRT
<213> ORGANISM: Artificial Sequence
<220> FEATURE:
<223> OTHER INFORMATION: Antibody fragment

<400> SEQUENCE: 38

Ile Val Leu Thr Gln Ser Pro Ser Ile Met Ser Val Ser Pro Gly Glu
         1                  5                   10                  15

Lys Val Thr Ile Thr Cys Ser Ala Ser Ser Val Ser Tyr Met His
                        20                  25                  30

Trp Phe Gln Gln Lys Pro Gly Thr Ser Pro Lys Leu Gly Ile Tyr Ser
                        35                  40                  45

Thr Ser Asn Leu Ala Ser Gly Val Pro Ala Arg Phe Ser Gly Arg Gly
                        50                  55                  60

Ser Gly Thr Ser Tyr Ser Leu Thr Ile Ser Arg Val Ala Ala Glu Asp
         65                 70                  75                  80
```

```
Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105

<210> SEQ ID NO 39
<211> LENGTH: 106
<212> TYPE: PRT
<213> ORGANISM: Artificial Sequence
<220> FEATURE:
<223> OTHER INFORMATION: Antibody fragment

<400> SEQUENCE: 39

Ile Val Leu Thr Gln Ser Pro Ser Ile Met Ser Val Ser Pro Gly Glu
1               5                   10                  15

Lys Val Thr Ile Thr Cys Ser Ala Ser Ser Ser Val Ser Tyr Met His
            20                  25                  30

Trp Phe Gln Gln Lys Pro Gly Thr Ser Pro Lys Leu Ser Ile Tyr Ser
        35                  40                  45

Thr Ser Asn Leu Ala Ser Gly Val Pro Ala Arg Phe Ser Gly Arg Gly
    50                  55                  60

Ser Gly Thr Ser Tyr Ser Leu Thr Ile Ser Arg Val Ala Ala Glu Asp
65                  70                  75                  80

Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105

<210> SEQ ID NO 40
<211> LENGTH: 239
<212> TYPE: PRT
<213> ORGANISM: Artificial Sequence
<220> FEATURE:
<223> OTHER INFORMATION: mouse IgG VH-VL (kappa)

<400> SEQUENCE: 40

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
                100                 105                 110

Leu Thr Val Ser Ser Gly Gly Gly Ser Gly Gly Gly Gly Ser Gly
        115                 120                 125

Gly Gly Gly Ser Asp Ile Val Leu Thr Gln Ser Pro Ser Ile Met Ser
        130                 135                 140

Val Ser Pro Gly Glu Lys Val Thr Ile Thr Cys Ser Ala Ser Ser Ser
145                 150                 155                 160

Val Ser Tyr Met His Trp Phe Gln Gln Lys Pro Gly Ser Pro Lys
                165                 170                 175
```

Leu Ser Ile Tyr Ser Thr Ser Asn Leu Ala Ser Gly Val Pro Ala Arg
            180                 185                 190

Phe Ser Gly Arg Gly Ser Gly Thr Ser Tyr Ser Leu Thr Ile Ser Arg
            195                 200                 205

Val Ala Ala Glu Asp Ala Ala Thr Tyr Tyr Cys Gln Gln Arg Ser Asn
210                 215                 220

Tyr Pro Pro Trp Thr Phe Gly Gly Gly Thr Lys Leu Glu Ile Lys
225                 230                 235

<210> SEQ ID NO 41
<211> LENGTH: 15
<212> TYPE: PRT
<213> ORGANISM: Artificial Sequence
<220> FEATURE:
<223> OTHER INFORMATION: Linker

<400> SEQUENCE: 41

Gly Gly Gly Gly Ser Gly Gly Gly Ser Gly Gly Gly Gly Ser
1               5                   10                  15

<210> SEQ ID NO 42
<211> LENGTH: 19
<212> TYPE: PRT
<213> ORGANISM: Artificial Sequence
<220> FEATURE:
<223> OTHER INFORMATION: Signal peptide

<400> SEQUENCE: 42

Met Asp Trp Ile Trp Arg Ile Leu Phe Leu Val Gly Ala Ala Thr Gly
1               5                   10                  15

Ala His Ser

<210> SEQ ID NO 43
<211> LENGTH: 231
<212> TYPE: PRT
<213> ORGANISM: Artificial Sequence
<220> FEATURE:
<223> OTHER INFORMATION: human IgG1 Fc fragment

<400> SEQUENCE: 43

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp

```
                145                 150                 155                 160
Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
                210                 215                 220

Leu Ser Leu Ser Pro Gly Lys
225                 230

<210> SEQ ID NO 44
<211> LENGTH: 68
<212> TYPE: PRT
<213> ORGANISM: Artificial Sequence
<220> FEATURE:
<223> OTHER INFORMATION: human CD28 (TM + ic)

<400> SEQUENCE: 44

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
                35                  40                  45

Pro Thr Arg Lys His Tyr Gln Ala Tyr Ala Ala Ala Arg Asp Phe Ala
                50                  55                  60

Ala Tyr Arg Ser
65

<210> SEQ ID NO 45
<211> LENGTH: 113
<212> TYPE: PRT
<213> ORGANISM: Artificial Sequence
<220> FEATURE:
<223> OTHER INFORMATION: human CD3-zeta (ic)

<400> SEQUENCE: 45

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
                20                  25                  30

Tyr Asp Val Leu Asp Lys Arg Arg Gly Arg Asp Pro Glu Met Gly Gly
                35                  40                  45

Lys Pro Arg Arg Lys Asn Pro Gln Glu Gly Leu Tyr Asn Glu Leu Gln
                50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
                100                 105                 110

Arg

<210> SEQ ID NO 46
<211> LENGTH: 679
<212> TYPE: PRT
```

<213> ORGANISM: Artificial Sequence
<220> FEATURE:
<223> OTHER INFORMATION: Artificial T cell receptor

<400> SEQUENCE: 46

```
Met Asp Trp Ile Trp Arg Ile Leu Phe Leu Val Gly Ala Ala Thr Gly
1               5                   10                  15

Ala His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Asn Gly Gly Thr Ile Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Asp Tyr Gly Phe Val Leu Asp Tyr Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Gly Ser Asp Ile Val Leu Thr Gln Ser Pro Ser
145                 150                 155                 160

Ile Met Ser Val Ser Pro Gly Glu Lys Val Thr Ile Thr Cys Ser Ala
                165                 170                 175

Ser Ser Ser Val Ser Tyr Met His Trp Phe Gln Gln Lys Pro Gly Thr
            180                 185                 190

Ser Pro Lys Leu Ser Ile Tyr Ser Thr Ser Asn Leu Ala Ser Gly Val
        195                 200                 205

Pro Ala Arg Phe Ser Gly Arg Gly Ser Gly Thr Ser Tyr Ser Leu Thr
    210                 215                 220

Ile Ser Arg Val Ala Ala Glu Asp Ala Ala Thr Tyr Tyr Cys Gln Gln
225                 230                 235                 240

Arg Ser Asn Tyr Pro Pro Trp Thr Phe Gly Gly Gly Thr Lys Leu Glu
                245                 250                 255

Ile Lys Arg Ser Asp Pro Ala Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285

Leu Phe Pro Pro Lys Pro Lys Asp Thr Leu Met Ile Ala Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
```

-continued

```
385                 390                 395                 400
Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
                420                 425                 430

Gln Pro Glu Asn Asn Tyr Lys Thr Thr Pro Pro Val Leu Asp Ser Asp
                435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Lys Asp
                485                 490                 495

Pro Lys Phe Trp Val Leu Val Val Gly Gly Val Leu Ala Cys Tyr
                500                 505                 510

Ser Leu Leu Val Thr Val Ala Phe Ile Ile Phe Trp Val Arg Ser Lys
                515                 520                 525

Arg Ser Arg Leu Leu His Ser Asp Tyr Met Asn Met Thr Pro Arg Arg
    530                 535                 540

Pro Gly Pro Thr Arg Lys His Tyr Gln Ala Tyr Ala Ala Arg Asp
545                 550                 555                 560

Phe Ala Ala Tyr Arg Ser Leu Arg Val Lys Phe Ser Arg Ser Ala Asp
                565                 570                 575

Ala Pro Ala Tyr Gln Gln Gly Gln Asn Gln Leu Tyr Asn Glu Leu Asn
                580                 585                 590

Leu Gly Arg Arg Glu Glu Tyr Asp Val Leu Asp Lys Arg Arg Gly Arg
                595                 600                 605

Asp Pro Glu Met Gly Gly Lys Pro Arg Arg Lys Asn Pro Gln Glu Gly
                610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
                660                 665                 670

Met Gln Ala Leu Pro Pro Arg
                675
```

CLAUDIN-6-SPECIFIC IMMUNORECEPTORS AND T CELL EPITOPES

CROSS-REFERENCE TO RELATED PATENT APPLICATIONS

This application is a U.S. National Phase Application under 35 U.S.C. § 371 of International Patent Application No. PCT/EP2015/056899, filed Mar. 30, 2015, and claims the priority of PCT/EP2014/000868, filed Apr. 1, 2014 and PCT/EP2014/072864, filed Oct. 24, 2014, all of which are incorporated by reference in their entireties. The International Application was published on Oct. 8, 2015 as International Publication No. WO 2015/150327 A1.

TECHNICAL FIELD OF THE INVENTION

The present invention relates to the provision of Claudin-6-specific immunoreceptors (T cell receptors and artificial T cell receptors (chimeric antigen receptors; CARs)) and T cell epitopes which are useful for immunotherapy.

BACKGROUND OF THE INVENTION

The evolution of the immune system resulted in vertebrates in a highly effective network based on two types of defense: the innate and the adoptive immunity.

In contrast to the evolutionary ancient innate immune system that relies on invariant receptors recognizing common molecular patterns associated with pathogens, the adoptive immunity is based on highly specific antigen receptors on B cells (B lymphocytes) and T cells (T lymphocytes) and clonal selection.

While B cells raise humoral immune responses by secretion of antibodies, T cells mediate cellular immune responses leading to destruction of recognized cells.

T cells play a central role in cell-mediated immunity in humans and animals. The recognition and binding of a particular antigen is mediated by the T cell receptors (TCRs) expressed on the surface of T cells.

The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. To be able to target a vast variety of antigens, the T cell receptors need to have a great diversity.

This diversity is obtained by genetic rearrangement of different discontinuous segments of genes which code for the different structural regions of TCRs. TCRs are composed of one α-chain and one β-chain or of one γ-chain and one δ-chain. The TCR α/β chains are composed of an N-terminal highly polymorphic variable region involved in antigen recognition and an invariant constant region. On the genetic level, these chains are separated into several regions, a variable (V) region, a diversity (D) region (only β- and δ-chain), a joining (J) region and a constant (C) region. The human β-chain genes contain over 60 variable (V), 2 diversity (D), over 10 joining (J) segments, and 2 constant region segments (C). The human α-chain genes contain over 50 V segments, and over 60 J segments but no D segments, as well as one C segment. The murine β-chain genes contain over 30 variable (V), 2 diversity (D), over 10 joining (J) segments, and 2 constant region segments (C). The murine α-chain genes contain almost 100 V segments, 60 J segments, no D segments, but one C segment. During the differentiation of T cells, specific T cell receptor genes are created by rearranging one V, one D (only β- and δ-chain), one J and one C region gene. The diversity of the TCRs is further amplified by imprecise V-(D)-J rearrangement wherein random nucleotides are introduced and/or deleted at the recombination sites. Since the rearrangement of the TCR gene loci occurs in the genome during maturation of T cells, each mature T cell only expresses one specific α/β TCR or γ/δ TCR.

Figure 1:
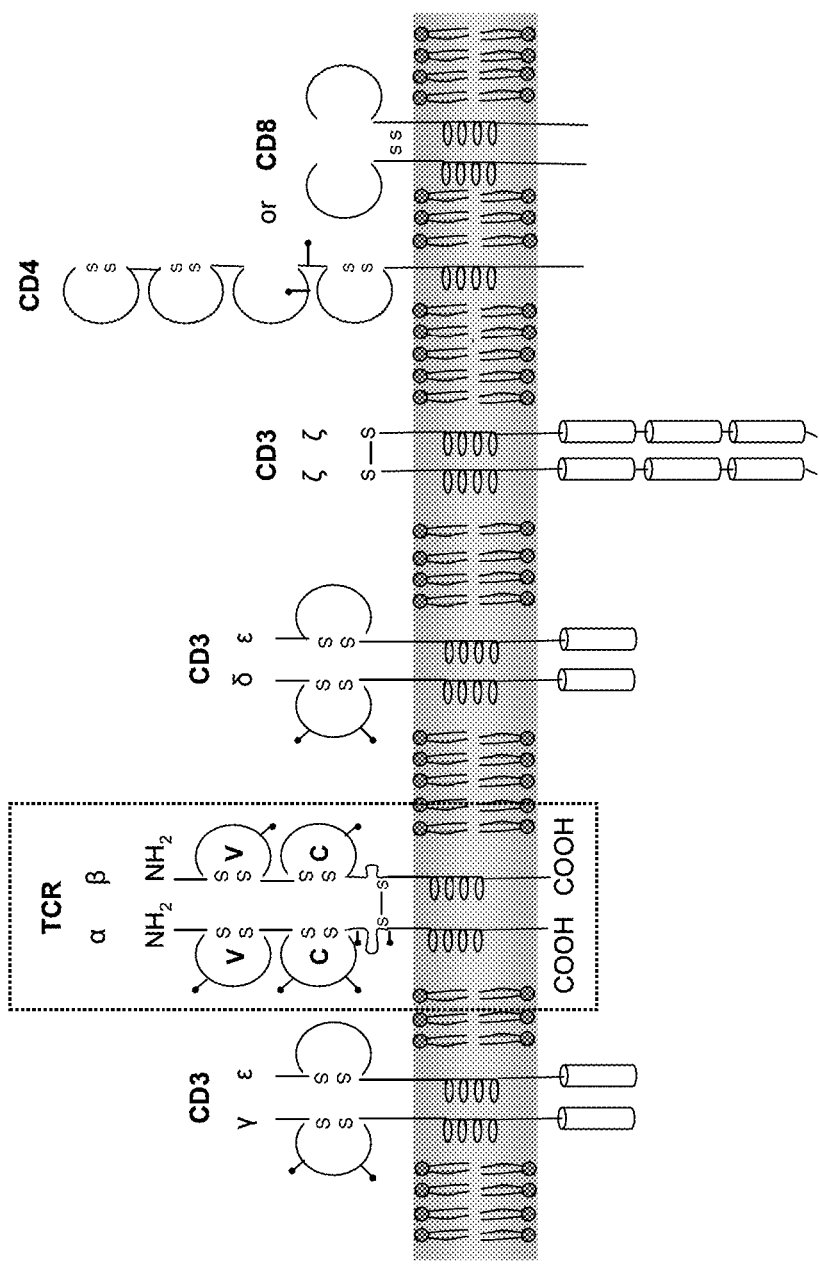

MHC and antigen binding is mediated by the complementary determining regions 1, 2 and 3 (CDR1, CDR2, CDR3) of the TCR. The CDR3 of the β-chain which is most critical for antigen recognition and binding is encoded by the V-D-J junction of the rearranged TCR β-chain gene. The TCR is a part of a complex signaling machinery, which includes the heterodimeric complex of the TCR α- and β-chains, the co-receptor CD4 or CD8 and the CD3 signal transduction module (FIG. 1). While the CD3 chains transfer the activation signal inside the cell, the TCR α/β heterodimer is solely responsible for antigen recognition. Thus, the transfer of the TCR α/β chains offers the opportunity to redirect T cells towards any antigen of interest.

Immunotherapy

Antigen-specific immunotherapy aims to enhance or induce specific immune responses in patients to control infectious or malignant diseases. The identification of a growing number of pathogen- and tumor-associated antigens (TAA) led to a broad collection of suitable targets for immunotherapy. Cells presenting immunogenic peptides (epitopes) derived from these antigens can be specifically targeted by either active or passive immunization strategies.

Active immunization tends to induce and expand antigen-specific T cells in the patient, which are able to specifically recognize and kill diseased cells. In contrast passive immunization relies on the adoptive transfer of T cells, which were expanded and optional genetically engineered in vitro (adoptive T cell therapy).

Vaccination

Tumor vaccines aim to induce endogenous tumor-specific immune responses by active immunization. Different antigen formats can be used for tumor vaccination including whole cancer cells, proteins, peptides or immunizing vectors such as RNA, DNA or viral vectors that can be applied either directly in vivo or in vitro by pulsing of DCs following transfer into the patient.

The number of clinical studies where therapy-induced immune responses can be identified is steadily increasing due to improvements of immunization strategies and methods for detection of antigen-specific immune responses (Connerotte, T. et al. (2008). Cancer Res. 68, 3931-3940; Schmitt, M. et al. (2008) Blood 111, 1357-1365; Speiser, D. E. et al. (2008) Proc. Natl. Acad. Sci. U.S.A 105, 3849-3854; Adams, S. et al. (2008) J. Immunol. 181, 776-784).

However, in most cases detected immune responses cannot systemically be correlated with clinical outcomes (Curigliano, G. et al. (2006) Ann. Oncol. 17, 750-762; Rosenberg, S. A. et al. (2004) Nat. Med. 10, 909-915).

The exact definition of peptide epitopes derived from tumor antigens may therefore contribute to improve specificity and efficiency of vaccination strategies as well as methods for immunomonitoring.

Adoptive Cell Transfer (ACT)

ACT based immunotherapy can be broadly defined as a form of passive immunization with previously sensitized T cells that are transferred to non-immune recipients or to the autologous host after ex vivo expansion from low precursor frequencies to clinically relevant cell numbers. Cell types that have been used for ACT experiments are lymphokine-activated killer (LAK) cells (Mule, J. J. et al. (1984) Science 225, 1487-1489; Rosenberg, S. A. et al. (1985) N. Engl. J. Med. 313, 1485-1492), tumor-infiltrating lymphocytes (TILs) (Rosenberg, S. A. et al. (1994) J. Natl. Cancer Inst. 86, 1159-1166), donor lymphocytes after hematopoietic stem cell transplantation (HSCT) as well as tumor-specific T cell lines or clones (Dudley, M. E. et al. (2001) J. Immunother. 24, 363-373; Yee, C. et al. (2002) Proc. Natl. Acad. Sci. U.S.A 99, 16168-16173). Adoptive T cell transfer was shown to have therapeutic activity against human viral infections such as CMV. While CMV infection and reactivation of endogenous latent viruses is controlled by the immune system in healthy individuals, it results in significant morbidity and mortality in immune compromised individuals such as transplant recipients or AIDS patients.

Riddell and co-workers demonstrated the reconstitution of viral immunity by adoptive T cell therapy in immune suppressed patients after transfer of CD8+ CMV-specific T cell clones derived from HLA-matched CMV-seropositive transplant donors (Riddell, S. R. (1992) Science 257, 238-241).

As an alternative approach polyclonal donor-derived CMV- or EBV-specific T cell populations were transferred to transplant recipients resulting in increased persistence of transferred T cells (Rooney, C. M. et al. (1998) Blood 92, 1549-1555; Peggs, K. S. et al. (2003) Lancet 362, 1375-1377).

For adoptive immunotherapy of melanoma Rosenberg and co-workers established an ACT approach relying on the infusion of in vitro expanded autologous tumor-infiltrating lymphocytes (TILs) isolated from excised tumors in combination with a non-myeloablative lymphodepleting chemotherapy and high-dose IL2. A recently published clinical study resulted in an objective response rate of ~50% of treated patients suffering from metastatic melanoma (Dudley, M. E. et al. (2005) J. Clin. Oncol. 23: 2346-2357).

However, patients must fulfill several premises to be eligible for ACT immunotherapy. They must have resectable tumors. The tumors must generate viable TILs under cell culture conditions. The TILs must be reactive against tumor antigens, and must expand in vitro to sufficient numbers. Especially in other cancers than melanoma, it is difficult to obtain such tumor-reactive TILs. Furthermore, repeated in vitro stimulation and clonal expansion of normal human T lymphocytes results in progressive decrease in telomerase activity and shortening of telomeres resulting in replicative senescence and decreased potential for persistence of transferred T cells (Shen, X. et al. (2007) J. Immunother. 30: 123-129).

ACT Using Gene-Engineered T Cells

An approach overcoming the limitations of ACT is the adoptive transfer of autologous T cells reprogrammed to express a tumor-reactive immunoreceptor of defined specificity during short-time ex vivo culture followed by reinfusion into the patient (Kershaw M. H. et al. (2013) Nature Reviews Cancer 13 (8):525-41). This strategy makes ACT applicable to a variety of common malignancies even if tumor-reactive T cells are absent in the patient. Since the antigenic specificity of T cells is rested entirely on the heterodimeric complex of the TCR α- and β-chain, the transfer of cloned TCR genes into T cells offers the potential to redirect them towards any antigen of interest. Therefore, TCR gene therapy provides an attractive strategy to develop antigen-specific immunotherapy with autologous lymphocytes as treatment option. Major advantages of TCR gene transfer are the creation of therapeutic quantities of antigen-specific T cells within a few days and the possibility to introduce specificities that are not present in the endogenous TCR repertoire of the patient.

Several groups demonstrated, that TCR gene transfer is an attractive strategy to redirect antigen-specificity of primary T cells (Morgan, R. A. et al. (2003) J. Immunol. 171, 3287-3295; Cooper, L. J. et al. (2000) J. Viral. 74, 8207-8212; Fujio, K. et al. (2000) J. Immunol. 165, 528-532; Kessels, H. W. et al. (2001) Nat. Immunol. 2, 957-961; Dembic, Z. et al. (1986) Nature 320, 232-238).

Feasibility of TCR gene therapy in humans was recently demonstrated in clinical trials for the treatment of malignant melanoma by Rosenberg and his group. The adoptive transfer of autologous lymphocytes retrovirally transduced with melanoma/melanocyte antigen-specific TCRs resulted in cancer regression in up to 30% of treated melanoma patients (Morgan, R. A. et al. (2006) Science 314, 126-129; Johnson, L. A. et al. (2009) Blood 114, 535-546).

Chimeric Antigen Receptors

Chimeric antigen receptors (CARs) are engineered receptors that combine a single chain variable fragment (scFv) of a monoclonal antibody with an intracellular part consisting of one or more signaling domains for T cell activation. CARs recognize native antigens in a non-MHC-restricted manner and can therefore be used in all individuals no matter what their HLA type is and they are functional in CD4+ as well as CD8+ T cells.

Figure 2:
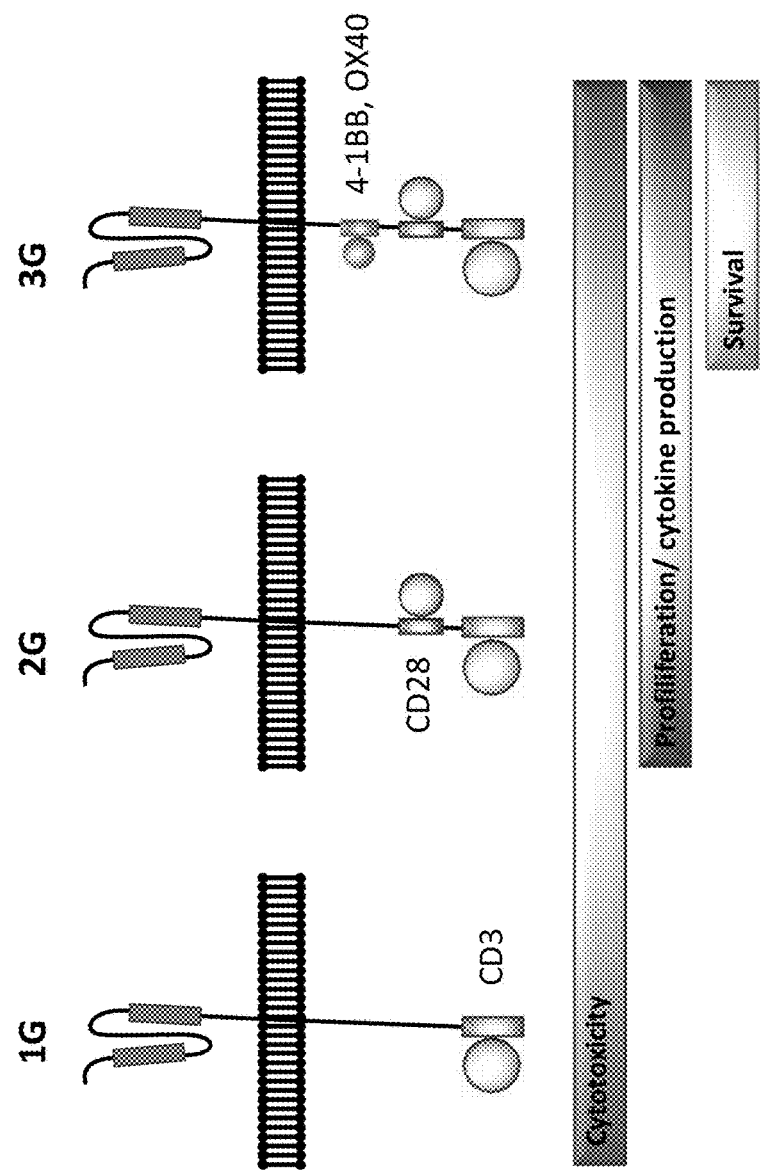

A multitude of CARs has been reported over the past decade, targeting a panel of different cell surface tumor antigens. Their biologic functions were dramatically improved by incorporation of a costimulatory domain resulting in tripartite receptors (scFv, CD28, CD3ζ), termed 2nd generation CARs. CARs of the 3rd generation encompass additional domains of costimulatory molecules such as OX40 and 4-1BB to enhance the proliferative capacity and persistence of modified T-cells (FIG. 2).

Target Structures for Antigen-Specific Immunotherapy

The discovery of multiple tumor-associated antigens (TAAs) has provided the basis for antigen-specific immunotherapy concepts (Novellino, L. et al. (2005) Cancer Immunol. Immunother. 54, 187-207). TAAs are unusual proteins expressed on tumor cells due to their genetic instability, which have no or limited expression in normal cells. These TAAs can lead to specific recognition of malignant cells by the immune system.

Molecular cloning of TAAs by screening of tumor-derived cDNA expression libraries using autologous tumor-specific T cells (van der Bruggen, P. et al. (1991) Science 254, 1643-1647) or circulating antibodies (Sahin, U. et al. (1995) Proc. Natl. Acad. Sci. U.S.A 92, 11810-11813), reverse immunology approaches, biochemical methods (Hunt, D. F. et al. (1992) Science 256, 1817-1820), gene expression analyses or in silico cloning strategies (Helftenbein, G. et al. (2008) Gene 414, 76-84) led to a significant number of target candidates for immunotherapeutic strategies. TAAs fall in several categories, including differentiation antigens, overexpressed antigens, tumor-specific splice variants, mutated gene products, viral and cancer testis antigens (CTAs). The cancer testis family is a very promising category of TAAs as their expression is restricted to the testis and a multitude of different tumor entities (Scanlan, M. J. et al. (2002) Immunol. Rev. 188, 22-32). Until now more than 50 CT genes have been described (Scanlan, M. J. et al. (2004) Cancer Immun. 4, 1) and some of them have been addressed in clinical studies (Adams, S. et al. (2008) J. Immunol. 181, 776-784; Atanackovic, D. et al. (2004) J.

Immunol. 172, 3289-3296; Chen, Q. et al. (2004) Proc. Natl. Acad. Sci. U.S.A 101, 9363-9368; Connerotte, T. et al. (2008). Cancer Res. 68, 3931-3940; Davis, I. D. et al. (2004) Proc. Natl. Acad. Sci. U.S.A 101, 10697-10702; Jager, E. (2000) Proc. Natl. Acad. Sci. U.S.A 97, 12198-12203; Marchand, M. et al. (1999) Int. J. Cancer 80, 219-230; Schuler-Thurner, B. et al. (2000) J. Immunol. 165, 3492-3496).

In spite of the growing number of attractive target structures for immunotherapeutic approaches specific T cell clones or lines of defined HLA restriction do only exist for a few of them (Chaux, P. et al. (1999) J. Immunol. 163, 2928-2936; Zhang, Y. et al. (2002) Tissue Antigens 60, 365-371; Zhao, Y. et al. (2005) J. Immunol. 174, 4415-4423).

Figure 4:
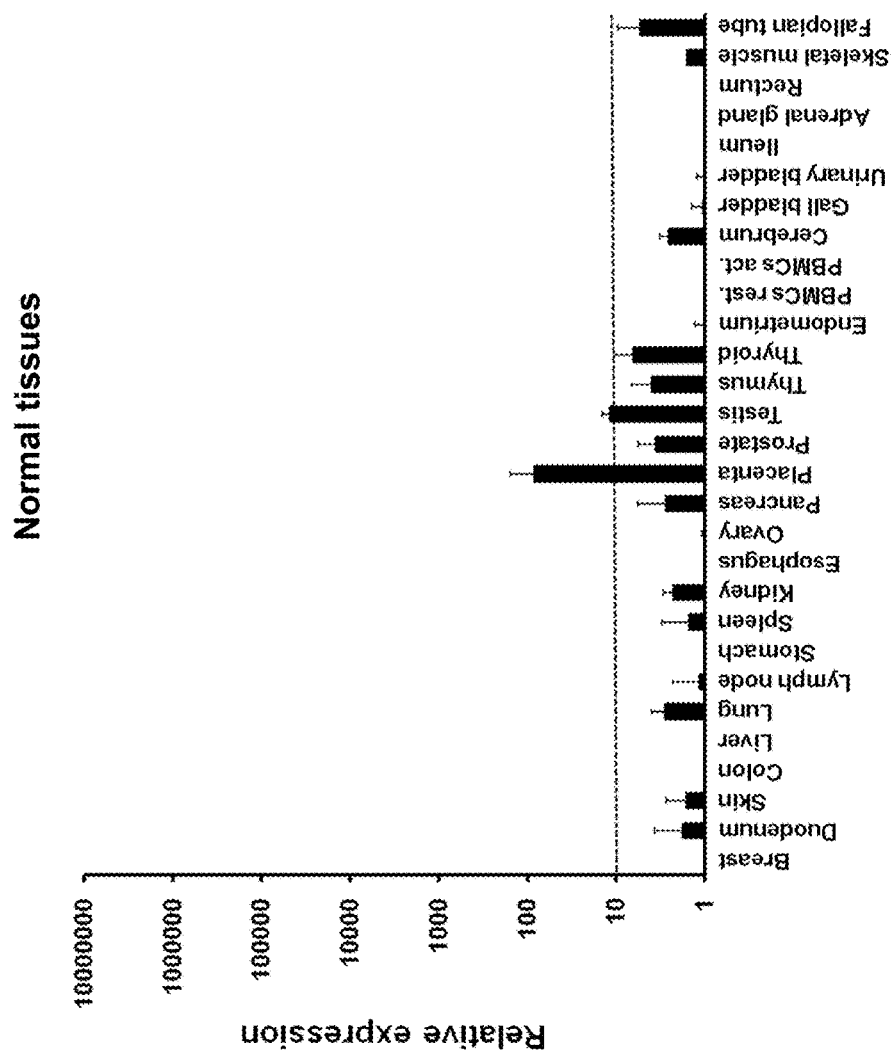
Figure 4:
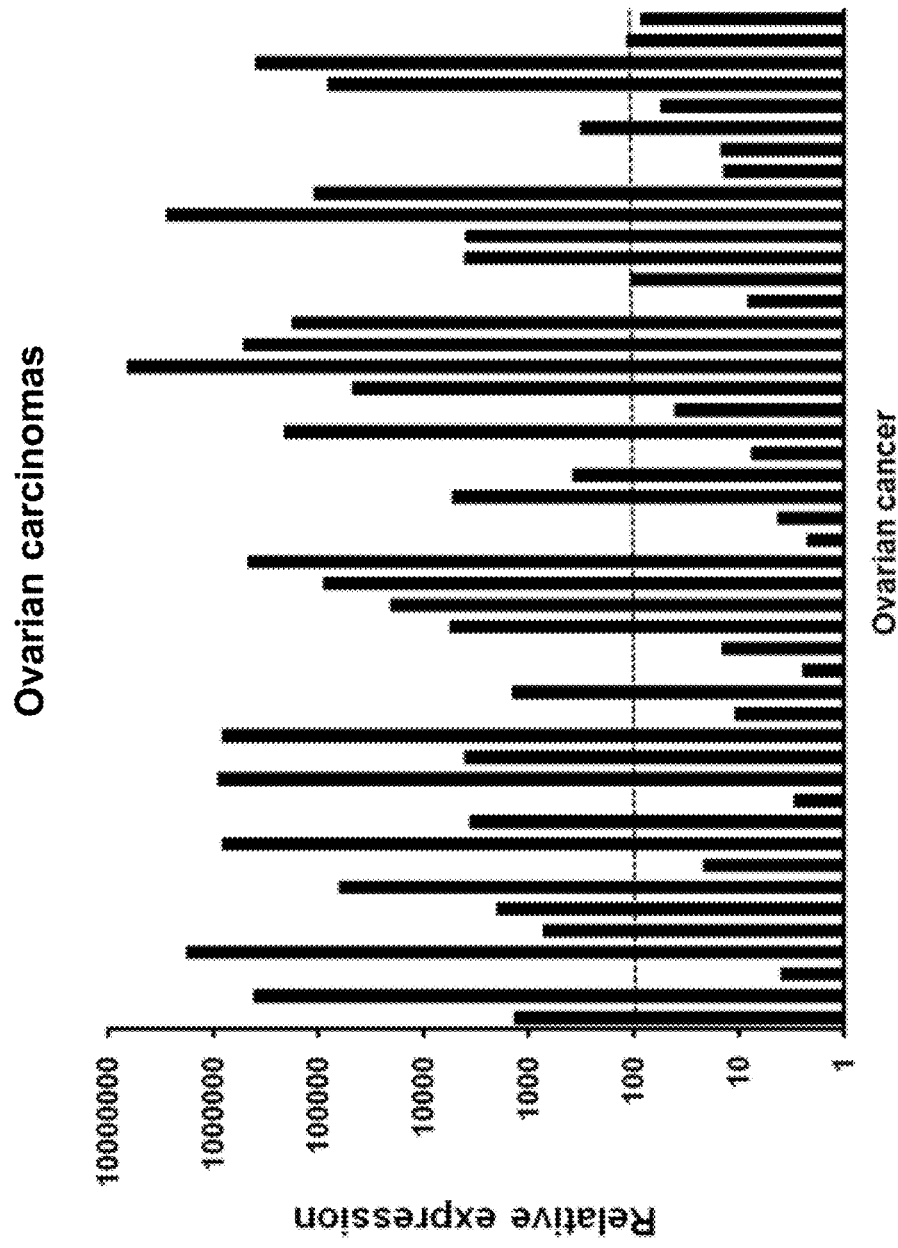

Claudins are integral membrane proteins located within the tight junctions of epithelia and endothelia. Claudins are predicted to have four transmembrane segments with two extracellular loops, and N- and C-termini located in the cytoplasm. The Claudin (CLDN) family of transmembrane proteins plays a critical role in the maintenance of epithelial and endothelial tight junctions and might also play a role in the maintenance of the cytoskeleton and in cell signalling. Claudin-6 (CLDN6) is an oncofetal gene expressed in murine and human stem cells as well as embryoid bodies committed to the epithelia cell fate (Turksen, K. et al. (2001) Dev Dyn 222, 292-300; Anderson W J. et al. (2008) Dev Dyn 237, 504-12; Turksen K. et al. (2002) Development, 129, 1775-84; Assou S. et al. (2007) Stem Cells 25, 961-73). As a tumor-associated antigen it can be classified as a differentiation antigen due to its expression during early stage of epidermal morphogenesis where it is crucial for epidermal differentiation and barrier formation. Additionally expression was observed in epithelial tissues or neonatal normal epithelial tissue of tongue, skin, stomach and breast (Abuazza G. et al. (2006), Am J Physiol Renal Physiol 291, 1132-1141; Troy T. C. et al. (2007), Molecular Biotechnology 36, 166-74; Zhao L. et al. (2008), Am J Physiol Regul Integr Comp Physiol 294, 1856-1862). Besides that, own data also reveal low or very low expression of CLDN6 in human placenta, urinary bladder, endometrium, prostate and the peripheral nerve and frequent overexpression of CLDN6 in different cancers. CLDN6 has been demonstrated to be overexpressed in tumors, including pediatric brain tumors, gastric adenocarcinomas and germ cell tumors as well as visceral carcinomas such as ovarian carcinomas (FIG. 4). It has also been demonstrated that overexpression of CLDN6 in gastric cancer cells results in increased invasiveness, migration and proliferation suggesting that CLDN6 is a marker for poor prognosis and may play a potential role in maintaining the malignant phenotype. In addition, it has been shown that CLDN6 functions as cancer suppressor via inhibition of cell proliferation and induction of apoptosis in breast cancer cell lines.

The frequent overexpression of CLDN6 on tumors qualifies this molecule as a highly attractive target for development of therapeutics directed against CLDN6 such as vaccine therapeutics and therapeutic antibodies. However, hitherto no HLA-A*2-restricted CLDN6 T cell epitopes and T cell receptors targeting CLDN6 have been described and it is unknown whether CLDN6 expressing cancer cells can be targeted in vivo by immunotherapies involving T cells using active or passive immunization approaches.

DESCRIPTION OF INVENTION

Summary of the Invention

The present invention relates to T cell receptors and artificial T cell receptors specific for the tumor-associated antigen CLDN6, in particular when present on the surface of a cell such as a diseased cell or presented on the surface of a cell such as a diseased cell or an antigen-presenting cell, as well as peptides comprising epitopes recognized by these T cell receptors, i.e. CLDN6-T cell epitopes.

By adoptive transfer of T cells engineered to express such T cell receptor or artificial T cell receptor CLDN6 expressing cancer cells can be specifically targeted thereby leading to selective destruction of cancer cells. Furthermore, the T cell epitopes provided according to the invention are useful for designing vaccines against CLDN6-expressing cancers.

In one aspect, the invention relates to a peptide comprising an amino acid sequence selected from the group consisting of SEQ ID NOs: 3, 4 and 5 or a variant of said amino acid sequence. In one embodiment the peptide is 100 or less, 50 or less, 20 or less, or 10 or less amino acids long. In one embodiment, the peptide can be processed to produce a peptide consisting of the amino acid sequence selected from the group consisting of SEQ ID NOs: 3, 4 and 5 or a variant of said amino acid sequence. In one embodiment, the peptide consists of the amino acid sequence selected from the group consisting of SEQ ID NOs: 3, 4 and 5 or a variant of said amino acid sequence.

In one embodiment, the peptide is a MHC class I or class II presented peptide, preferably a MHC class I presented peptide, or, if present within cells, can be processed to produce a procession product thereof which is a MHC class I or class II presented peptide, preferably a MHC class I presented peptide. Preferably, said MHC class I or class II presented peptide has a sequence substantially corresponding to the given amino acid sequence, i.e. an amino acid sequence selected from the group consisting of SEQ ID NOs: 3, 4 and 5 or a variant of said amino acid sequence. Preferably, a peptide according to the invention is capable of stimulating a cellular response against a disease involving cells characterized by presentation of CLDN6 with class I MHC.

In further aspects, the invention relates to a nucleic acid comprising a nucleotide sequence encoding the peptide of the invention and a cell comprising the nucleic acid. The nucleic acid may be a recombinant nucleic acid. The nucleic acid may be present in a plasmid or an expression vector and may be functionally linked to a promoter. In one embodiment, the nucleic acid is RNA. Preferably, the cell expresses the peptide. The cell may be a recombinant cell and may secrete the encoded peptide or a procession product thereof, may express it on the surface and preferably may additionally express an MHC molecule which binds to said peptide or a procession product thereof and preferably presents said peptide or a procession product thereof on the cell surface. In one embodiment, the cell expresses the MHC molecule endogenously. In a further embodiment, the cell expresses the MHC molecule and/or the peptide in a recombinant manner. The cell is preferably nonproliferative. In a preferred embodiment, the cell is an antigen-presenting cell, in particular a dendritic cell, a monocyte or a macrophage.

In a further aspect, the invention relates to a cell that presents the peptide of the invention or a procession product thereof, wherein the procession product preferably is a peptide having the given amino acid sequence, i.e. an amino acid sequence selected from the group consisting of SEQ ID NOs: 3, 4 and 5 or a variant of said amino acid sequence. In one embodiment, said cell is a cell comprising a nucleic acid comprising a nucleotide sequence encoding the peptide of the invention. Preferably said cell expresses said nucleic acid so as to produce said peptide. Optionally said cell processes said peptide so as to produce a peptide consisting of an amino acid sequence selected from the group consisting of SEQ ID NOs: 3, 4 and 5 or a variant of said amino acid sequence. The cell may present the peptide or a procession product thereof by MHC molecules on its surface. In one embodiment, the cell endogenously expresses an MHC molecule. In a further embodiment, the cell recombinantly expresses an MHC molecule. In one embodiment, the MHC molecules of the cell are loaded (pulsed) with the peptide by addition of the peptide to the cell. The cell may recombinantly express the peptide and present said peptide or a procession product thereof on the cell surface. The cell is preferably nonproliferative. In a preferred embodiment, the cell is an antigen-presenting cell such as a dendritic cell, a monocyte or a macrophage.

In a further aspect, the invention relates to an immunoreactive cell which is reactive with a peptide of the invention, in particular when presented on the surface of a cell such as a diseased cell. The immunoreactive cell may be a cell that has been sensitized in vitro to recognize the peptide. The immunoreactive cell may be a T cell, preferably a cytotoxic T cell. Preferably, the immunoreactive cell binds to a sequence substantially corresponding to the given amino acid sequence, i.e. an amino acid sequence selected from the group consisting of SEQ ID NOs: 3, 4 and 5 or a variant of said amino acid sequence, in particular when bound to MHC such as MHC on the surface of a cell such as a diseased cell.

In a further aspect, the invention relates to a binding agent which binds to a peptide of the invention, optionally in a complex with an MHC molecule.

In a further aspect, the invention relates to a T cell receptor which binds to a peptide of the invention, optionally in a complex with an MHC molecule, and preferably is reactive with said peptide, or a polypeptide chain of said T cell receptor. In one embodiment, the polypeptide chain of said T cell receptor is a T cell receptor α-chain or T cell receptor β-chain.

In a further aspect, the invention relates to a T cell receptor α-chain or a T cell receptor comprising said T cell receptor α-chain,
wherein said T cell receptor α-chain is selected from the group consisting of:
(i) a T cell receptor α-chain comprising at least one, preferably two, more preferably all three of the CDR sequences of a T cell receptor α-chain selected from the group consisting of SEQ ID NOs: 6, 8, 10, 12, 14, 16, 18, 20, 22, 24, 26 and 28 or a variant thereof and
(ii) a T cell receptor α-chain comprising a T cell receptor α-chain sequence selected from the group consisting of SEQ ID NOs: 6, 8, 10, 12, 14, 16, 18, 20, 22, 24, 26 and 28 or a fragment thereof, or a variant of said sequence or fragment.

In one embodiment, said SEQ ID NOs: are selected from the group consisting of SEQ ID NOs: 6, 8, 10, 12, 14 and 16 and said T cell receptor is reactive with a peptide comprising the amino acid sequence of SEQ ID NO: 3 or a variant of said amino acid sequence.

In one embodiment, said SEQ ID NOs: are selected from the group consisting of SEQ ID NOs: 18, 20, 22, 24 and 26 and said T cell receptor is reactive with a peptide comprising the amino acid sequence of SEQ ID NO: 4 or a variant of said amino acid sequence.

In one embodiment, said SEQ ID NO: is SEQ ID NO: 28 and said T cell receptor is reactive with a peptide comprising the amino acid sequence of SEQ ID NO: 5 or a variant of said amino acid sequence.

In a further aspect, the invention relates to a T cell receptor β-chain or a T cell receptor comprising said T cell receptor β-chain,
wherein said T cell receptor β-chain is selected from the group consisting of:
(i) a T cell receptor β-chain comprising at least one, preferably two, more preferably all three of the CDR sequences of a T cell receptor β-chain selected from the group consisting of SEQ ID NOs: 7, 9, 11, 13, 15, 17, 19, 21, 23, 25, 27 and 29 or a variant thereof and
(ii) a T cell receptor β-chain comprising a T cell receptor β-chain sequence selected from the group consisting of SEQ ID NOs: 7, 9, 11, 13, 15, 17, 19, 21, 23, 25, 27 and 29 or a fragment thereof, or a variant of said sequence or fragment.

In one embodiment, said SEQ ID NOs: are selected from the group consisting of SEQ ID NOs: 7, 9, 11, 13, 15 and 17 and said T cell receptor is reactive with a peptide comprising the amino acid sequence of SEQ ID NO: 3 or a variant of said amino acid sequence.

In one embodiment, said SEQ ID NOs: are selected from the group consisting of SEQ ID NOs: 19, 21, 23, 25 and 27 and said T cell receptor is reactive with a peptide comprising the amino acid sequence of SEQ ID NO: 4 or a variant of said amino acid sequence.

In one embodiment, said SEQ ID NO: is SEQ ID NO: 29 and said T cell receptor is reactive with a peptide comprising the amino acid sequence of SEQ ID NO: 5 or a variant of said amino acid sequence.

In a further aspect, the invention relates to a T cell receptor selected from the group consisting of:
(I) a T cell receptor comprising:
(i) a T cell receptor α-chain comprising at least one, preferably two, more preferably all three of the CDR sequences of the T cell receptor α-chain of SEQ ID NO: x or a variant thereof, and
(ii) a T cell receptor β-chain comprising at least one, preferably two, more preferably all three of the CDR sequences of a T cell receptor β-chain of SEQ ID NO: x+1 or a variant thereof;
wherein x selected from the group consisting of 6, 8, 10, 12, 14, 16, 18, 20, 22, 24, 26 and 28 and
(II) a T cell receptor comprising:
(i) a T cell receptor α-chain comprising the T cell receptor α-chain sequence of SEQ ID NO: x or a fragment thereof, or a variant of said sequence or fragment, and
(ii) a T cell receptor β-chain comprising the T cell receptor β-chain sequence of SEQ ID NO: x+1 or a fragment thereof, or a variant of said sequence or fragment;
wherein x selected from the group consisting of 6, 8, 10, 12, 14, 16, 18, 20, 22, 24, 26 and 28.

In one embodiment, said x is selected from the group consisting of 6, 8, 10, 12, 14 and 16 and said T cell receptor is reactive with a peptide comprising the amino acid sequence of SEQ ID NO: 3 or a variant of said amino acid sequence.

In one embodiment, said x is selected from the group consisting of 18, 20, 22, 24 and 26 and said T cell receptor is reactive with a peptide comprising the amino acid sequence of SEQ ID NO: 4 or a variant of said amino acid sequence.

In one embodiment, said x is 28 and said T cell receptor is reactive with a peptide comprising the amino acid sequence of SEQ ID NO: 5 or a variant of said amino acid sequence.

In one embodiment, binding of said T cell receptor when expressed by T cells and/or present on T cells to CLDN6-peptide epitopes as described above presented on cells such as cancer cells results in proliferation and/or activation of said T cells, wherein said activated T cells preferably release cytotoxic factors, e.g. perforins and granzymes, and initiate cytolysis and/or apoptosis of cancer cells.

In a further aspect, the invention relates to an artificial T cell receptor which binds to claudin-6 (CLDN6). In one embodiment, binding is a specific binding.

In one embodiment, said CLDN6 is expressed in a cancer cell. In one embodiment said CLDN6 is expressed on the surface of a cancer cell. In one embodiment said artificial T cell receptor binds to an extracellular domain or to an epitope in an extracellular domain of CLDN6. In one embodiment said artificial T cell receptor binds to native epitopes of CLDN6 present on the surface of living cells. In one embodiment said artificial T cell receptor binds to the first extracellular loop of CLDN6. In one embodiment, binding of said artificial T cell receptor when expressed by T cells and/or present on T cells to CLDN6 present on cells such as cancer cells results in proliferation and/or activation of said T cells, wherein said activated T cells preferably release cytotoxic factors, e.g. perforins and granzymes, and initiate cytolysis and/or apoptosis of cancer cells.

In one embodiment, the artificial T cell receptor of the invention comprises a binding domain for CLDN6. In one embodiment, the binding domain for CLDN6 is comprised by an exodomain of said artificial T cell receptor. In one embodiment, the binding domain for CLDN6 comprises a single-chain variable fragment (scFv) of a CLDN6 antibody. In one embodiment, the binding domain for CLDN6 comprises a variable region of a heavy chain of an immunoglobulin (VH) with a specificity for CLDN6 (VH(CLDN6)) and a variable region of a light chain of an immunoglobulin (VL) with a specificity for CLDN6 (VL(CLDN6)). In one embodiment, said heavy chain variable region (VH) and the corresponding light chain variable region (VL) are connected via a peptide linker, preferably a peptide linker comprising the amino acid sequence (GGGGS)3. In one embodiment, the binding domain for CLDN6 comprises a VH(CLDN6) comprising an amino acid sequence represented by SEQ ID NO: 32 or a fragment thereof, or a variant of said amino acid sequence or fragment. In one embodiment, the binding domain for CLDN6 comprises a VL(CLDN6) comprising an amino acid sequence represented by SEQ ID NO: 33, 38 or 39 or a fragment thereof, or a variant of said amino acid sequence or fragment. In one embodiment, the binding domain for CLDN6 comprises a VH(CLDN6) comprising an amino acid sequence represented by SEQ ID NO: 32 or a fragment thereof, or a variant of said amino acid sequence or fragment and a VL(CLDN6) comprising an amino acid sequence represented by SEQ ID NO: 39 or a fragment thereof, or a variant of said amino acid sequence or fragment. In one embodiment, the binding domain for CLDN6 comprises an amino acid sequence represented by SEQ ID NO: 40 or a fragment thereof, or a variant of said amino acid sequence or fragment.

In one embodiment, the artificial T cell receptor of the invention comprises a transmembrane domain. In one embodiment, the transmembrane domain is a hydrophobic alpha helix that spans the membrane. In one embodiment, the transmembrane domain comprises the CD28 transmembrane domain or a fragment thereof.

In one embodiment, the artificial T cell receptor of the invention comprises a T cell signaling domain. In one embodiment, the T cell signaling domain is located intracellularly. In one embodiment, the T cell signaling domain comprises CD3-zeta, preferably the endodomain of CD3-zeta, optionally in combination with CD28. In one embodiment, the T cell signaling domain comprises the sequence according to SEQ ID NO: 45 or a fragment thereof, or a variant of said sequence or fragment.

In one embodiment, the artificial T cell receptor of the invention comprises a signal peptide which directs the nascent protein into the endoplasmic reticulum. In one embodiment, the signal peptide precedes the binding domain for CLDN6. In one embodiment, the signal peptide comprises the sequence according to SEQ ID NO: 42 or a fragment thereof, or a variant of said sequence or fragment.

In one embodiment, the artificial T cell receptor of the invention comprises a spacer region which links the binding domain for CLDN6 to the transmembrane domain. In one embodiment, the spacer region allows the binding domain for CLDN6 to orient in different directions to facilitate CLDN6 recognition. In one embodiment, the spacer region comprises the hinge region from IgG1. In one embodiment, the spacer region comprises the sequence according to SEQ ID NO: 43 or a fragment thereof, or a variant of said sequence or fragment.

In one embodiment, the artificial T cell receptor of the invention comprises the structure:

NH2-signal peptide-binding domain for CLDN6-spacer region-transmembrane domain-T cell signaling domain-COOH.

In one embodiment, the artificial T cell receptor of the invention comprises the amino acid sequence according to SEQ ID NO: 46 or a fragment thereof, or a variant of said amino acid sequence or fragment.

The above T cell receptors and artificial T cell receptors are preferably specific for the tumor-associated antigen CLDN6, in particular when present on the surface of a cell such as a diseased cell or when presented on the surface of a cell such as a diseased cell or an antigen-presenting cell.

The T cell receptors and artificial T cell receptors of the invention may be expressed by and/or present on the surface of cells such as T cells.

In a further aspect, the invention relates to a nucleic acid comprising a nucleotide sequence encoding the T cell receptor chain or T cell receptor of the invention or encoding the artificial T cell receptor of the invention. In one embodiment, the nucleic acid is a recombinant nucleic acid. In one embodiment, the nucleic acid is in the form of a vector or in the form of RNA.

In a further aspect, the invention relates to a cell comprising the T cell receptor chain or T cell receptor of the invention or the artificial T cell receptor of the invention and/or comprising a nucleic acid comprising a nucleotide sequence encoding the T cell receptor chain or T cell receptor of the invention or encoding the artificial T cell receptor of the invention. In one embodiment, said nucleic acid is RNA, preferably in vitro transcribed RNA. The cell may be a cell expressing the T cell receptor chain or T cell receptor of the invention or the artificial T cell receptor of the invention and/or may have the T cell receptor chain or T cell receptor of the invention or the artificial T cell receptor of the invention on its cell surface. In one embodiment, said cell is a cell which is useful for adoptive cell transfer. The cell may be an effector or stem cell, preferably an immunoreactive cell. The immunoreactive cell may be a T cell, preferably a cytotoxic T cell. In one embodiment, the immunoreactive cell is reactive with the tumor-associated antigen CLDN6. In one embodiment, said CLDN6 is present on the surface of a cell such as a diseased cell. In one embodiment, said CLDN6 is presented on the surface of a cell such as a diseased cell or an antigen-presenting cell, and the immunoreactive cell is reactive with a peptide of the invention, in particular when presented in the context of MHC, and preferably binds to a sequence substantially corresponding to the given amino acid sequence, i.e. an amino acid sequence selected from the group consisting of SEQ ID NOs: 3, 4 and 5 or a variant of said amino acid sequence. In one embodiment, said cell lacks surface expression of an endogenous TCR or is specific for a CLDN6-unrelated antigen.

In one embodiment, cells of the invention prior to use in adoptive cell transfer are subjected to an antigen-specific expansion and rechallenge, wherein the antigen-specific expansion and rechallenge may be effected by exposing the cells to preferably autologous antigen presenting cells presenting CLDN6 or a peptide fragment thereof.

In a further aspect, the invention relates to a method of producing an immunoreactive cell comprising the step of transducing a T cell with a nucleic acid comprising a nucleotide sequence encoding the T cell receptor chain or T cell receptor of the invention or encoding the artificial T cell receptor of the invention.

Furthermore, the present invention generally embraces the treatment of diseases by targeting diseased cells such as cancer cells, in particular cancer cells expressing CLDN6. The methods provide for the selective eradication of cells that express on their surface and/or present the tumor-associated antigen CLDN6, thereby minimizing adverse effects to normal cells not expressing and/or presenting CLDN6. Thus, preferred diseases for a therapy are those in which CLDN6 is expressed and optionally presented such as cancer diseases, in particular those described herein.

When a peptide of the invention, a nucleic acid comprising a nucleotide sequence encoding the peptide of the invention or a cell of the invention comprising said nucleic acid is administered, the treatment preferably involves an active immunization. Preferably, CLDN6-specific T cells are expanded in the patient, which are able to recognize and kill diseased cells. When an immunoreactive cell of the invention, a T cell receptor of the invention, an artificial T cell receptor of the invention, a nucleic acid of the invention comprising a nucleotide sequence encoding a T cell receptor of the invention or encoding an artificial T cell receptor of the invention or a cell of the invention comprising a T cell receptor or an artificial T cell receptor of the invention and/or comprising a nucleic acid of the invention comprising a nucleotide sequence encoding a T cell receptor of the invention or encoding an artificial T cell receptor of the invention is administered, the treatment preferably involves a passive immunization. Preferably, CLDN6-specific T cells which are able to recognize and kill diseased cells and which were optionally genetically engineered and/or expanded in vitro are adoptively transferred to a patient.

In one aspect, the invention relates to a pharmaceutical composition comprising one or more of:
(i) the peptide of the invention;
(ii) the nucleic acid of the invention;
(iii) the cell of the invention;
(iv) the immunoreactive cell of the invention;
(v) the binding agent of the invention;
(vi) the T cell receptor of the invention; and
(vi) the artificial T cell receptor of the invention.

A pharmaceutical composition of the invention may comprise a pharmaceutically acceptable carrier and may optionally comprise one or more adjuvants, stabilizers etc. The pharmaceutical composition may in the form of a therapeutic or prophylactic vaccine. In one embodiment, the pharmaceutical composition is for use in treating or preventing a cancer disease such as those described herein.

Administration of a pharmaceutical composition as described above may provide MHC class II-presented epitopes that are capable of eliciting a CD4+ helper T cell response and/or a CD8+ T cell response against CLDN6 (including cells expressing CLDN6 on their surface and/or presenting CLDN6 in the context of MHC molecules). Alternatively or additionally, administration of a pharmaceutical composition as described above may provide MHC class I-presented epitopes that are capable of eliciting a CD8+ T cell response against CLDN6.

In a further aspect, the invention relates to a method of treating or preventing a cancer disease comprising administering to a patient the pharmaceutical composition of the invention.

In a further aspect, the invention relates to the peptide of the invention, the nucleic acid of the invention, the cell of the invention, the immunoreactive cell of the invention, the binding agent of the invention, the T cell receptor of the invention, or the artificial T cell receptor of the invention for use in therapy, in particular for use in treating or preventing cancer.

Another aspect relates to a method for inducing an immune response in a subject, comprising administering to the subject a pharmaceutical composition of the invention.

Another aspect relates to a method for stimulating, priming and/or expanding T cells, comprising contacting T cells with one or more of: the peptide of the invention, the nucleic acid of the invention comprising a nucleotide sequence encoding the peptide of the invention, the cell of the invention comprising said nucleic acid and/or the cell of the invention that presents the peptide of the invention or a procession product thereof. In one embodiment, the peptide of the invention is presented in the context of MHC molecules such as MHC molecules on the surface of cells, e.g. antigen-presenting cells.

In this aspect, the invention may relate to a method for preparing CLDN6-specific T cells. The T cells may be stimulated, primed and/or expanded in vitro or in vivo. Preferably, the T cells are present in a sample obtained from a subject. The stimulated, primed and/or expanded T cells may be administered to a subject and may be autologous, allogeneic, syngeneic to the subject.

The invention in the above aspects of a method for inducing an immune response in a subject or of a method for stimulating, priming and/or expanding T cells may relate to a method for treating cancer diseases in a subject.

Another aspect relates to a method of killing cancer cells in a subject, comprising the step of providing to the subject a therapeutically effective amount of the peptide of the invention, the nucleic acid of the invention, the cell of the invention, the immunoreactive cell of the invention, the binding agent of the invention, the T cell receptor of the invention, or the artificial T cell receptor of the invention.

The compositions and agents described herein are preferably capable of inducing or promoting a cellular response, preferably cytotoxic T cell activity, against a disease characterized by expression of CLDN6 and/or presentation of CLDN6 with class I MHC, e.g. a cancer disease.

In one aspect, the invention provides the agents and compositions described herein for use in the methods of treatment described herein.

The treatments of cancer diseases described herein can be combined with surgical resection and/or radiation and/or traditional chemotherapy.

In another aspect, the invention relates to a method for determining an immune response in a subject, comprising determining T cells reactive with a peptide of the invention or a cell of the invention presenting a peptide of the invention or a procession product thereof in a biological sample isolated from the subject. The method may comprise the steps of:

(a) incubating a sample comprising T cells isolated from a subject with one or more of:

(i) the peptide of the invention;

(ii) the nucleic acid of the invention comprising a nucleotide sequence encoding the peptide of the invention; and (iii) the cell of the invention comprising said nucleic acid or the cell of the invention presenting a peptide of the invention or a procession product thereof;

and (b) detecting the specific activation of the T cells, therefrom determining the presence or absence of an immune response in said subject.

The invention in the above aspects of a method for determining an immune response in a subject may relate to a method for diagnosing cancer diseases in a subject.

In one embodiment of the methods for diagnosis, the biological sample is from a tissue or organ wherein the cells when the tissue or organ is disease free do not substantially express CLDN6.

Typically, the level of T cells in a biological sample is compared to a reference level, wherein a deviation from said reference level is indicative of the presence and/or stage of a disease in a subject. The reference level may be a level as determined in a control sample (e.g., from a healthy tissue or subject) or a median level from healthy subjects. A "deviation" from said reference level designates any significant change, such as an increase by at least 10%, 20%, or 30%, preferably by at least 40% or 50%, or even more. Preferably, the presence of the T cells in said biological sample or a quantity of the T cells in the biological sample which is increased compared to a reference level indicates the presence of a disease.

T cells may be isolated from patient peripheral blood, lymph nodes, tissue samples such as derived from biopsy and resection, or other source. Reactivity assays may be performed on primary T cells or other appropriate derivatives. For example, T cells may be fused to generate hybridomas. Assays for measuring T cell responsiveness are known in the art, and include proliferation assays and cytokine release assays.

Assays and indices for detecting reactive T cells include but are not limited to the use of IFNγ ELISPOT and IFNγ intracellular cytokine staining. Other various methods are known in the art for determining whether a T cell clone will respond to a particular peptide. Typically the peptide is added to a suspension of the T cells for a period of from one to three days. The response of the T cells may be measured by proliferation, e.g., uptake of labeled thymidine, or by release of cytokines, e.g., IL-2. Various assays are available for detecting the presence of released cytokines. T cell cytotoxic assays can be used to detect cytotoxic T cells having specificity for antigens. In one embodiment, cytotoxic T cells are tested for their ability to kill target cells presenting an antigen with MHC class I molecules. Target cells presenting an antigen may be labeled and added to a suspension of T cells from a patient sample. The cytotoxicity may be measured by quantifying the release of label from lysed cells. Controls for spontaneous and total release may be included in the assay.

In one embodiment of the invention, a cancer described herein involves cancer cells expressing CLDN6 and/or presenting CLDN6 in the context of MHC molecules. In one embodiment of the invention, diseased cells are cancer cells.

In one embodiment, diseased cells such as cancer cells are cells expressing CLDN6 and/or presenting CLDN6 in the context of MHC molecules. In one embodiment, expression of CLDN6 is on the surface of a diseased cell.

In one embodiment of the invention, a cancer is selected from the group consisting of urinary bladder cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

In one embodiment of the invention, cancer cells are cancer cells of a cancer selected from the group consisting of urinary bladder cancer, ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

According to the invention, CLDN6 preferably has the amino acid sequence according to SEQ ID NO: 1 or 2.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, 2nd* Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "immune response" refers to an integrated bodily response to an antigen and preferably refers to a cellular immune response or a cellular as well as a humoral immune response. The immune response may be protective/preventive/prophylactic and/or therapeutic.

"Inducing an immune response" may mean that there was no immune response against a particular antigen before induction, but it may also mean that there was a certain level of immune response against a particular antigen before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor-associated antigen such as CLDN6 may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

A "cellular immune response", a "cellular response", a "cellular response against an antigen" or a similar term is meant to include a cellular response directed to cells characterized by presentation of an antigen with class I or class II MHC. The cellular response relates to cells called T cells or T-lymphocytes which act as either 'helpers' or 'killers'. The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells.

The term "antigen" relates to an agent comprising an epitope against which an immune response is to be generated and/or is directed. Preferably, an antigen in the context of the present invention is a molecule which, optionally after processing, induces an immune reaction, which is preferably specific for the antigen or cells expressing and/or presenting the antigen. The term "antigen" includes in particular proteins and peptides. An antigen is preferably a product which corresponds to or is derived from a naturally occurring antigen. Such naturally occurring antigens may include or may be derived from tumor-associated antigens.

In particular, the antigen or peptide fragments thereof should be recognizable by a T cell receptor. Preferably, the antigen or peptide if recognized by a T cell receptor is able to induce in the presence of appropriate co-stimulatory signals, clonal expansion of the T cell carrying the T cell receptor recognizing the antigen or peptide. In the context of the embodiments of the present invention, the antigen is preferably presented by a cell, preferably by an antigen presenting cell and/or a diseased cell, in the context of MHC molecules, which may result in an immune reaction against the antigen (or cell presenting the antigen).

In a preferred embodiment, an antigen is a tumor-associated antigen, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" or "tumor antigen" relates to proteins that are under normal conditions specifically expressed in a limited number of tissues and/or organs or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a cancer cell and is preferably not or only rarely expressed in normal tissues. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor-associated antigen is identical between the tumor-associated antigen which is expressed in normal tissues and the tumor-associated antigen which is expressed in cancer tissues. Preferably, a tumor-associated antigen is presented by a cancer cell in which it is expressed.

Various aspects of the invention involve the tumor-associated antigen CLDN6 and the present invention may involve the stimulation or provision of an anti-tumor CTL reaction against cancer cells expressing said tumor-associated antigen and preferably presenting said tumor-associated antigen with class I MHC.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family, such as CLDN6, are expressed in tumors of various origins, and are particularly suited as target structures in connection with antibody-mediated cancer immunotherapy due to their selective expression (no expression in a toxicity relevant normal tissue) and localization to the plasma membrane.

CLDN6 has been identified as differentially expressed in tumor tissues, with the only normal tissues expressing CLDN6 being placenta.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof. In one embodiment, the cancer disease associated with CLDN6 expression is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma.

The term "CLDN" as used herein means claudin and includes CLDN6. Preferably, a claudin is a human claudin. The term "CLDN6" relates to claudin 6 and includes any variants thereof.

The term "CLDN6" preferably relates to human CLDN6, and, in particular, to a protein comprising, preferably consisting of the amino acid sequence of SEQ ID NO: 1 or SEQ ID NO: 2 of the sequence listing or a variant of said amino acid sequence. The first extracellular loop of CLDN6 preferably comprises amino acids 28 to 80, more preferably amino acids 28 to 76 of the amino acid sequence shown in SEQ ID NO: 1 or the amino acid sequence shown in SEQ ID NO: 2. The second extracellular loop of CLDN6 preferably comprises amino acids 138 to 160, preferably amino acids 141 to 159, more preferably amino acids 145 to 157 of the amino acid sequence shown in SEQ ID NO: 1 or the amino acid sequence shown in SEQ ID NO: 2. Said first and second extracellular loops preferably form the extracellular portion of CLDN6.

The term "variant" according to the invention refers, in particular, to mutants, splice variants, conformations, isoforms, allelic variants, species variants and species homologs, in particular those which are naturally present.

An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

According to the various aspects of the invention, the aim is preferably to induce or determine an immune response against cancer cells expressing CLDN6 and preferably being characterized by presentation of CLDN6, and to diagnose, treat or prevent a cancer disease involving cells expressing CLDN6. Preferably the immune response involves the stimulation of an anti-CLDN6 CTL response against cancer cells expressing CLDN6 and preferably presenting CLDN6 with class I MHC.

According to the invention, the term "CLDN6 positive cancer" or similar terms means a cancer involving cancer cells expressing CLDN6, preferably on the surface of said cancer cells. Alternatively or additionally, said cancer cells expressing CLDN6 present CLDN6 in the context of MHC molecules. Cancer cells presenting CLDN6 in the context of MHC molecules can be targeted by immunoreactive cells carrying T cell receptors while cancer cells expressing CLDN6 on the surface can be targeted by immunoreactive cells carrying artificial T cell receptors.

"Cell surface" is used in accordance with its normal meaning in the art, and thus includes the outside of the cell which is accessible to binding by proteins and other molecules CLDN6 is expressed on the surface of cells if it is located at the surface of said cells and is accessible to binding by CLDN6-specific antibodies added to the cells.

The term "extracellular portion" or "exodomain" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence. A part or fragment of a protein sequence preferably comprises a sequence of at least 6, in particular at least 8, at least 12, at least 15, at least 20, at least 30, at least 50, or at least 100 consecutive amino acids of the protein sequence. Portions, parts or fragments as discussed above are encompassed by the term "variant" used herein.

According to the invention, CLDN6 is not substantially expressed in a cell if the level of expression is lower compared to expression in placenta cells or placenta tissue. Preferably, the level of expression is less than 10%, preferably less than 5%, 3%, 2%, 1%, 0.5%, 0.1% or 0.05% of the expression in placenta cells or placenta tissue or even lower. Preferably, CLDN6 is not substantially expressed in a cell if the level of expression exceeds the level of expression in non-cancerous tissue other than placenta by no more than 2-fold, preferably 1.5-fold, and preferably does not exceed the level of expression in said non-cancerous tissue. Preferably, CLDN6 is not substantially expressed in a cell if the level of expression is below the detection limit and/or if the level of expression is too low to allow binding by CLDN6-specific antibodies added to the cells.

According to the invention, CLDN6 is expressed in a cell if the level of expression exceeds the level of expression in non-cancerous tissue other than placenta preferably by more than 2-fold, preferably 10-fold, 100-fold, 1000-fold, or 10000-fold. Preferably, CLDN6 is expressed in a cell if the level of expression is above the detection limit and/or if the level of expression is high enough to allow binding by CLDN6-specific antibodies added to the cells. Preferably, CLDN6 expressed in a cell is expressed or exposed on the surface of said cell.

"Target cell" shall mean a cell which is a target for an immune response such as a cellular immune response. Target cells include cells that present an antigen or an antigen epitope, i.e. a peptide fragment derived from an antigen, and include any undesirable cell such as a cancer cell. In preferred embodiments, the target cell is a cell expressing CLDN6 which preferably is present on the cell surface and/or presented with class I MHC.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor-associated antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

Terms such as "epitope", "antigen fragment", "antigen peptide" or "immunogenic peptide" are used interchangeably herein and preferably relate to an incomplete representation of an antigen which is preferably capable of eliciting an immune response against the antigen or a cell expressing or comprising and preferably presenting the antigen. Preferably, the terms relate to an immunogenic portion of an antigen. Preferably, it is a portion of an antigen that is recognized (i.e., specifically bound) by a T cell receptor, in particular if presented in the context of MHC molecules. Certain preferred immunogenic portions bind to an MHC class I or class II molecule such as on the surface of a cell and thus are MHC binding peptides. As used herein, a peptide is said to "bind to" an MHC class I or class II molecule if such binding is detectable using any assay known in the art.

Preferably, the peptides disclosed herein comprising an amino acid sequence selected from the group consisting of SEQ ID NOs: 3, 4 and 5 or a variant of said amino acid sequence are capable of stimulating an immune response, preferably a cellular response against CLDN6 or cells characterized by expression of CLDN6 and preferably characterized by presentation of CLDN6. Preferably, such peptide is capable of stimulating a cellular response against a cell characterized by presentation of CLDN6 with class I MHC and preferably is capable of stimulating CLDN6-responsive CTL. Preferably, the peptides according to the invention are MHC class I and/or class II presented peptides or can be processed to produce MHC class I and/or class II presented peptides. Preferably, the sequence bound to the MHC molecule is selected from SEQ ID NOs: 3, 4 and 5.

If an antigen peptide is to be presented directly, i.e. without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of an antigen peptide which is to be presented directly substantially corresponds and is preferably completely identical to a sequence selected from SEQ ID NOs: 3, 4 and 5.

If an antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing substantially corresponds and is preferably completely identical to a sequence selected from SEQ ID NOs: 3, 4 and 5. Thus, an antigen peptide according to the invention in one embodiment comprises a sequence selected from SEQ ID NOs: 3, 4 and 5 and following processing of the antigen peptide makes up a sequence selected from SEQ ID NOs: 4 and 5.

Peptides having amino acid sequences substantially corresponding to a sequence of a peptide which is presented by MHC molecules may differ at one or more residues that are not essential for TCR recognition of the peptide as presented by the MHC, or for peptide binding to MHC. Such substantially corresponding peptides preferably are also capable of stimulating an antigen-specific cellular response such as antigen-specific CTL. Peptides having amino acid sequences differing from a presented peptide at residues that do not affect TCR recognition but improve the stability of binding to MHC may improve the immunogenicity of the antigen peptide, and may be referred to herein as "optimized peptides". Using existing knowledge about which of these residues may be more likely to affect binding either to the MHC or to the TCR, a rational approach to the design of substantially corresponding peptides may be employed. Resulting peptides that are functional are contemplated as antigen peptides. Sequences as discussed above are encompassed by the term "variant" used herein.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells. Antigen-presenting cells include professional antigen-presenting cells and non-professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Non-professional antigen-presenting cells do not constitutively express the MHC class II proteins required for interaction with naive T cells; these are expressed only upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity.

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFa to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Cells such as antigen presenting cells or target cells can be loaded with MHC class I presented peptides by exposing, i.e. pulsing, the cells with the peptide or transducing the cells with nucleic acid, preferably RNA, encoding a peptide or protein comprising the peptide to be presented, e.g. a nucleic acid encoding the antigen.

In some embodiments, a pharmaceutical composition of the invention comprises an antigen presenting cell loaded with antigen peptide. In this respect, protocols may rely on in vitro culture/differentiation of dendritic cells manipulated in such a way that they artificially present antigen peptide. Production of genetically engineered dendritic cells may involve introduction of nucleic acids encoding antigens or antigen peptides into dendritic cells. Transfection of dendritic cells with mRNA is a promising antigen-loading technique of stimulating strong antitumor immunity. Such transfection may take place ex vivo, and a pharmaceutical composition comprising such transfected cells may then be used for therapeutic purposes. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75: 456-460, 1997. Antigen loading of dendritic cells may be achieved by incubating dendritic cells or progenitor cells with antigen, DNA (naked or within a plasmid vector) or RNA; or with antigen-expressing recombinant bacteria or viruses (e.g., vaccinia, fowipox, adenovirus or lentivirus vectors).

The term "immunogenicity" relates to the relative efficiency of an antigen to induce an immune reaction.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4$^+$ T cell) the recognition of an antigen or an antigen peptide derived from an antigen in the context of MHC class II molecules by T cell receptors, the release of cytokines and/or the activation of CD8$^+$ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

The term "immunoreactive cell" or "immune effector cell" in the context of the present invention relates to a cell which exerts effector functions during an immune reaction. An "immunoreactive cell" preferably is capable of binding an antigen such as an antigen expressed on the surface of a cell or a cell characterized by presentation of an antigen or an antigen peptide derived from an antigen and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably CD4$^+$ and/or CD8$^+$ T cells.

Preferably, an "immunoreactive cell" recognizes an antigen or an antigen peptide derived from an antigen with some degree of specificity, in particular if presented in the context of MHC molecules such as on the surface of antigen presenting cells or diseased cells such as cancer cells. Preferably, said recognition enables the cell that recognizes an antigen or an antigen peptide derived from said antigen to be responsive or reactive. If the cell is a helper T cell (CD4$^+$ T cell) bearing receptors that recognize an antigen or an antigen peptide derived from an antigen in the context of MHC class II molecules such responsiveness or reactivity may involve the release of cytokines and/or the activation of CD8$^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen or an antigen peptide derived from an antigen and are responsive or reactive are also termed "antigen-responsive CTL" herein. If the cell is a B cell such responsiveness may involve the release of immunoglobulins.

According to the invention, the term "immunoreactive cell" also includes a cell which can mature into an immune cell (such as T cell, in particular T helper cell, or cytolytic T cell) with suitable stimulation. Immunoreactive cells comprise CD34$^+$ hematopoietic stem cells, immature and mature T cells and immature and mature B cells. If production of cytolytic or T helper cells recognizing an antigen is desired, the immunoreactive cell is contacted with a cell presenting an antigen or antigen peptide under conditions which favor production, differentiation and/or selection of cytolytic T cells and of T helper cells. The differentiation of T cell precursors into a cytolytic T cell, when exposed to an antigen, is similar to clonal selection of the immune system.

A "lymphoid cell" is a cell which, optionally after suitable modification, e.g. after transfer of a T cell receptor, is capable of producing an immune response such as a cellular immune response, or a precursor cell of such cell, and includes lymphocytes, preferably T lymphocytes, lymphoblasts, and plasma cells. A lymphoid cell may be an immunoreactive cell as described herein. A preferred lymphoid cell is a T cell lacking endogenous expression of a T cell receptor and which can be modified to express such T cell receptor on the cell surface.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptors (TCR). The thymus is the principal organ responsible for the T cell's maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end.

According to the invention, the term "variable region of a T cell receptor" relates to the variable domains of the TCR chains.

The variable region of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens.

According to the invention, the term "at least one of the CDR sequences" preferably means at least the CDR3 sequence. The term "CDR sequences of a T cell receptor chain" preferably relates to CDR1, CDR2 and CDR3 of the α-chain or β-chain of a T cell receptor.

The constant domain of the TCR domain consists of short connecting sequences in which a cysteine residue forms disulfide bonds, which forms a link between the two chains.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4−CD8−) cells. As they progress through their development they become double-positive thymocytes (CD4+CD8+), and finally mature to single-positive (CD4+CD8− or CD4−CD8+) thymocytes that are then released from the thymus to peripheral tissues.

The first signal in activation of T cells is provided by binding of the T cell receptor to a short peptide presented by the major histocompatibility complex (MHC) on another cell. This ensures that only a T cell with a TCR specific to that peptide is activated. The partner cell is usually a professional antigen presenting cell (APC), usually a dendritic cell in the case of naïve responses, although B cells and macrophages can be important APCs. The peptides presented to CD8+ T cells by MHC class I molecules are 8-10 amino acids in length; the peptides presented to CD4+ T cells by MHC class II molecules are longer, as the ends of the binding cleft of the MHC class II molecule are open.

T cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A "sample comprising T cells" may, for example, be peripheral blood mononuclear cells (PBMC).

T cells may be stimulated with antigen, peptide, nucleic acid and/or antigen presenting cells (APCs) that express an antigen. Such stimulation is performed under conditions and for a time sufficient to permit the generation of T cells that are specific for an antigen, a peptide and/or cells presenting an antigen or a peptide.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

In order to generate CD8+ T cell lines, antigen-presenting cells, preferably autologous antigen-presenting cells, transfected with a nucleic acid which produces the antigen may be used as stimulator cells.

Nucleic acids such as RNA encoding T cell receptor (TCR) chains may be introduced into lymphoid cells such as T cells or other cells with lytic potential. In a suitable embodiment, the TCR α- and β-chains are cloned out from an antigen-specific T cell line and used for adoptive T cell therapy. In this respect, the present invention provides T cell receptors specific for CLDN6 or CLDN6 peptides disclosed herein. In general, this aspect of the invention relates to T cell receptors which recognize or bind CLDN6 peptides presented in the context of MHC. The nucleic acids encoding α- and β-chains of a T cell receptor, e.g. a T cell receptor provided according to the present invention, may be contained on separate nucleic acid molecules such as expression vectors or alternatively, on a single nucleic acid molecule. Accordingly, the term "a nucleic acid encoding a T cell receptor" or similar terms relate to nucleic acid molecules encoding the T cell receptor chains on the same or preferably on different nucleic acid molecules.

The term "immunoreactive cell reactive with a peptide" relates to an immunoreactive cell which when it recognizes the peptide, in particular if presented in the context of MHC molecules such as on the surface of antigen presenting cells or diseased cells such as cancer cells, exerts effector functions of immunoreactive cells as described above.

The term "T cell receptor reactive with a peptide" relates to a T cell receptor which when present on an immunoreactive cell recognizes the peptide, in particular if presented in the context of MHC molecules such as on the surface of antigen presenting cells or diseased cells such as cancer cells, such that the immunoreactive cell exerts effector functions of immunoreactive cells as described above.

The term "antigen-reactive T cell" or similar terms relate to a T cell which recognizes an antigen if presented in the context of MHC molecules such as on the surface of antigen presenting cells or diseased cells such as cancer cells and exerts effector functions of T cells as described above.

The term "antigen-specific lymphoid cell" relates to a lymphoid cell which, in particular when provided with an antigen-specific T cell receptor, recognizes the antigen if presented in the context of MHC molecules such as on the surface of antigen presenting cells or diseased cells such as cancer cells and preferably exerts effector functions of T cells as described above. T cells and other lymphoid cells are considered to be specific for antigen if the cells kill target cells expressing an antigen and/or presenting an antigen peptide. T cell specificity may be evaluated using any of a variety of standard techniques, for example, within a chromium release assay or proliferation assay. Alternatively, synthesis of lymphokines (such as interferon-γ) can be measured The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MUG proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

The MHC region is divided into three subgroups, class I, class II, and class III. MHC class I proteins contain an α-chain and β2-microgbulin (not part of the MI-IC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HLA-DRA, and HLA-DRB1.

In one preferred embodiment of all aspects of the invention an MHC molecule is an HLA molecule.

By "cell characterized by presentation of an antigen", "cell presenting an antigen", "antigen presented by a cell", "antigen presented" or similar expressions is meant a cell such as a diseased cell such as a cancer cell, or an antigen presenting cell presenting the antigen it expresses or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

Some therapeutic methods are based on a reaction of the immune system of a patient, which results in a lysis of diseased cells which present an antigen with class I MHC. In this connection, for example autologous cytotoxic T lymphocytes specific for a complex of an antigen peptide and an MHC molecule may be administered to a patient having a disease. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting cytotoxic T lymphocytes, fluorogenic tetramers of MHC class I molecule/peptide complexes are used for obtaining specific clones of cytotoxic T lymphocytes (Altman et al. (1996), Science 274:94-96; Dunbar et al. (1998), Curr. Biol. 8:413-416, 1998).

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al. (2001), Nat Immunol. 2:962-70; Kessels et al. (2001), Nat Immunol. 2:957-61.

Cytotoxic T lymphocytes may also be generated in vivo in a manner known per se. One method uses nonproliferative cells expressing an MHC class I/peptide complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of an antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining an antigen or an antigen peptide with an adjuvant in order to make incorporation into antigen-presenting cells in vivo possible. The antigen or antigen peptide may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., Immunol Lett. (2000), 74:75-9; Ossendorp et al. (1998), J. Exp. Med. 187:693-702. In general, it is possible to administer an effective amount of the tumor-associated antigen to a patient by intradermal injection, for example. However, injection may also be carried out intranodally into a lymph node (Maloy et al. (2001), Proc Natl Acad Sci USA 98:3299-303).

According to the invention the term "artificial T cell receptor" is synonymous with the terms "chimeric T cell receptor" and "chimeric antigen receptor (CAR)".

These terms relate to engineered receptors, which confer an arbitrary specificity such as the specificity of a monoclonal antibody onto an immune effector cell such as a T cell. In this way, a large number of cancer-specific T cells can be generated for adoptive cell transfer. Thus, an artificial T cell receptor may be present on T cells, e.g. instead of or in addition to the T cell's own T cell receptor. Such T cells do not necessarily require processing and presentation of an antigen for recognition of the target cell but rather may recognize preferably with specificity any antigen present on a target cell. Preferably, said artificial T cell receptor is expressed on the surface of the cells. For the purpose of the present invention T cells comprising an artificial T cell receptor are comprised by the term "T cell" as used herein.

In one embodiment, a single-chain variable fragment (scFv) derived from a monoclonal antibody is fused to CD3-zeta transmembrane and endodomain. Such molecules result in the transmission of a zeta signal in response to recognition by the scFv of its antigen target on a target cell and killing of the target cell that expresses the target antigen. Antigen recognition domains which also may be used include among others T-cell receptor (TCR) alpha and beta single chains. In fact almost anything that binds a given target with high affinity can be used as an antigen recognition domain.

Following antigen recognition, receptors cluster and a signal is transmitted to the cell. In this respect, a "T cell signaling domain" is a domain, preferably an endodomain, which transmits an activation signal to the T cell after antigen is bound. The most commonly used endodomain component is CD3-zeta.

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered to express CARs specifically directed towards antigens on the patient's tumor cells, then infused back into the patient.

According to the invention an artificial T cell receptor may replace the function of a T cell receptor as described above and, in particular, may confer reactivity such as cytolytic activity to a cell such as a T cell as described above. However, in contrast to the binding of the T cell receptor to an antigen peptide-MHC complex as described above, an artificial T cell receptor may bind to an antigen, in particular expressed on the cell surface.

The T-cell surface glycoprotein CD3-zeta chain is a protein that in humans is encoded by the CD247 gene. CD3-zeta together with T-cell receptor alpha/beta and gamma/delta heterodimers and CD3-gamma, -delta, and -epsilon, forms the T-cell receptor-CD3 complex. The zeta chain plays an important role in coupling antigen recognition to several intracellular signal-transduction pathways. The term "CD3-zeta" preferably relates to human CD3-zeta, and, in particular, to a protein comprising, preferably consisting of the amino acid sequence of SEQ ID NO: 45 of the sequence listing or a variant of said amino acid sequence.

CD28 (Cluster of Differentiation 28) is one of the molecules expressed on T cells that provide co-stimulatory signals, which are required for T cell activation. CD28 is the receptor for CD80 (B7.1) and CD86 (B7.2). Stimulation through CD28 in addition to the T cell receptor (TCR) can provide a potent co-stimulatory signal to T cells for the production of various interleukins (IL-6 in particular). The term "CD28" preferably relates to human CD28, and, in particular, to a protein comprising, preferably consisting of the amino acid sequence of SEQ ID NO: 44 of the sequence listing or a variant of said amino acid sequence.

According to the invention, CARs may generally comprise three domains.

The first domain is the binding domain which recognizes and binds CLDN6.

The second domain is the co-stimulation domain. The co-stimulation domain serves to enhance the proliferation and survival of the cytotoxic lymphocytes upon binding of the CAR to a targeted moiety. The identity of the co-stimulation domain is limited only in that it has the ability to enhance cellular proliferation and survival upon binding of the targeted moiety by the CAR. Suitable co-stimulation domains include CD28, CD137 (4-1 BB), a member of the tumor necrosis factor (TNF) receptor family, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the CAR constructs comprise two co-stimulation domains. While the particular combinations include all possible variations of the four noted domains, specific examples include CD28+ CD137 (4-1BB) and CD28+CD134 (OX40).

The third domain is the activation signaling domain (or T cell signaling domain). The activation signaling domain serves to activate cytotoxic lymphocytes upon binding of the CAR to CLDN6. The identity of the activation signaling domain is limited only in that it has the ability to induce activation of the selected cytotoxic lymphocyte upon binding of the CLDN6 by the CAR. Suitable activation signaling domains include the T cell CD3[zeta] chain and Fc receptor [gamma]. The skilled artisan will understand that sequence variants of these noted activation signaling domains can be used without adversely impacting the invention, where the variants have the same or similar activity as the domain on which they are modeled. Such variants will have at least about 80% sequence identity to the amino acid sequence of the domain from which they are derived.

The CARs of the present invention may comprise the three domains, together in the form of a fusion protein. Such fusion proteins will generally comprise a binding domain, one or more co-stimulation domains, and an activation signaling domain, linked in a N-terminal to C-terminal direction. However, the CARs of the present invention are not limited to this arrangement and other arrangements are acceptable and include a binding domain, an activation signaling domain, and one or more co-stimulation domains. It will be understood that because the binding domain must be free to bind CLDN6, the placement of the binding domain in the fusion protein will generally be such that display of the region on the exterior of the cell is achieved. In the same manner, because the co-stimulation and activation signaling domains serve to induce activity and proliferation of the cytotoxic lymphocytes, the fusion protein will generally display these two domains in the interior of the cell. The CARs may include additional elements, such as a signal peptide to ensure proper export of the fusion protein to the cells surface, a transmembrane domain to ensure the fusion protein is maintained as an integral membrane protein, and a hinge domain (or spacer region) that imparts flexibility to the binding domain and allows strong binding to CLDN6.

The cells used in connection with the CAR system of the present invention are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target tumor cells. The cytotoxic lymphocytes will preferably be autologous cells, although heterologous cells or allogenic cells can be used.

According to the invention, a "reference" such as a reference sample or reference organism may be used to correlate and compare the results obtained in the methods of the invention from a test sample or test organism. Typically the reference organism is a healthy organism, in particular an organism which does not suffer from a disease such as a cancer disease. A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

According to the invention, the term "binding agent" includes any compound that has a binding capacity to a target. Preferably, such binding agent comprises at least one binding domain for the target. The term includes molecules such as antibodies and antibody fragments, bispecific or multispecific molecules, chimeric antigen receptors (CARs) and all artificial binding molecules (scaffolds) having a binding capacity to the target including but not limited to nanobodies, affibodies, anticalins, DARPins, monobodies, avimers, and microbodies. In one embodiment said binding is a specific binding.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The antibodies described herein are preferably isolated. An "isolated antibody" as used herein, is intended to refer to an antibody which is substantially free of other antibodies having different antigenic specificities (e.g., an isolated antibody that specifically binds to CLDN6 is substantially free of antibodies that specifically bind antigens other than CLDN6). An isolated antibody that specifically binds to an epitope, isoform or variant of human CLDN6 may, however, have cross-reactivity to other related antigens, e.g., from other species (e.g., CLDN6 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition or mixture.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

According to the invention, the term "binding domain for CLDN6" includes and preferably relates to the antigen-binding portion of a CLDN6 antibody, i.e. an antibody which is directed against CLDN6 and is preferably specific for CLDN6.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody".

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

The ability of antibodies and other binding agents to bind an antigen can be determined using standard binding assays (e.g., ELISA, Western Blot, Immunofluorescence and flow cytometric analysis).

Antibodies and derivatives of antibodies are useful for providing binding domains such as antibody fragments, in particular for providing VL and VH regions.

A binding domain for CLDN6 which may be present within an artificial T cell receptor has the ability of binding to CLDN6, i.e. the ability of binding to an epitope present in CLDN6, preferably an epitope located within the extracellular domains of CLDN6, in particular the first extracellular loop, preferably amino acid positions 28 to 76 of CLDN6 or the second extracellular loop, preferably amino acid positions 141 to 159 of CLDN6. In particular embodiments, a binding domain for CLDN6 binds to an epitope on CLDN6 which is not present on CLDN9. Preferably, a binding domain for CLDN6 binds to an epitope on CLDN6 which is not present on CLDN4 and/or CLDN3. Most preferably, a binding domain for CLDN6 binds to an epitope on CLDN6 which is not present on a CLDN protein other than CLDN6.

A binding domain for CLDN6 preferably binds to CLDN6 but not to CLDN9 and preferably does not bind to CLDN4 and/or CLDN3. Preferably, a binding domain for CLDN6 is specific for CLDN6. Preferably, a binding domain for CLDN6 binds to CLDN6 expressed on the cell surface. In particular preferred embodiments, a binding domain for CLDN6 binds to native epitopes of CLDN6 present on the surface of living cells.

In a preferred embodiment, a binding domain for CLDN6 comprises a heavy chain variable region (VH) comprising an amino acid sequence selected from the group consisting of SEQ ID NOs: 30, 32, 34 and 36 or a fragment thereof, or a variant of said amino acid sequence or fragment.

In a preferred embodiment, a binding domain for CLDN6 comprises a light chain variable region (VL) comprising an amino acid sequence selected from the group consisting of SEQ ID NOs: 31, 33, 35, 37, 38 and 39 or a fragment thereof, or a variant of said amino acid sequence or fragment.

In certain preferred embodiments, a binding domain for CLDN6 comprises a combination of heavy chain variable region (VH) and light chain variable region (VL) selected from the following possibilities (i) to (xi):

(i) the VH comprises an amino acid sequence represented by SEQ ID NO: 30 or a fragment thereof and the VL comprises an amino acid sequence represented by SEQ ID NO: 31 or a fragment thereof, (ii) the VH comprises an amino acid sequence represented by SEQ ID NO: 32 or a fragment thereof and the VL comprises an amino acid sequence represented by SEQ ID NO: 33 or a fragment thereof, (iii) the VH comprises an amino acid sequence represented by SEQ ID NO: 34 or a fragment thereof and the VL comprises an amino acid sequence represented by SEQ ID NO: 35 or a fragment thereof, (iv) the VH comprises an amino acid sequence represented by SEQ ID NO: 36 or a fragment thereof and the VL comprises an amino acid sequence represented by SEQ ID NO: 37 or a fragment thereof, (v) the VH comprises an amino acid sequence represented by SEQ ID NO: 32 or a fragment thereof and the VL comprises an amino acid sequence represented by SEQ ID NO: 31 or a fragment thereof, (vi) the VH comprises an amino acid sequence represented by SEQ ID NO: 32 or a fragment thereof and the VL comprises an amino acid sequence represented by SEQ ID NO: 38 or a fragment thereof, (vii) the VH comprises an amino acid sequence represented by SEQ ID NO: 32 or a fragment thereof and the VL comprises an amino acid sequence represented by SEQ ID NO: 39 or a fragment thereof.

In a particularly preferred embodiment, a binding domain for CLDN6 comprises the following combination of heavy chain variable region (VH) and light chain variable region (VL): the VH comprises an amino acid sequence represented by SEQ ID NO: 32 or a fragment thereof and the VL comprises an amino acid sequence represented by SEQ ID NO: 39 or a fragment thereof.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding domain for CLDN6 comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding domains made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment a binding domain comprising one or more CDRs, a set of CDRs or a combination of sets of CDRs as described herein comprises said CDRs in a human antibody framework.

The term "binding" according to the invention preferably relates to a specific binding.

According to the present invention, an agent such as a T cell receptor or an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

An agent is specific for a predetermined target if it is capable of binding to said predetermined target while it is not (substantially) capable of binding to other targets, i.e. has no significant affinity for other targets and does not significantly bind to other targets in standard assays. According to the invention, an agent is specific for CLDN6 if it is capable of binding to CLDN6 but is not (substantially) capable of binding to other targets. Preferably, an agent is specific for CLDN6 if the affinity for and the binding to such other targets does not significantly exceed the affinity for or binding to CLDN6-unrelated proteins such as bovine serum albumin (BSA), casein, human serum albumin (HSA) or non-claudin transmembrane proteins such as MHC molecules or transferrin receptor or any other specified polypeptide. Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, N.Y. (1984), Kuby, Janis Immunology, W. H. Freeman and Company New York, N.Y. (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

It is to be understood that the peptide and protein agents described herein may be provided in vitro or in vivo in the form of a nucleic acid such as RNA encoding the agent and/or in the form of a host cell comprising a nucleic acid such as RNA encoding the agent. In particular, a variety of methods may be used to introduce CAR constructs into T cells including non-viral-based DNA transfection, transposon-based systems and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems.

The peptide and protein agents described herein may be delivered to a patient by administering a nucleic acid such as RNA encoding the agent and/or by administering a host cell comprising a nucleic acid such as RNA encoding the agent. A nucleic acid when administered to a patient may be present in naked form or in a suitable delivery vehicle such as in the form of liposomes or viral particles, or within a host cell. The nucleic acid provided can produce the agent over extended time periods in a sustained manner mitigating the instability at least partially observed for therapeutic proteins. If a nucleic acid is administered to a patient without being present within a host cell, it is preferably taken up by cells of the patient for expression of the agent encoded by the nucleic acid. If a nucleic acid is administered to a patient while being present within a host cell, it is preferably expressed by the host cell within the patient so as to produce the agent encoded by the nucleic acid.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a nucleic acid is preferably an isolated nucleic acid.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the agents described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that the nucleic acids are also functionally linked naturally and the term "heterologous" means that the nucleic acids are not functionally linked naturally.

A nucleic acid and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "nucleic acid encoding" means that nucleic acid, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding an agent described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

According to the present invention, any technique useful for introducing, i.e. transferring or transfecting, nucleic acids into cells may be used. Preferably, RNA is transfected into cells by standard techniques. Such techniques include electroporation, lipofection and microinjection. In one particularly preferred embodiment of the present invention, RNA is introduced into cells by electroporation.

Electroporation or electropermeabilization relates to a significant increase in the electrical conductivity and permeability of the cell plasma membrane caused by an externally applied electrical field. It is usually used in molecular biology as a way of introducing some substance into a cell.

According to the invention it is preferred that introduction of nucleic acid encoding a protein or peptide into cells results in expression of said protein or peptide.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

According to the invention, a peptide may include natural amino acids and non-natural amino acids. In one embodiment, a peptide merely includes natural amino acids.

According to the invention, the term "non-natural amino acid" refers to an amino acid having a structure different from those of the 20 natural amino acid species. Since non-natural amino acids have structures similar to those of natural amino acids, non-natural amino acids may be classified as derivatives or analogs of given natural amino acids.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding of a peptide to an MHC molecule and/or to a T cell receptor or of a T cell receptor to its target or to sustain effector functions of a T cell. Preferably, a sequence modified with respect to a specific sequence, when it replaces the specific sequence in a T cell receptor retains binding of said T cell receptor to the target and preferably functions of said T cell receptor or T cell carrying the T cell receptor as described herein.

For example, the sequences shown in the sequence listing can be modified so as to remove one or more, preferably all free cysteine residues, in particular by replacing the cysteine residues by amino acids other than cysteine, preferably serine, alanine, threonine, glycine, tyrosine, leucine or methionine, most preferably alanine or serine. For example, the cysteine at position 45 of the sequence shown in SEQ ID NO: 33 of the sequence listing or the corresponding cysteine in a sequence comprising said sequence may be modified in this way.

It will be appreciated by those skilled in the art that in particular the sequences of the CDR sequences, hypervariable and variable regions can be modified without losing the ability to bind to a target. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions specifically disclosed herein.

A peptide "variant" may retain the immunogenicity of a given peptide (e.g. the ability of the variant to react with T cell lines or clones is not substantially diminished relative to the given peptide). In other words, the ability of a variant to react with T cell lines or clones may be enhanced or unchanged, relative to the given peptide, or may be diminished by less than 50%, and preferably less than 20%, relative to the given peptide.

A variant may be identified by evaluating its ability to bind to a MHC molecule. In one preferred embodiment, a variant peptide has a modification such that the ability of the variant peptide to bind to a MHC molecule is increased relative to the given peptide. The ability of the variant peptide to bind to a MHC molecule may be increased by at least 2-fold, preferably at least 3-fold, 4-fold, or 5-fold relative to that of a given peptide. Accordingly, within certain preferred embodiments, a peptide comprises a variant in which 1 to 3 amino acid resides within an immunogenic portion are substituted such that the ability to react with T cell lines or clones is statistically greater than that for the unmodified peptide. Such substitutions are preferably located within an MHC binding site of the peptide. Preferred substitutions allow increased binding to MHC class I or class II molecules. Certain variants contain conservative substitutions.

The term "variant" according to the invention also includes mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package. Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing proteins and peptides having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, myristoylation, palmitoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

Also included are mimetics of peptides. Such mimetics may comprise amino acids linked to one or more amino acid mimetics (i e., one or more amino acids within the peptide may be replaced by an amino acid mimetic) or may be entirely nonpeptide mimetics. An amino acid mimetic is a compound that is conformationally similar to an amino acid, e.g. such that it can be substituted for an amino acid without substantially diminishing the ability to react with T cell lines or clones. A nonpeptide mimetic is a compound that does not contain amino acids, and that has an overall conformation that is similar to a peptide, e.g. such that the ability of the mimetic to react with T cell lines or clones is not substantially diminished relative to the ability of a given peptide.

According to the invention, a variant, derivative, modified form, fragment, part or portion of an amino acid sequence, peptide or protein preferably has a functional property of the amino acid sequence, peptide or protein, respectively, from which it has been derived, i.e. it is functionally equivalent. In one embodiment, a variant, derivative, modified form, fragment, part or portion of an amino acid sequence, peptide or protein is immunologically equivalent to the amino acid sequence, peptide or protein, respectively, from which it has been derived. In one embodiment, the functional property is an immunological property.

A particular property is the ability to form a complex with MHC molecules and, where appropriate, generate an immune response, preferably by stimulating cytotoxic or T helper cells.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide or peptide variant used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (Tor example *Saccharomyces cerevisiae*), *Schizosaccharomyces* (for example Schizo *saccharomyces pombe*), *Pichia* (for example *Pichia pastoris* and *Pichia methanolica*), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

A cell which comprises a nucleic acid molecule preferably express the peptide or protein encoded by the nucleic acid.

The cell may be a recombinant cell and may secrete the encoded peptide or protein, may express it on the surface and preferably may additionally express an MHC molecule which binds to said peptide or protein or a procession product thereof. In one embodiment, the cell expresses the MHC molecule endogenously. In a further embodiment, the cell expresses the MHC molecule and/or the peptide or protein or the procession product thereof in a recombinant manner. The cell is preferably nonproliferative. In a preferred embodiment, the cell is an antigen-presenting cell, in particular a dendritic cell, a monocyte or a macrophage.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

A disease associated with antigen expression may be detected based on the presence of T cells that specifically react with a peptide in a biological sample. Within certain methods, a biological sample comprising CD4+ and/or CD8+ T cells isolated from a patient is incubated with a peptide of the invention, a nucleic acid encoding such peptide and/or an antigen-presenting cell that expresses and/or presents at least an immunogenic portion of such a peptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). For CD4+ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free subjects indicates the presence of a disease associated with antigen expression in the subject.

"Reduce" or "inhibit" as used herein means the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The agents, compositions and methods described herein can be used to treat a subject with a disease, e.g., a disease characterized by the presence of diseased cells expressing CLDN6 and preferably presenting CLDN6 in the context of MHC molecules. Examples of diseases which can be treated and/or prevented encompass all diseases expressing CLDN6. Particularly preferred diseases are cancer diseases.

The agents, compositions and methods described herein may also be used for immunization or vaccination to prevent a disease described herein.

The terms "normal tissue" or "normal conditions" refer to healthy tissue or the conditions in a healthy subject, i.e., non-pathological conditions, wherein "healthy" preferably means non-cancerous.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing CLDN6 and optionally presenting CLDN6 in the context of MHC molecules.

"Diseases involving cells expressing CLDN6" or similar expressions means according to the invention that CLDN6 is expressed in cells of a diseased tissue or organ. In one embodiment, expression of CLDN6 in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving cells expressing CLDN6 include cancer diseases. Furthermore, according to the invention, cancer diseases preferably are those wherein the cancer cells express CLDN6.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing CLDN6 and a cancer cell expresses CLDN6.

A diseased cell preferably is a cell expressing CLDN6 said CLDN6 preferably being present on the surface of said cell as transmembrane protein and/or being presented by said cell in the context of MHC such as MHC I. A cell expressing CLDN6 preferably is a cancer cell, preferably of the cancers described herein.

In one embodiment, a cancer disease is a malignant disease which is characterized by the properties of anaplasia, invasiveness, and metastasis. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

Lymphoma and leukemia are malignancies derived from hematopoietic (blood-forming) cells.

Blastic tumor or blastoma is a tumor (usually malignant) which resembles an immature or embryonic tissue. Many of these tumors are most common in children.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of an agent or composition of the invention, preferably protects the recipient from the development of a disease. A therapeutic administration of an immunotherapy, for example, a therapeutic administration of an agent or composition of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein preferably function to remove CLDN6-expressing cells from a patient. Such removal may take place as a result of enhancing or inducing an immune response in a patient specific for CLDN6 or a cell expressing CLDN6 and/or presenting CLDN6 in the context of MHC molecules.

Within certain embodiments, immunotherapy may be active immunotherapy, in which treatment relies on the in vivo stimulation of the endogenous host immune system to react against diseased cells with the administration of immune response-modifying agents (such as peptides and nucleic acids as provided herein).

Within other embodiments, immunotherapy may be passive immunotherapy, in which treatment involves the delivery of agents with established tumor-immune reactivity (such as effector cells) that can directly or indirectly mediate antitumor effects and does not necessarily depend on an intact host immune system. Examples of effector cells include T lymphocytes (such as CD8+ cytotoxic T lymphocytes and CD4+ T-helper lymphocytes), and antigen-presenting cells (such as dendritic cells and macrophages). T cell receptors specific for the CLDN6 peptides recited herein and artificial T cell receptors specific for CLDN6 may be transferred into effector cells for adoptive immunotherapy.

As noted above, immunoreactive peptides as provided herein may be used to rapidly expand antigen-specific T cell cultures in order to generate a sufficient number of cells for immunotherapy. In particular, antigen-presenting cells, such as dendritic cells, macrophages, monocytes, fibroblasts and/or B cells, may be pulsed with immunoreactive peptides or transfected with one or more nucleic acids using standard techniques well known in the art. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al. (1997), Immunological Reviews 157, 177.

Alternatively, a nucleic acid expressing a peptide recited herein may be introduced into antigen-presenting cells taken from a patient and clonally propagated ex vivo for transplant back into the same patient.

Transfected cells may be reintroduced into the patient using any means known in the art, preferably in sterile form by intravenous, intracavitary, intraperitoneal or intratumor administration.

Methods disclosed herein may involve the administration of autologous T cells that have been activated in response to a peptide or peptide-expressing antigen presenting cell. Such T cells may be CD4+ and/or CD8+, and may be proliferated as described above. The T cells may be administered to the subject in an amount effective to inhibit the development of a disease.

The term "immunization" or "vaccination" describes the process of treating a subject with the purpose of inducing an immune response for therapeutic or prophylactic reasons.

The term "in vivo" relates to the situation in a subject.

According to the invention, a "sample" may be any sample useful according to the present invention, in particular a biological sample such a tissue sample, including body fluids, and/or a cellular sample and may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid and peptide/protein isolates.

The compounds and agents described herein may be administered in the form of any suitable pharmaceutical composition.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectible formulation may comprise a pharmaceutically acceptable excipient such as Ringer Lactate.

The term "carrier" refers to an organic or inorganic component, of a natural or synthetic nature, in which the active component is combined in order to facilitate, enhance or enable application.

According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by expression of CLDN6.

For example, in one embodiment, agents described herein can be used to treat a patient with a cancer disease, e.g., a cancer disease such as described herein characterized by the presence of cancer cells expressing CLDN6.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, IFNα, IFNγ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The pharmaceutical composition can be administered locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

Administration may also be carried out, for example, orally, intraperitonealy or intramuscularly.

The agents and compositions provided herein may be used alone or in combination with conventional therapeutic regimens such as surgery, irradiation, chemotherapy and/or bone marrow transplantation (autologous, syngeneic, allogeneic or unrelated).

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Representation of the TCR-CD3 complex. The intracytoplasmic CD3 immunoreceptor tyrosine-based activation motifs (ITAMs) are indicated as cylinders (adapted from "The T cell receptor facts book", M P Lefranc, G Lefranc, 2001).

FIG. 2: The design of successive generations of CARs. Schematic representation of the different generations of CARs (1G, first generation, 2G, second generation, 3G, third generation). The first generation contains extracellular scFvs and the cytoplasmic CD3 chain/ZAP70 mediating cytotoxicity, the second generation additionally CD28/PI3K promoting proliferation and the third generation furthermore 4-1BB or OX40/TRAF sustaining cell survival (Casucci, M. et al. (2011) 2: 378-382).

Figure 3:
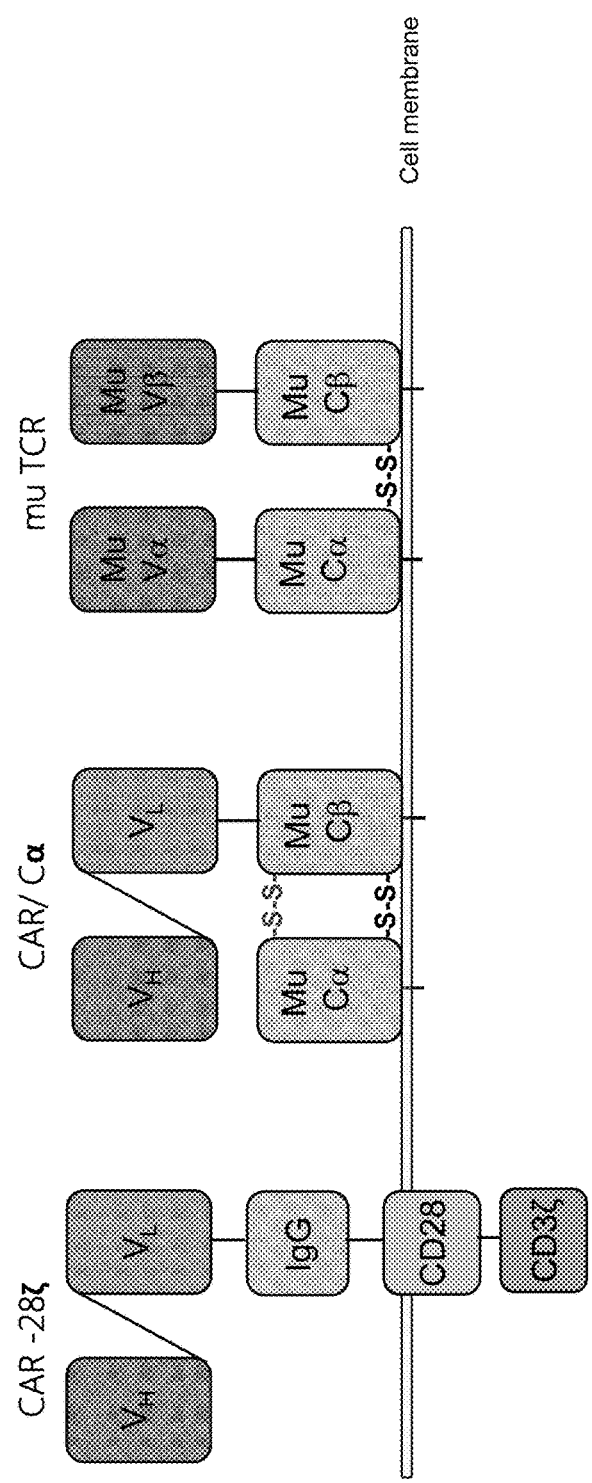

FIG. 3: Schematic representation of the different receptor formats for the redirection of T cells against CLDN6. Left: a second generation CAR consisting of a CLDN6-specific scFv fragment, a IgG1-derived spacer domain, a CD28 costimulatory and a CD3ζ signaling domain (CAR-28ζ); middle: a novel CAR format based on the linkage of the scFv with the constant domain of the murine TCRß chain and coexpression of the constant domain of the murine TCRα chain (CAR/Cα); right: a murine TCR composed of TCR α/β chains (mu, murine TCR);

FIG. 4: Claudin-6 expression in normal tissues and different cancers. The CLDN6 mRNA expression was analyzed by qRT-PCR in different normal tissue and 47 ovarian carcinoma specimens.

Figure 5:
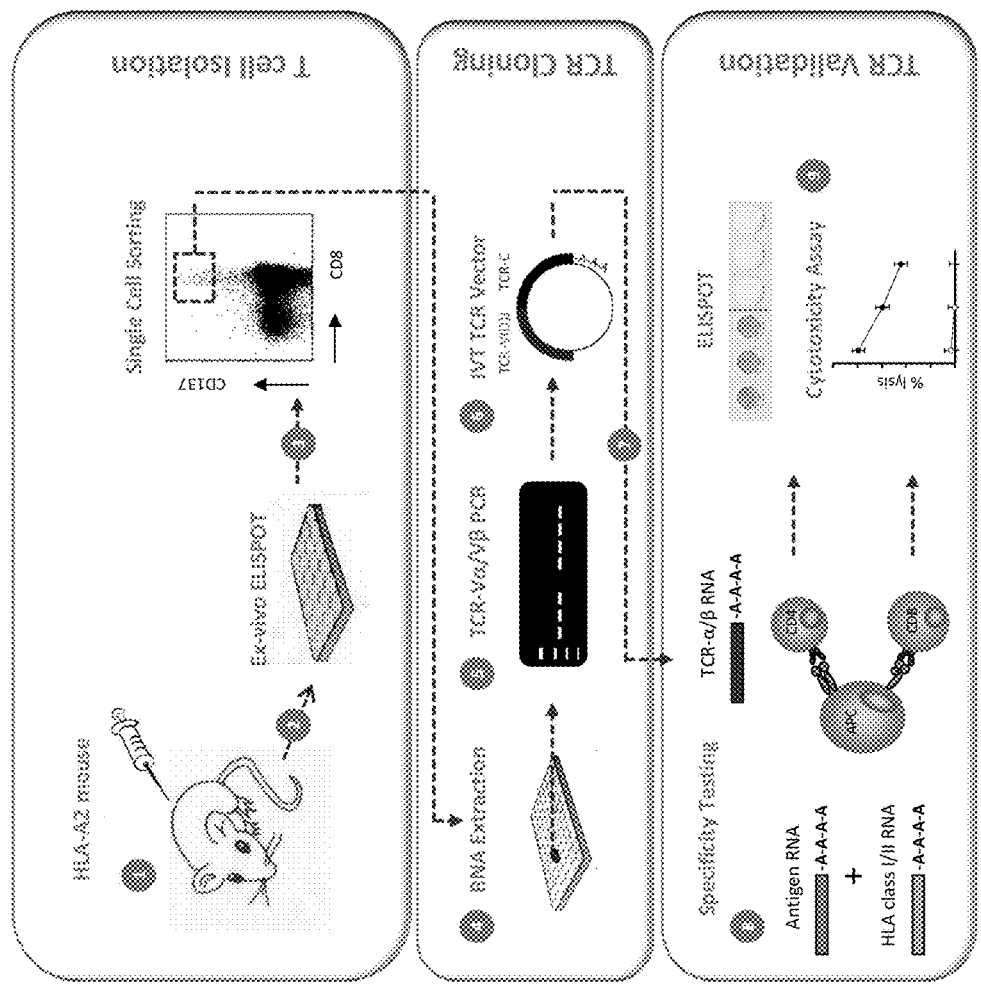

FIG. 5. Technology platform for TCR isolation and validation. The approach integrates all steps from isolation of antigen-specific T cells (top) to TCR cloning (middle) and TCR validation (bottom). HLA-A2/DR1-transgenic mice are immunized with tumor antigen encoding mRNA. Spleen cells of these mice are analyzed for ex vivo reactivity against the respective antigen by IFNγ-ELISPOT and antigen-specific murine CD8+ T cells are isolated after in vitro restimulation based on activation-induced expression of CD137 by flow cytometry (top). Single cells are harvested in multi-well-plates and subjected to first-strand cDNA synthesis and enrichment by a global PCR amplification step. TCR α/β variable regions are cloned into vectors for in vitro transcription (IVT) containing the constant region cassettes (middle). TCR α/β chain RNAs are transferred into human CD8+ T cells, cocultured with APCs expressing the appropriate antigen and HLA molecules and tested for functional reprogramming of engineered T cells (bottom).

Figure 6:
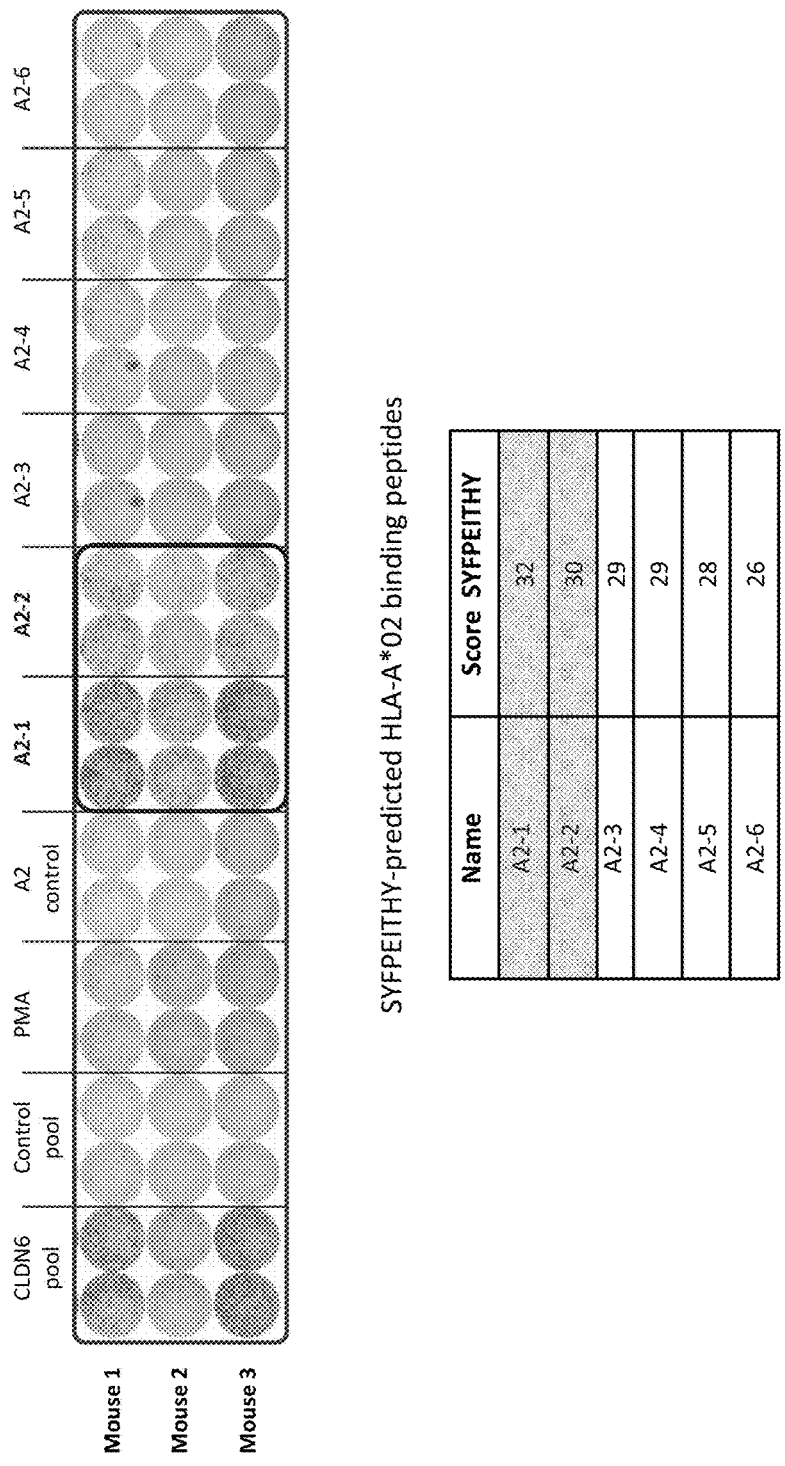

FIG. 6: Ex vivo reactivity of spleen cells from immunized HLA-A*02-transgenic mice against CLDN6-derived peptides analyzed by IFNy-ELISPOT assay. HLA-A*02 CLDN6-specific binding peptides were predicted applying a specific algorithm (Rammensee H. et al. (1999) Immunogenetics 50, 213-9). Spleen cells were analyzed for reactivity against CLDN6 peptide pool or predicted HLA-A*02-binding CLDN6-derived peptides A2-1-6. Positive control: PMA-treated spleen cells; negative control: an irrelevant peptide pool (HIV-gag), irrelevant nonamer peptide (PLAC1-31-39).

Figure 7:
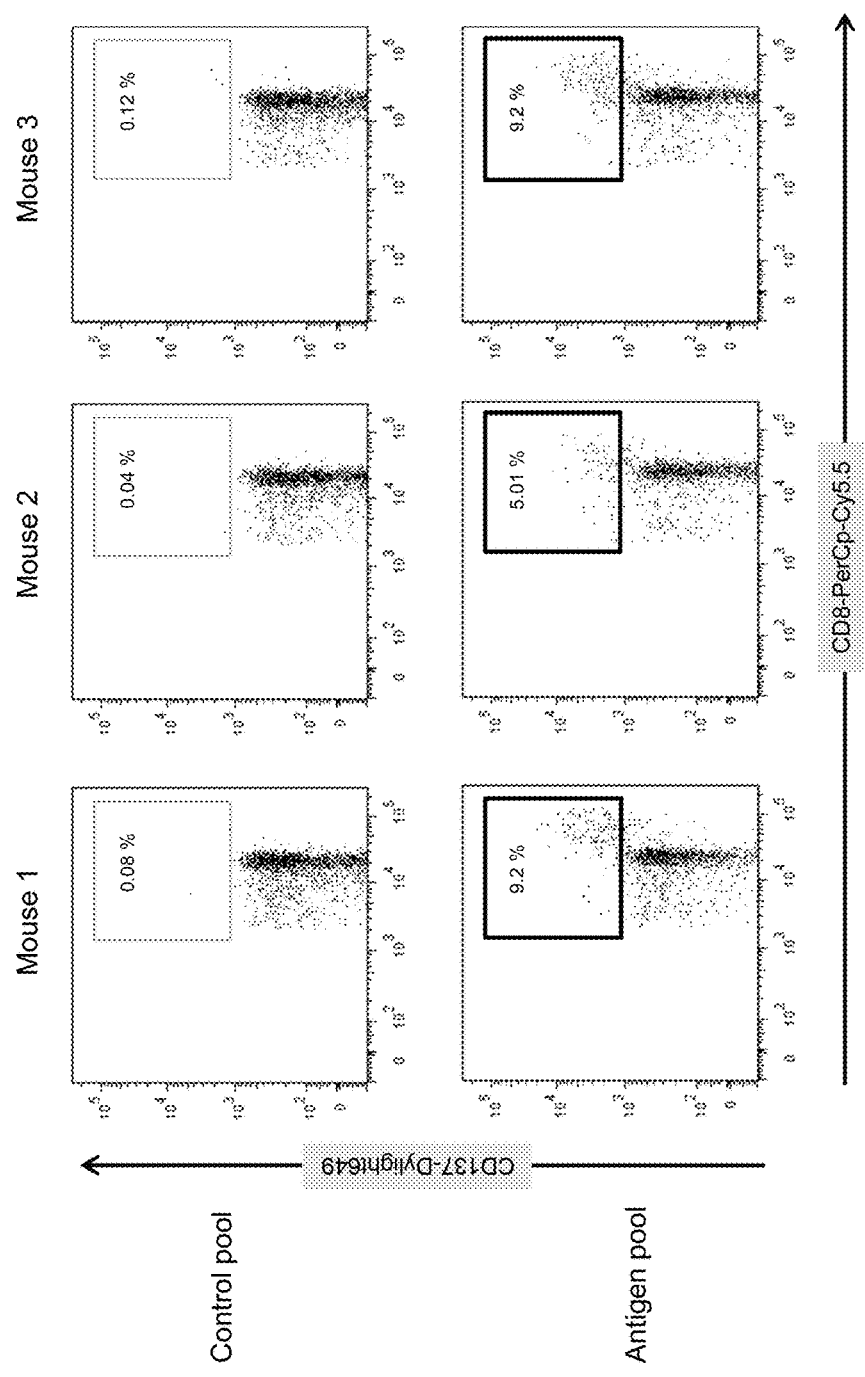

FIG. 7: Flow cytometry sorting of CLDN6-specific murine CD8+ T cells from HLA-A*02-transgenic mice after in-vitro restimulation. Single CD8+/CD137+ T cells were isolated by flow cytometry and harvested in multiwell plates for TCR cloning after restimulation of spleen cells with CLDN6 overlapping peptide pool. Control: spleen cells restimulated with irrelevant peptide pool.

Figure 8:
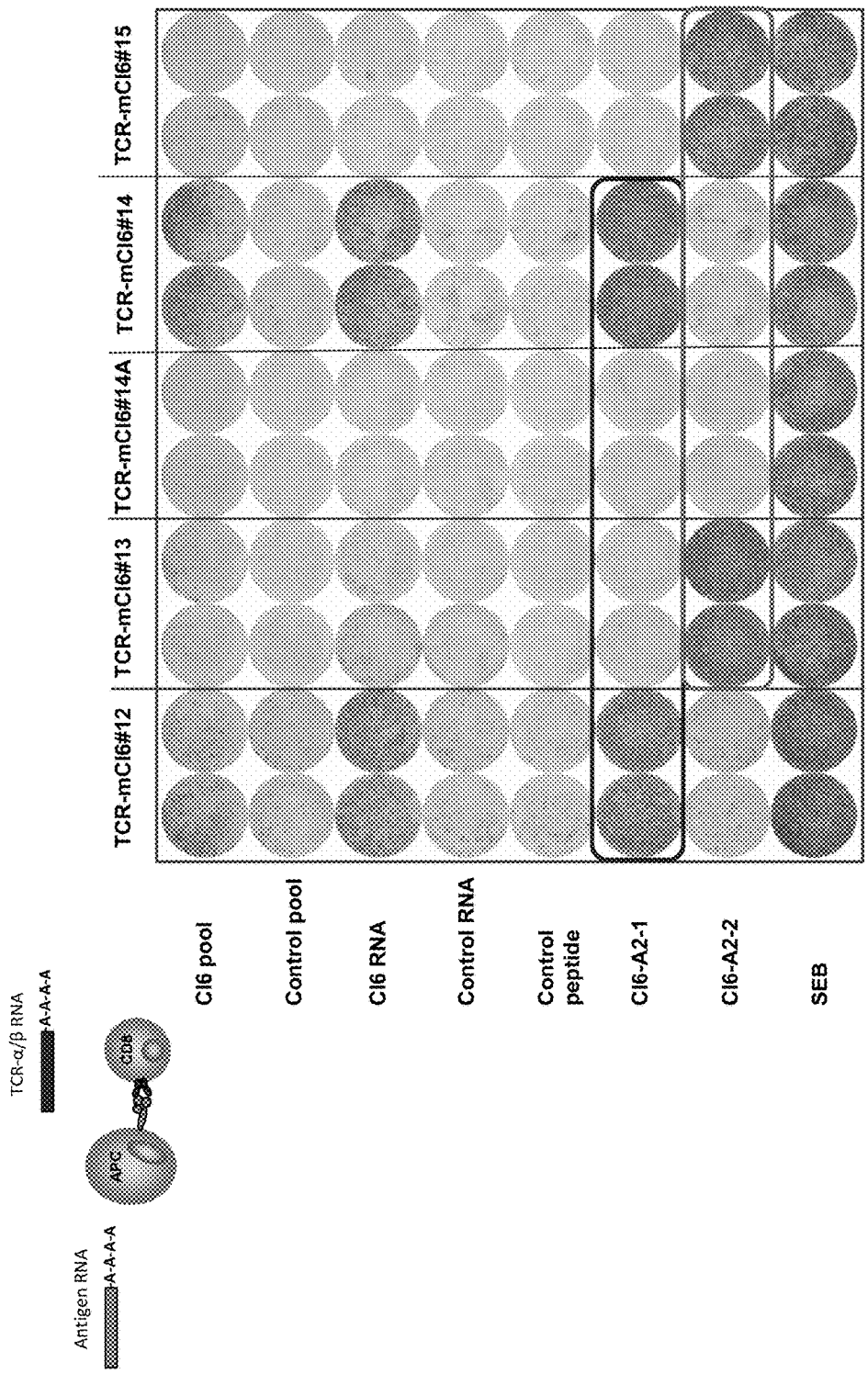

FIG. 8: Specificity testing of TCRs isolated from CD8+ T cells of CLDN6-immunized mice. CD8+ T cells of a HLA-A*02-positive healthy donor were transfected with TCR-α/β chain RNAs and tested for recognition of K562-A2 cells transfected with CLDN6 RNA or pulsed with CLDN6 overlapping 15mer peptides (=Cl6 pool) or CLDN6 HLA-A*02 binding peptides (Cl6-A2-1, Cl6-A2-2) by IFNγ-ELISPOT. Negative controls: irrelevant peptide pool, irrelevant 9mer peptide; Positive control: SEB FIG. 9: Surface expression of CLDN6-specific murine TCRs on human preactivated CD8+ T cells. CD8+ T cells were preactivated with OKT3 and transfected with 20 µg TCR α/β RNA. 20 h after electroporation cells were stained with a PE-conjugated anti-CD8 antibody and APC-conjugated antibody recognizing the murine constant domain of the TCR ß chain. Cells were gated on single lymphocytes.

Figure 10:
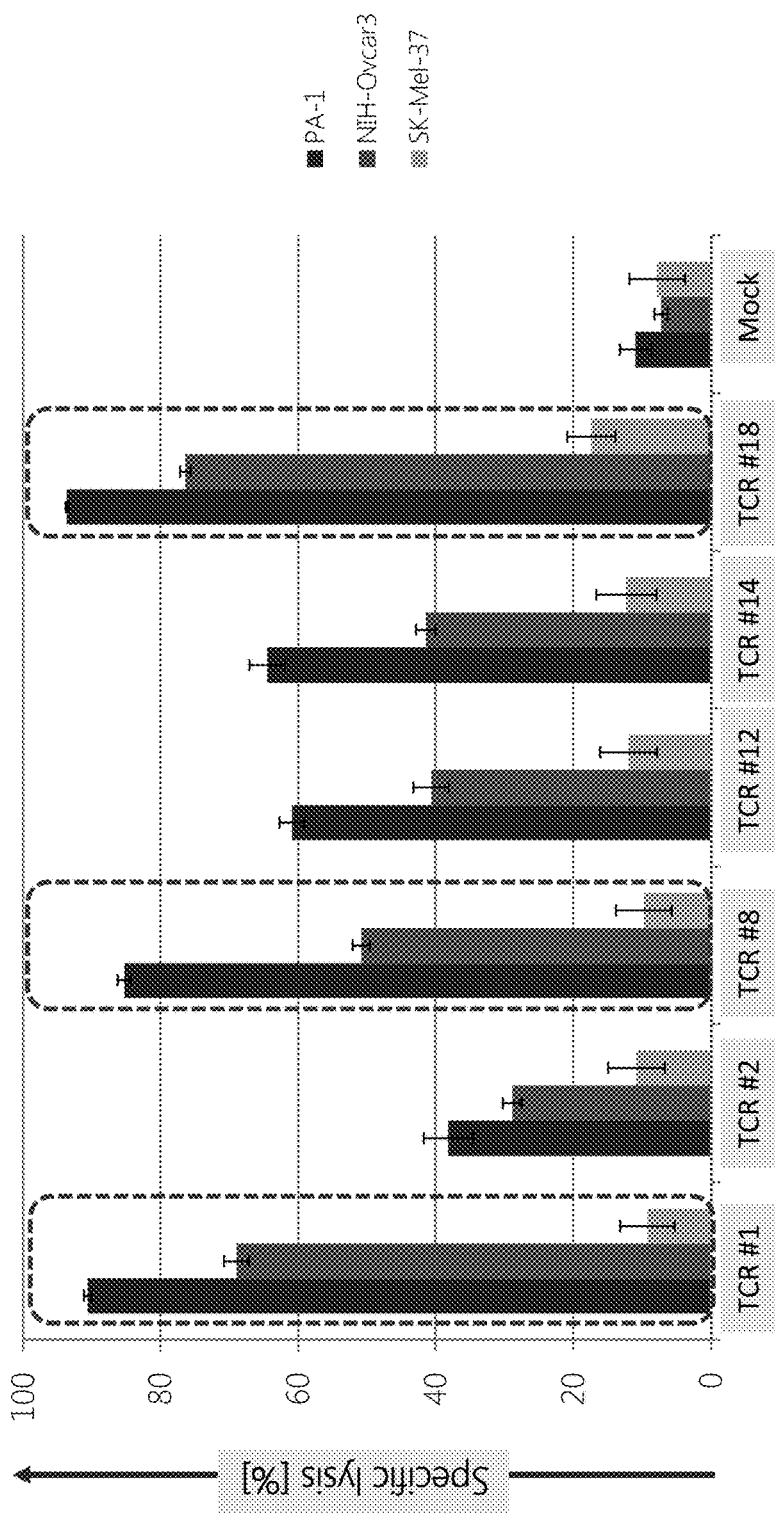

FIG. 10: Tumor cell lysis mediated by CLDN6-specific TCRs. Preactivated CD8+ T cells were transfected with 20 µg TCR α/β RNAs and cocultured 20 h later together with HLA-A*02-expressing CLDN6-positive (PA1-Luc; NIH-OvCar3) or -negative (SK-Mel-37) tumor cell lines with an E:T (effector cell:target cell) ratio of 30:1. Specific lysis was analyzed by luciferase-based cytotoxicity assay after 4 h coculture.

Figure 11:
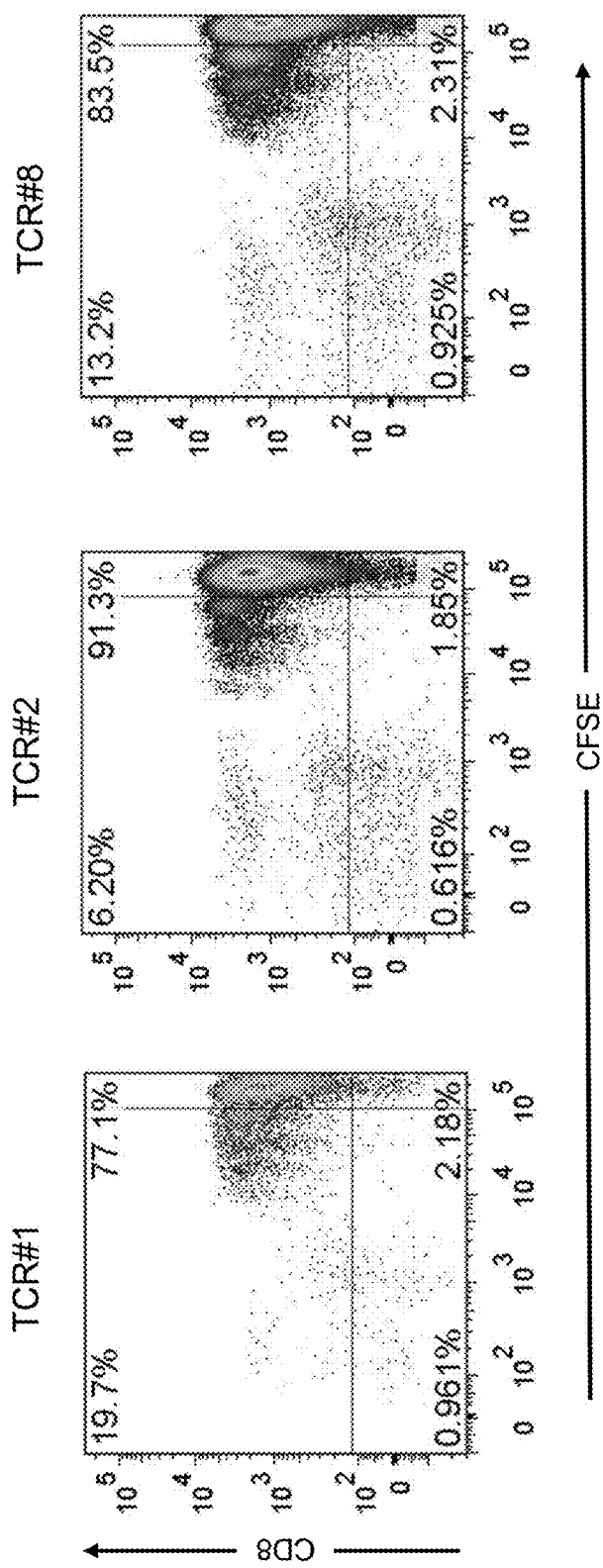
Figure 11:
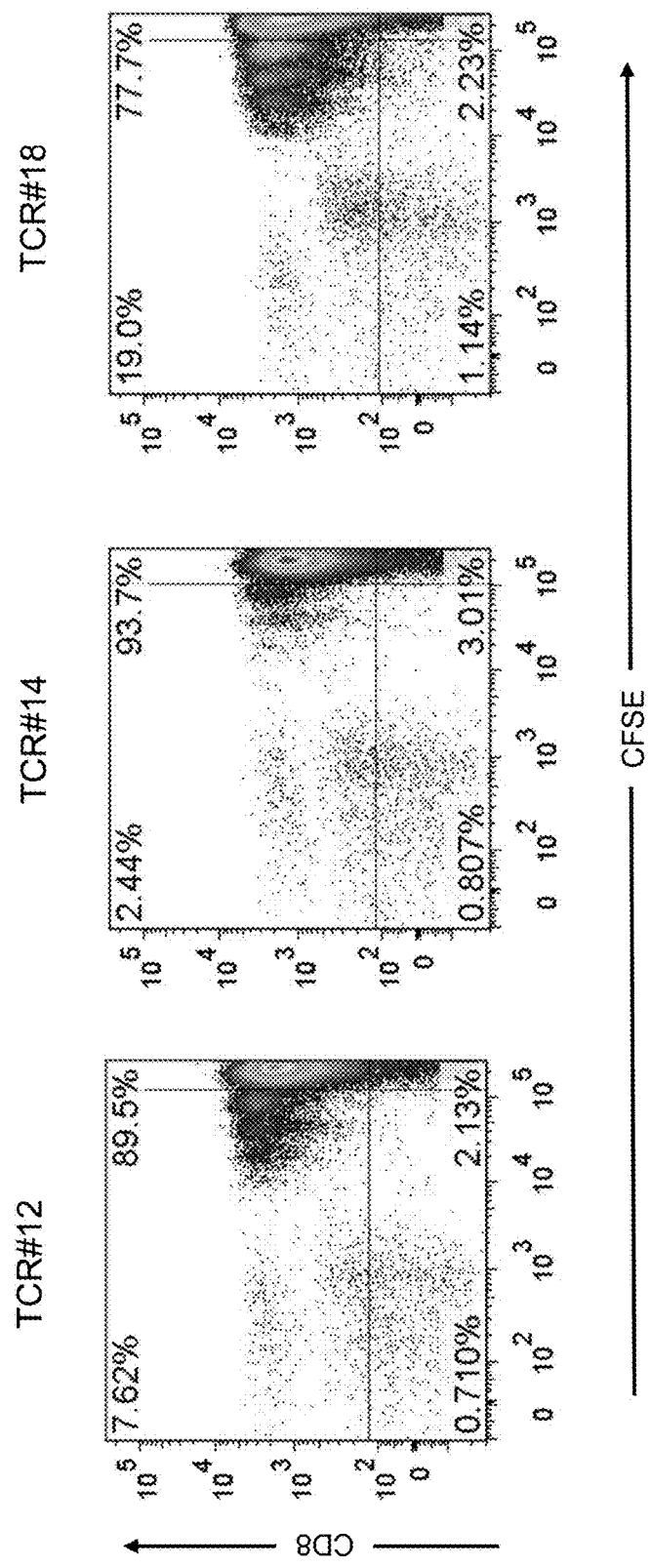
Figure 11:
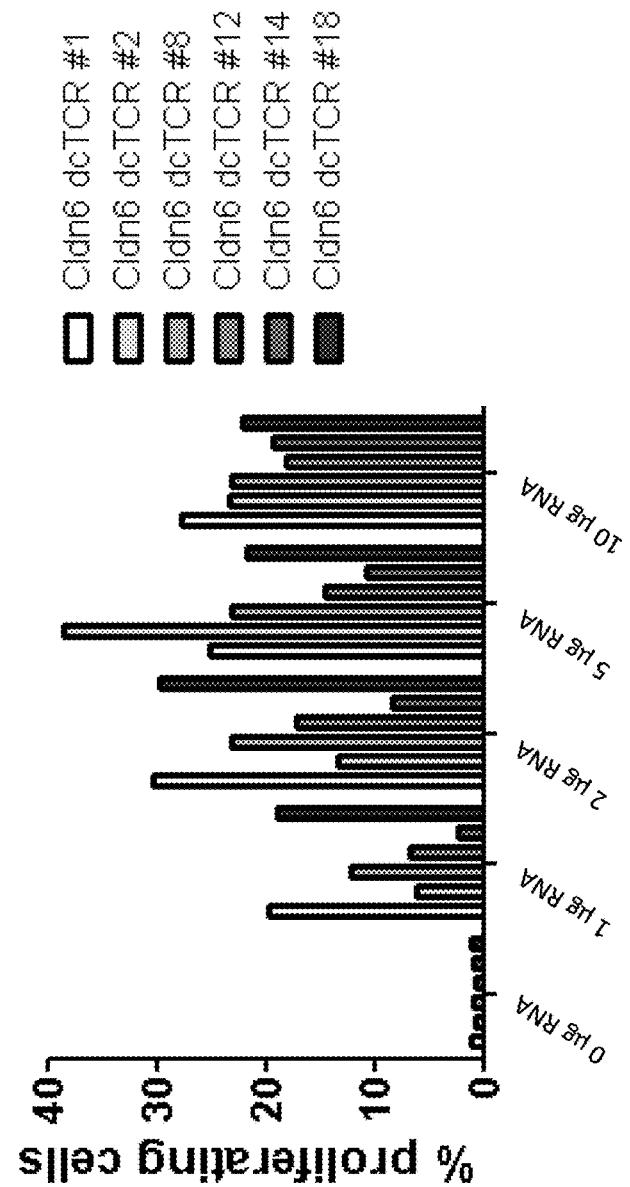

FIG. 11: Dose-dependent proliferation mediated by CLDN6-specific TCRs in response to CLDN6-expressing target cells. CD8+ T cells were transfected with 20 µg TCR RNA, labeled with CFSE and cocultured with autologous monocytes transfected with titrated amounts of CLDN6 RNA. After 4 days of coculture cells were stained with an APC-Cy7-labeled anti-CD8 antibody. A) Specific proliferation was analyzed by flowcytometry based on the dilution of the CFSE proliferation dye. Dotplots show living CD8+ T lymphocytes after coculture with monocytes transfected with 1 CLDN6-RNA. B) Bars show the percentage of proliferating CD8+ T cells.

Figure 12:
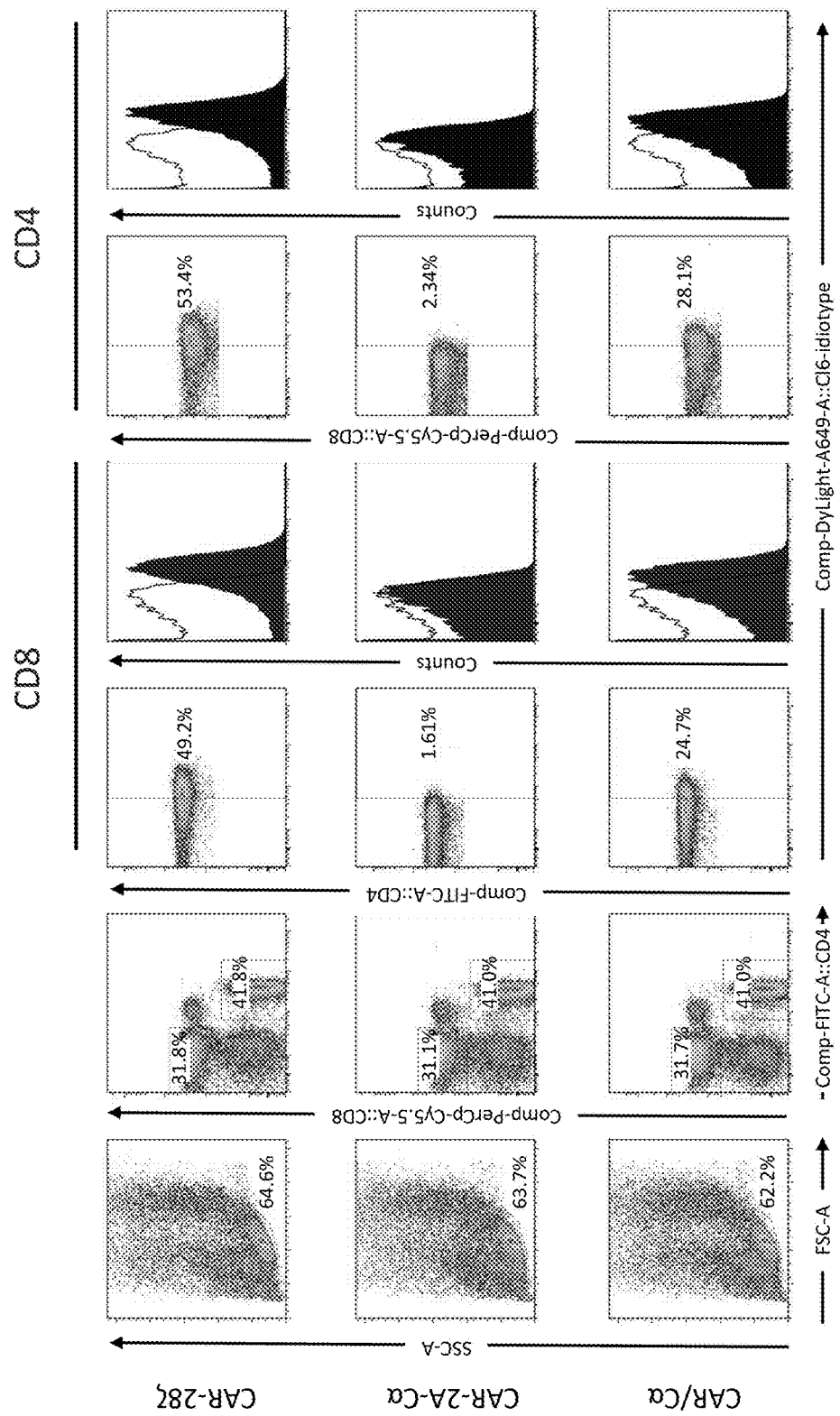
Figure 12:
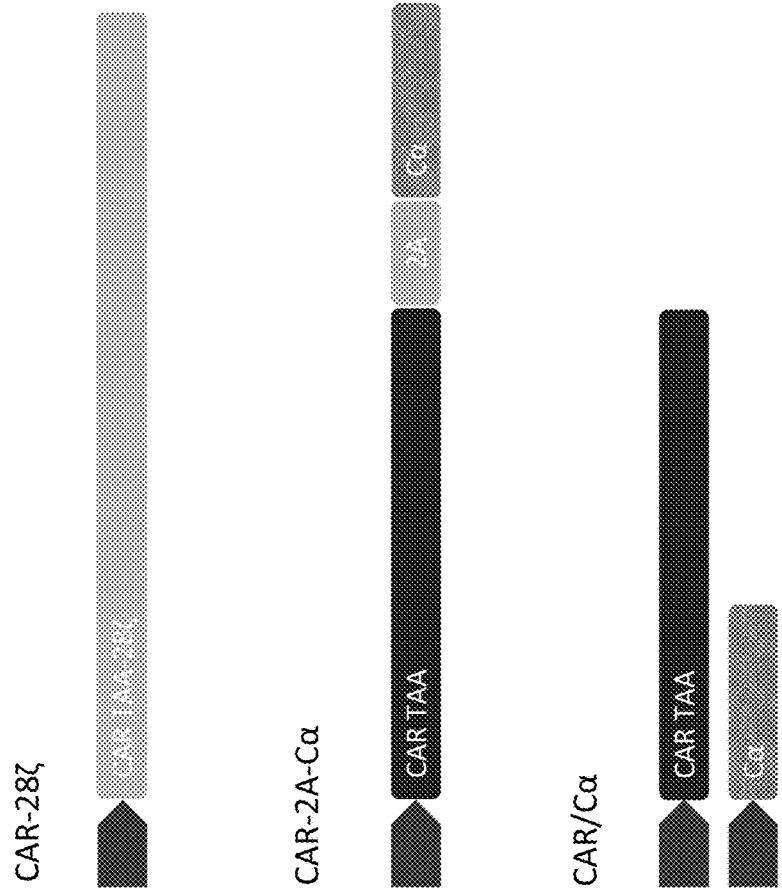

FIG. 12: Surface expression of CLDN6-specific CAR constructs on resting human CD4+ and CD8+ T cells. PBMCs were transfected with 10 µg CAR RNA. 20 h after electroporation cells were stained with a PE-conjugated anti-CD8, a FITC-conjugated anti-CD4 and an idiotype-specific antibody labeled with Dylight-650. Cells were gated on single CD4+ or CD8+ T cells.

Figure 13:
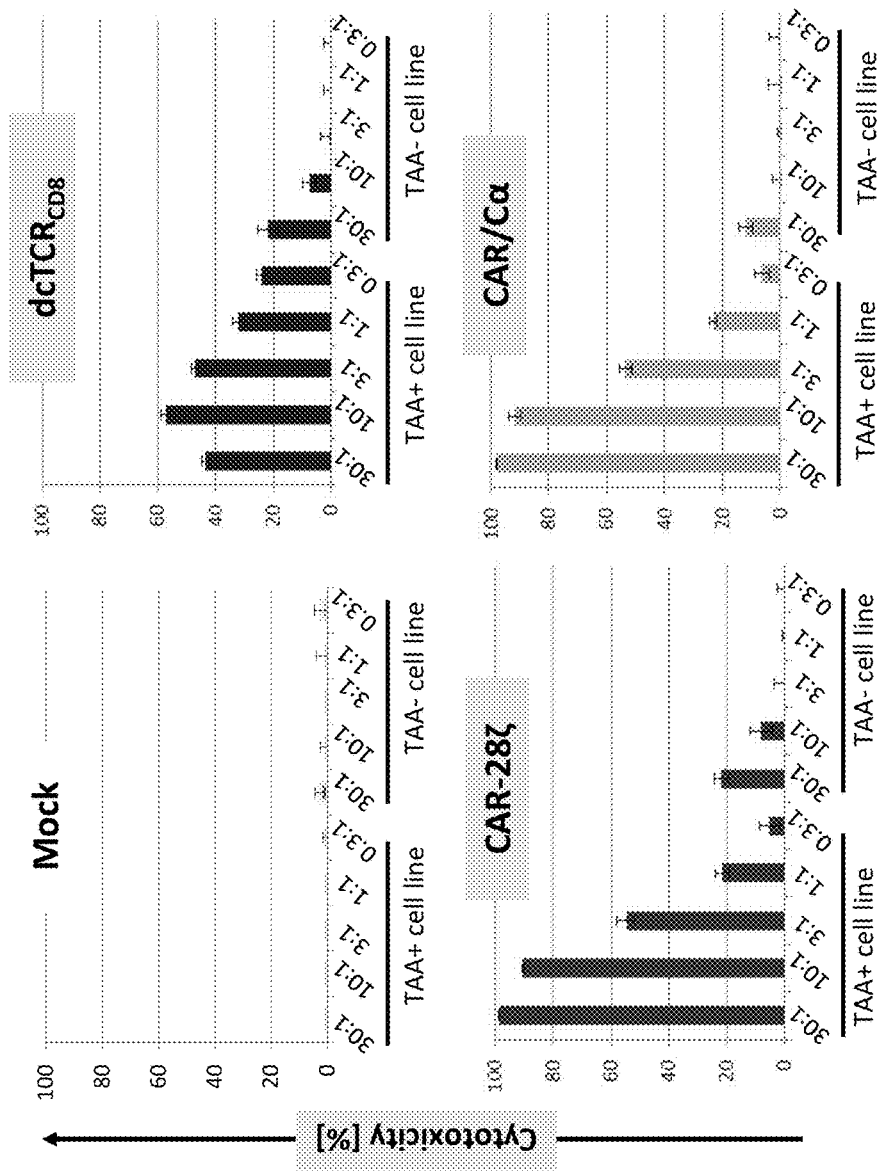

FIG. 13: Tumor cell lysis mediated by different CLDN-6 targeting receptor formats. Preactivated CD8+ T cells were transfected with CAR or TCR RNAs and cocultured 20 h later together with CLDN6-positive or CLDN6– negative tumor cell lines PA1 and MDA-MB-231-Luc at different E:T ratios. Specific lysis was analyzed by luciferase-based cytotoxicity assay after 4 h coculture.

Figure 14:
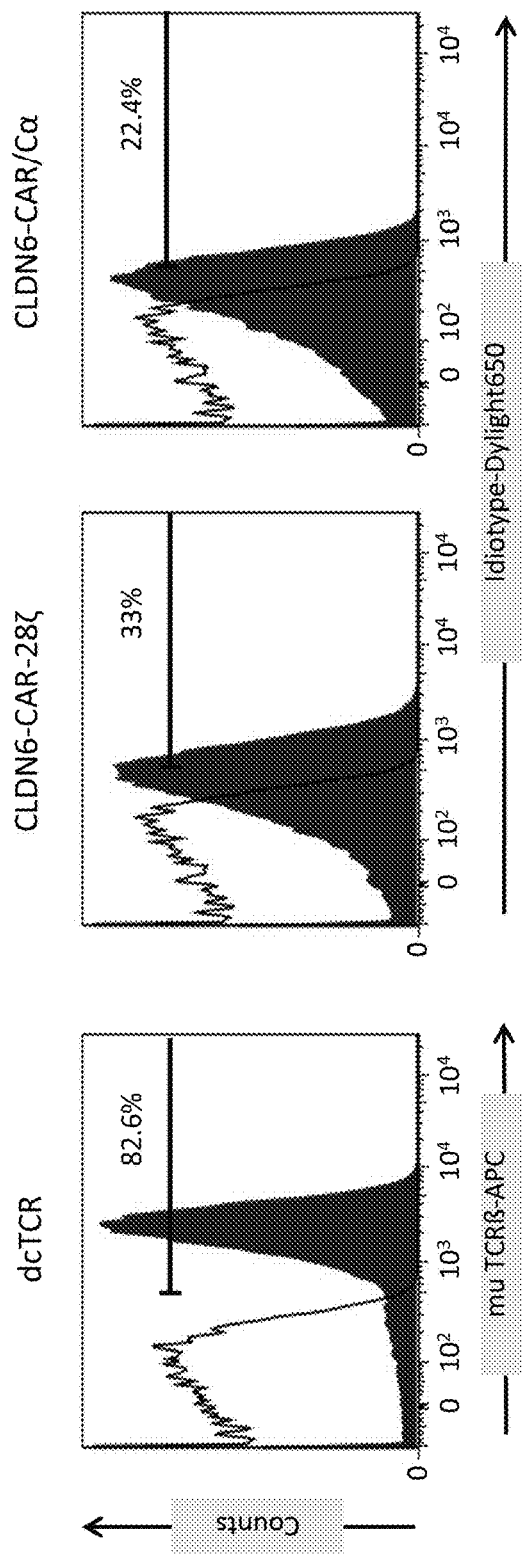
Figure 14:
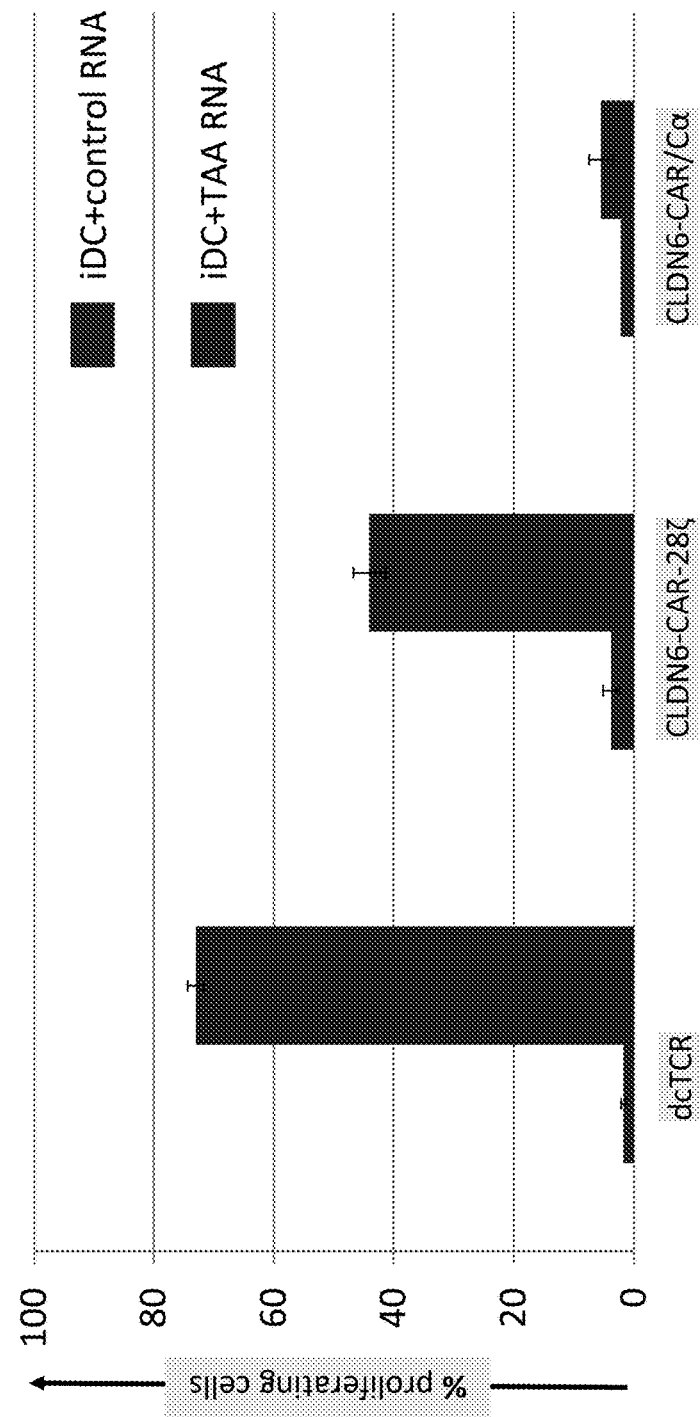
Figure 14:
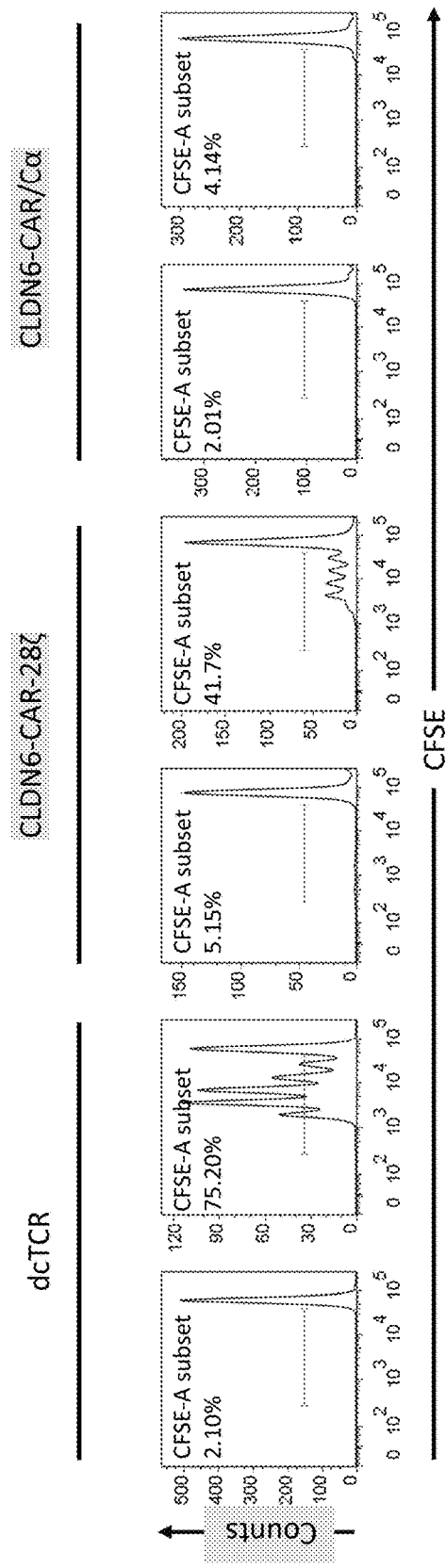

FIG. 14: Antigen-specific proliferation mediated by CLDN6-specific CAR in response to CLDN6-expressing target cells. CD8+ T cells were transfected with 20 µg TCR or CAR RNA, labeled with CFSE and cocultured with autologous iDC transfected with CLDN6 or control RNA for 4 days. A) TCR/CAR surface expression was analyzed by flow cytometry after staining with a murine APC-conjugated TCRß-specific or a Dylight650-conjugated idiotype-specific antibody. Specific proliferation was analyzed by flow cytometry based on the dilution of the CFSE proliferation dye.

Figure 15:
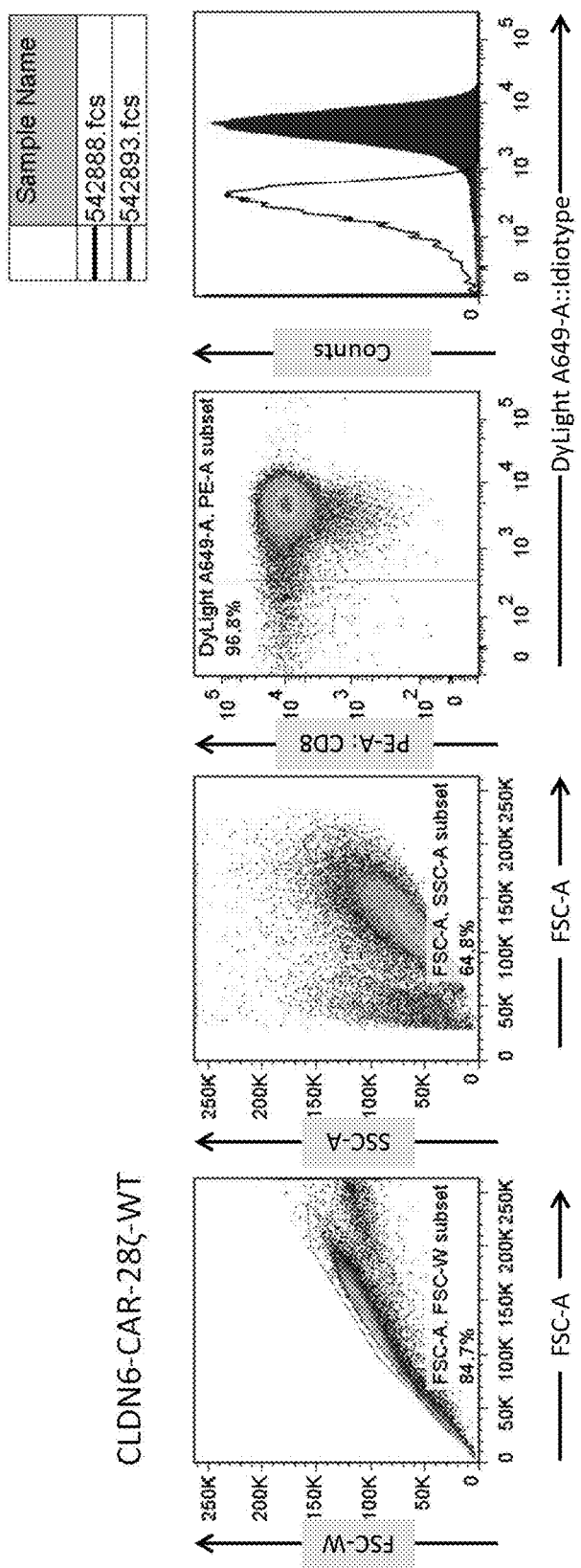
Figure 15:
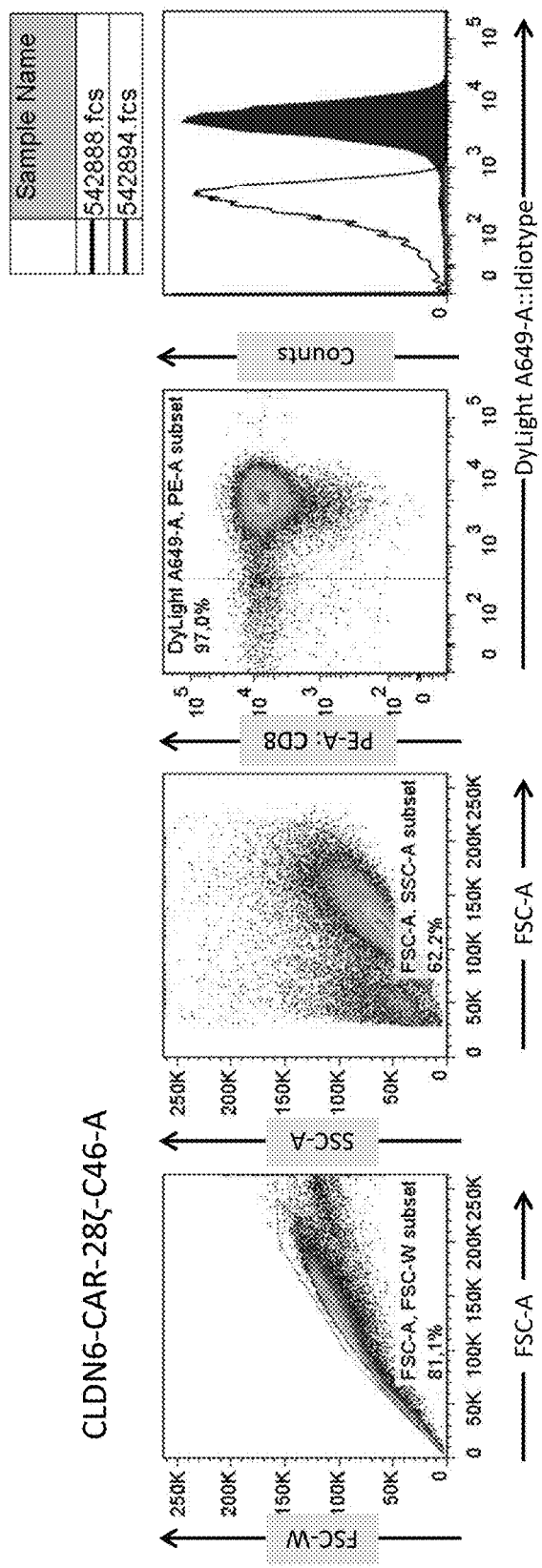
Figure 15:
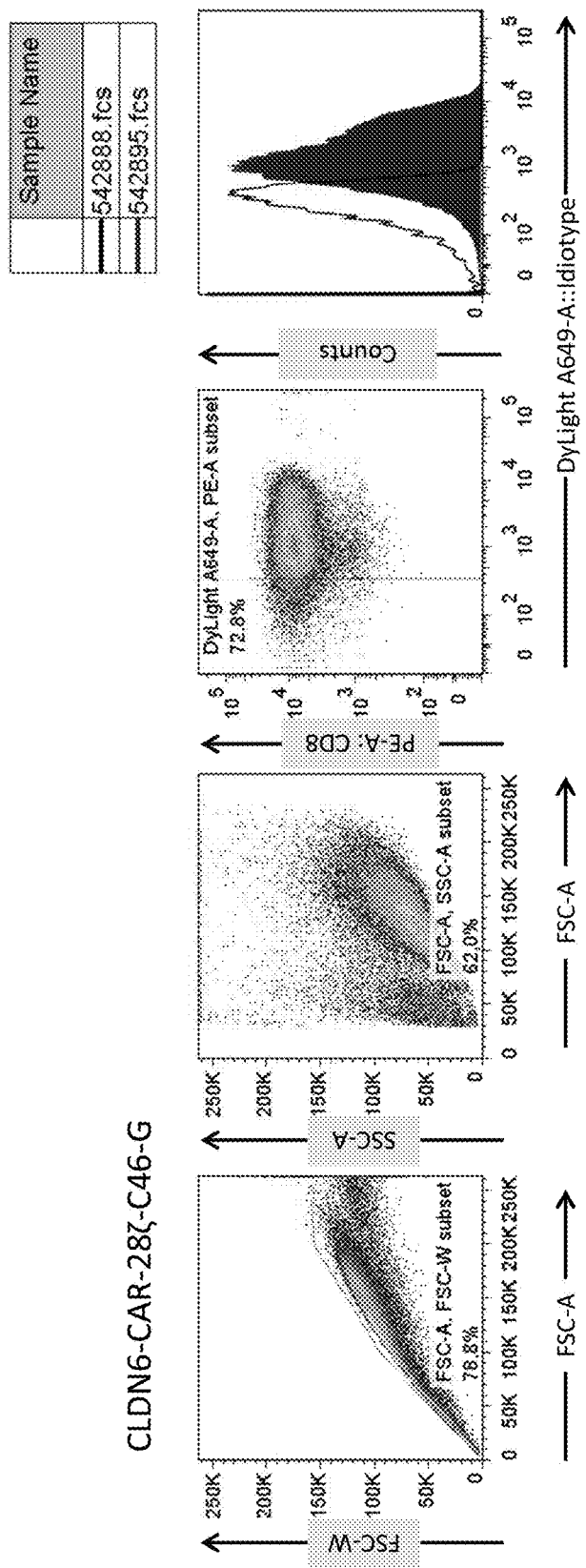
Figure 15:
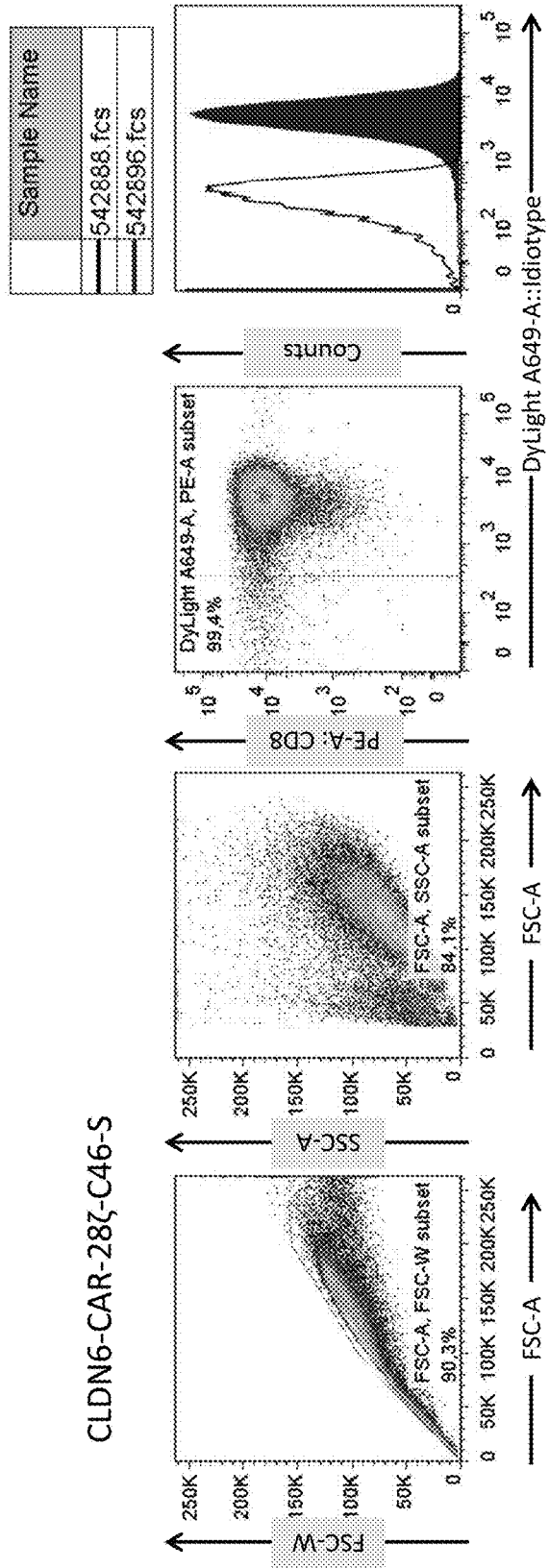

FIG. 15: Surface expression of different mutants of CLDN6-CAR-28ζ constructs with mutated cysteine 46 on preactivated CD8+ T cells. CD8+ T cells were preactivated with OKT3 and transfected with 20 µg CAR RNA. 20 h after electroporation cells were stained with a PE-conjugated anti-CD8 antibody and an idiotype-specific antibody labeled with Dylight650. Cells were gated on singlets and lymphocytes.

Figure 16:
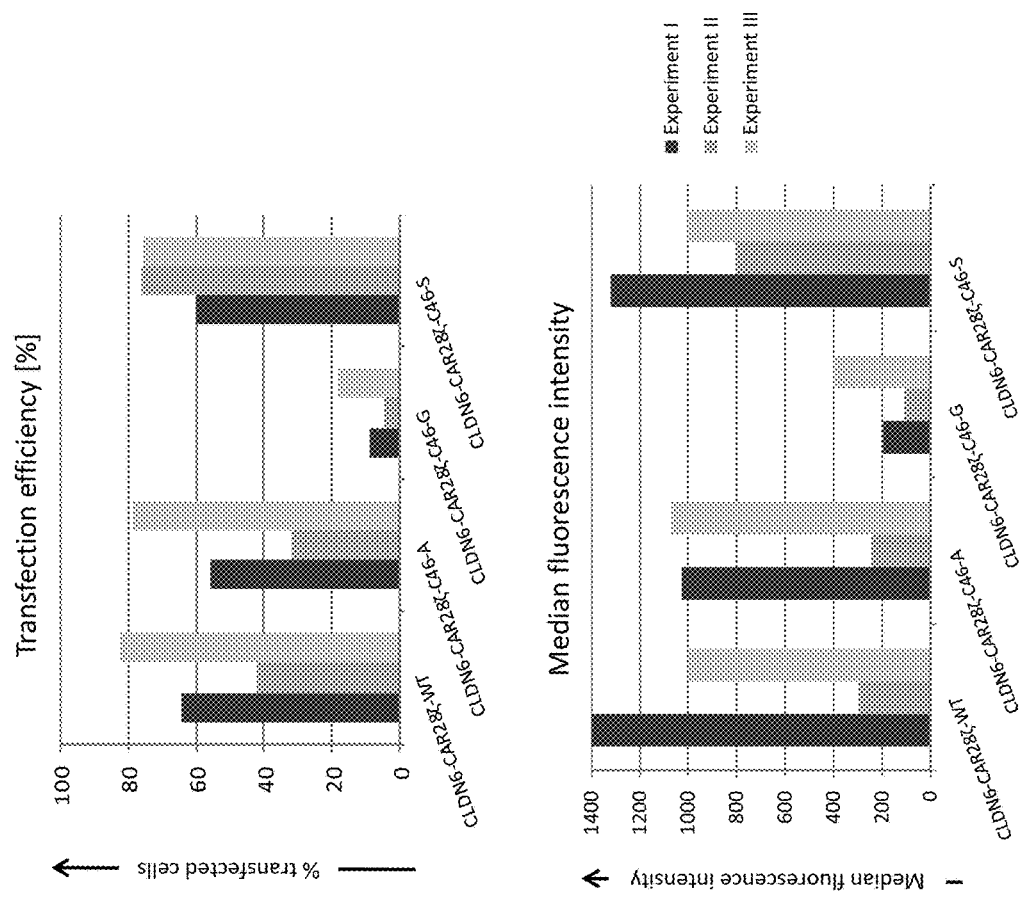
Figure 17:
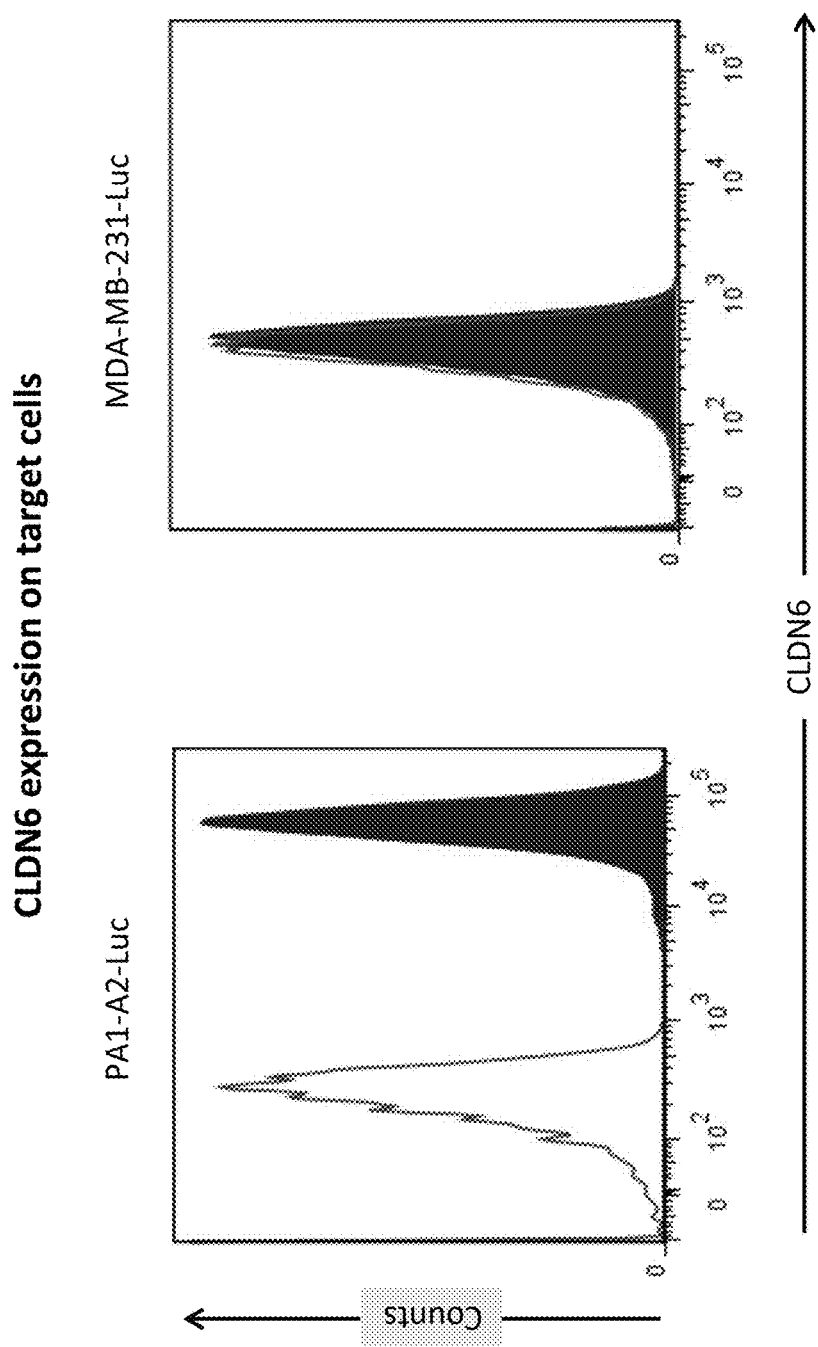
Figure 17:
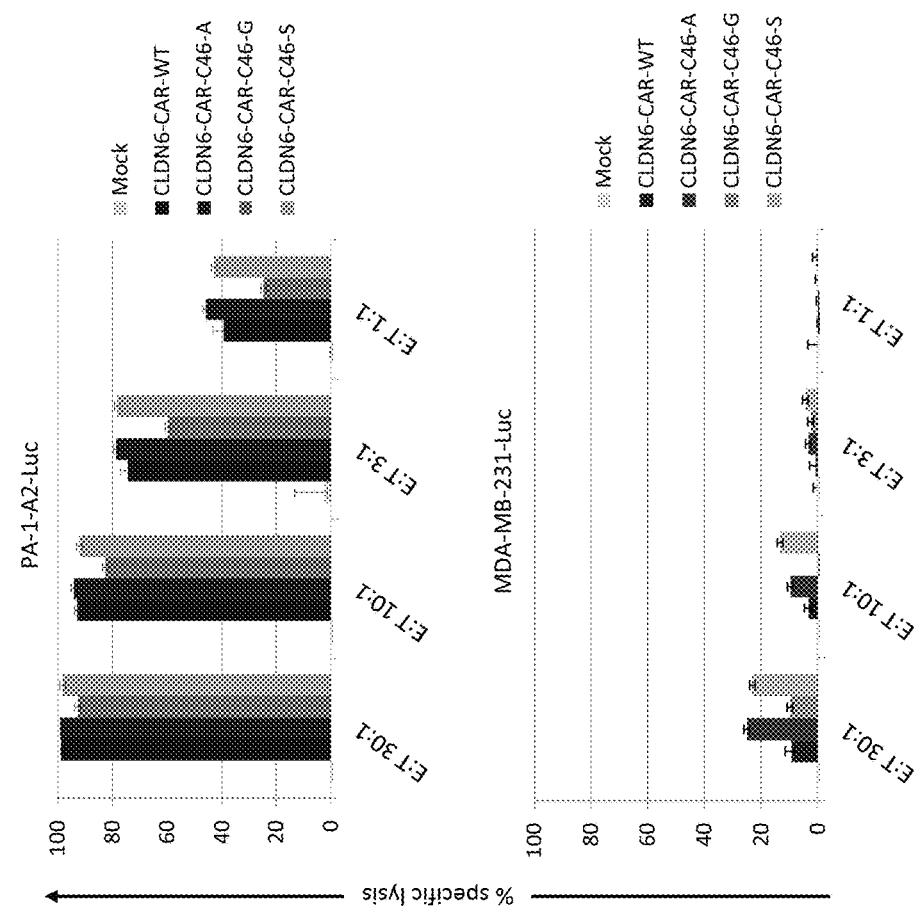
Figure 17:
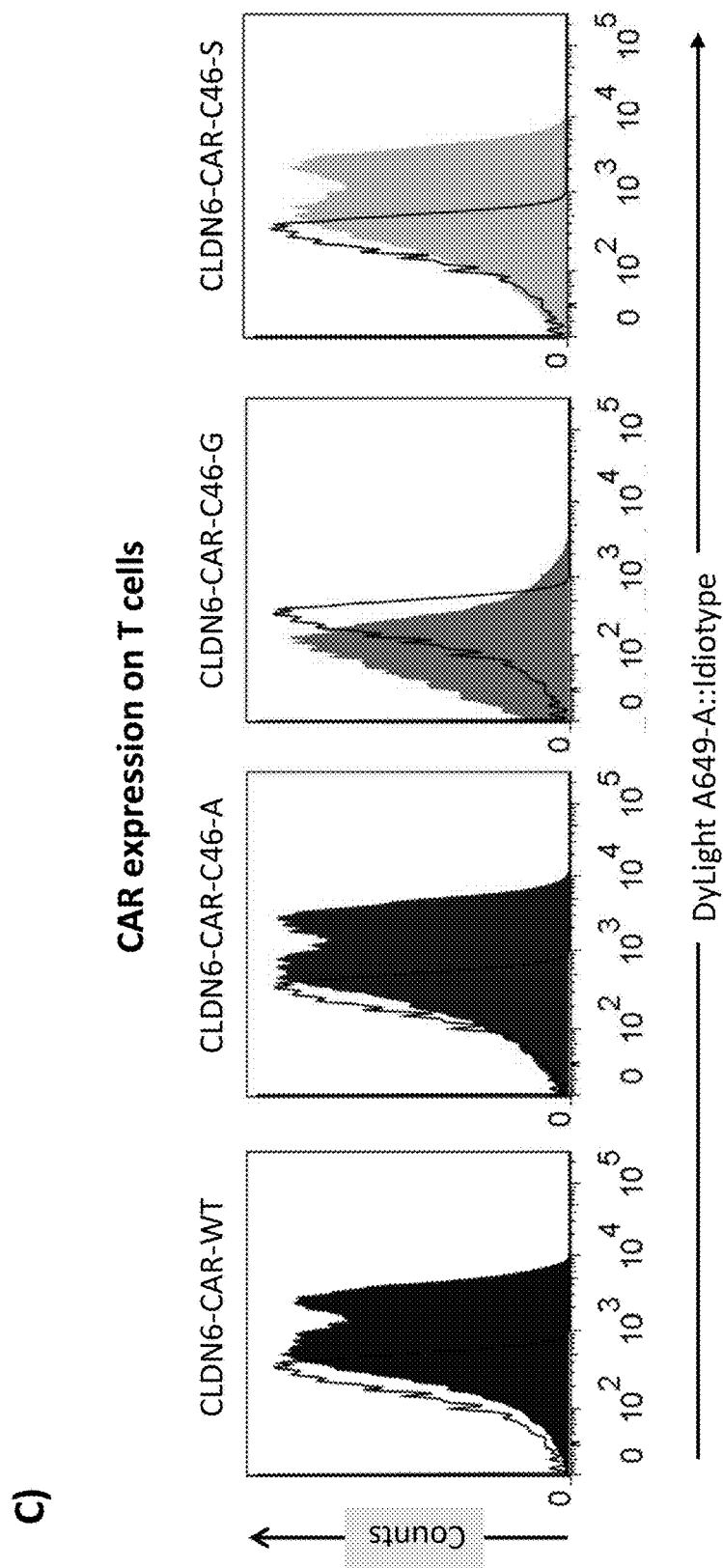

FIG. 16: Surface expression of different mutants of CAR-28K constructs with mutated cysteine 46 on preactivated CD8+ T cells of three different donors. CD8+ T cells were preactivated with OKT3 and transfected with 20 µg CAR RNA. 20 h after electroporation cells were stained with an idiotype-specific antibody labeled with Dylight650. Cells were gated on CAR-expressing CD8+ T lymphocytes. The results of three independent experiments are shown. Top: the percentage of CAR+/CD8+ T cells is shown; bottom: the mean fluorescence intensity of CAR-positive CD8+ T cells is shown;

FIG. 17: Specific tumor cell lysis mediated by different mutants of CLDN6-CAR-28ζ constructs with mutated cysteine 46. A) The CLDN6 surface expression on target cell lines was analyzed after staining with a Alexa647-conjugated CLDN6-specific antibody by flow cytometry. B) Preactivated CD8+ T cells were transfected with 20 µg CAR RNA and cocultured 20 h later together with CLDN6-positive (PA1) or CLDN6− negative (MDA-MB-231-Luc-Tomato) tumor cell lines at different E:T ratios. Specific lysis was analyzed by luciferase-based cytotoxicity assay after 4 h coculture. C) CAR surface expression on T cells was analyzed after staining with a fluorochrome-conjugated CD8-specific and an idiotype-specific antibody by flow cytometry.

Figure 18:
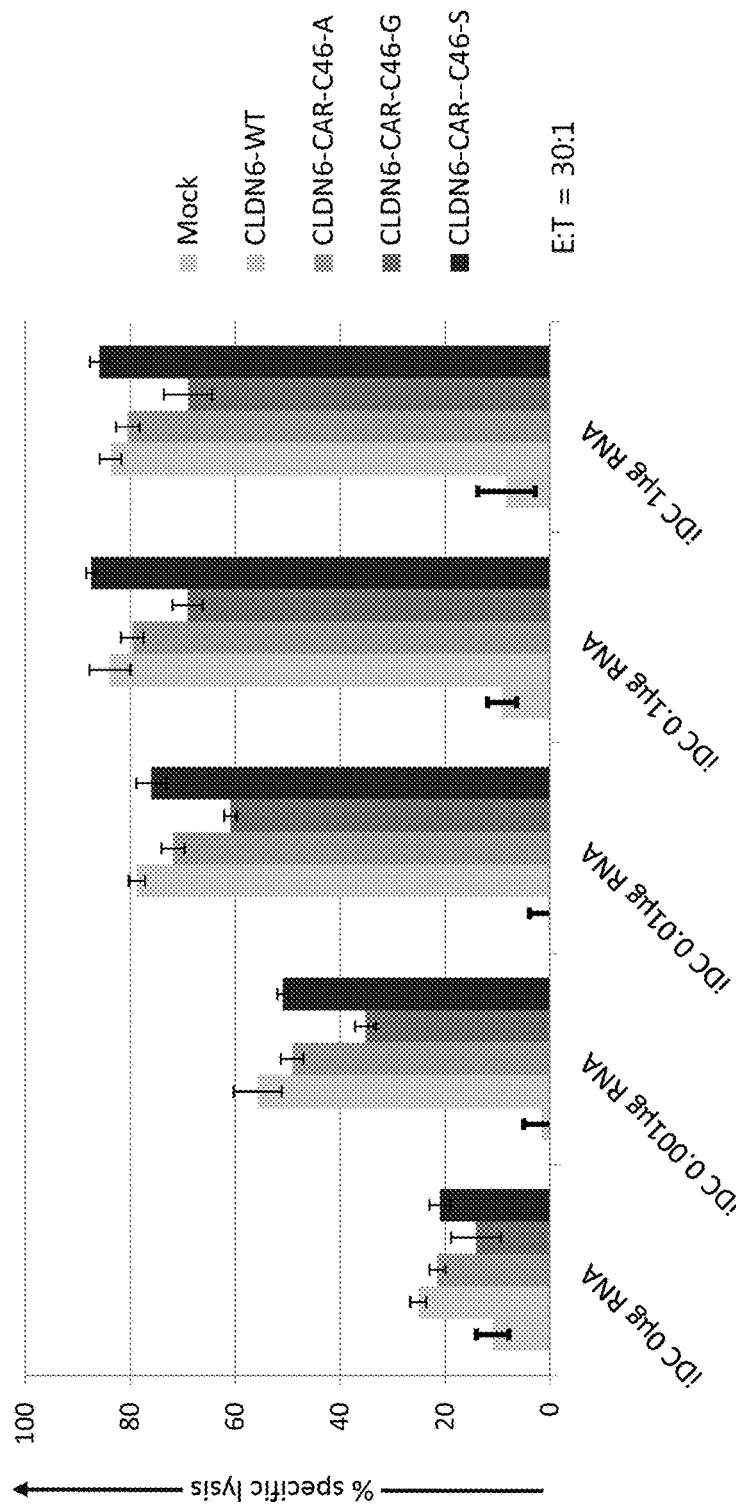
Figure 18:
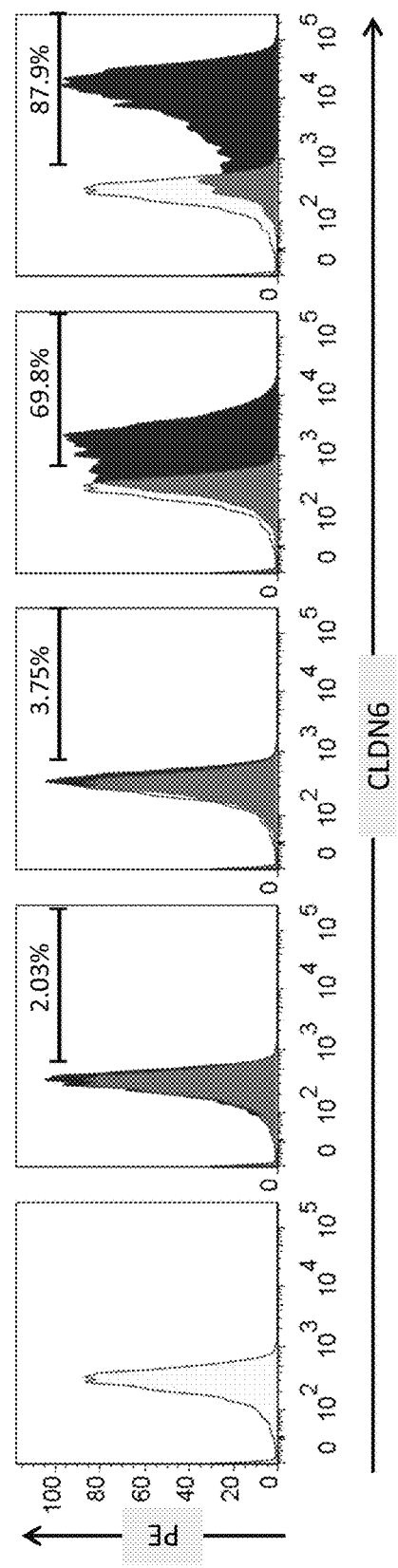

FIG. 18: Dose-dependent lysis of target cells mediated by different mutants of CLDN6-CAR-28ζ constructs with mutated cysteine 46. A) Preactivated CD8+ T cells were transfected with 20 µg CAR RNA and cocultured 20 h later together with autologous iDC transfected with titrated amounts of CLDN6-RNA (E:T=30:1). B) The CLDN6 surface expression on transfected iDCs was analyzed after staining with a Alexa647-conjugated CLDN6-specific antibody by flowcytometry.

Figure 19:
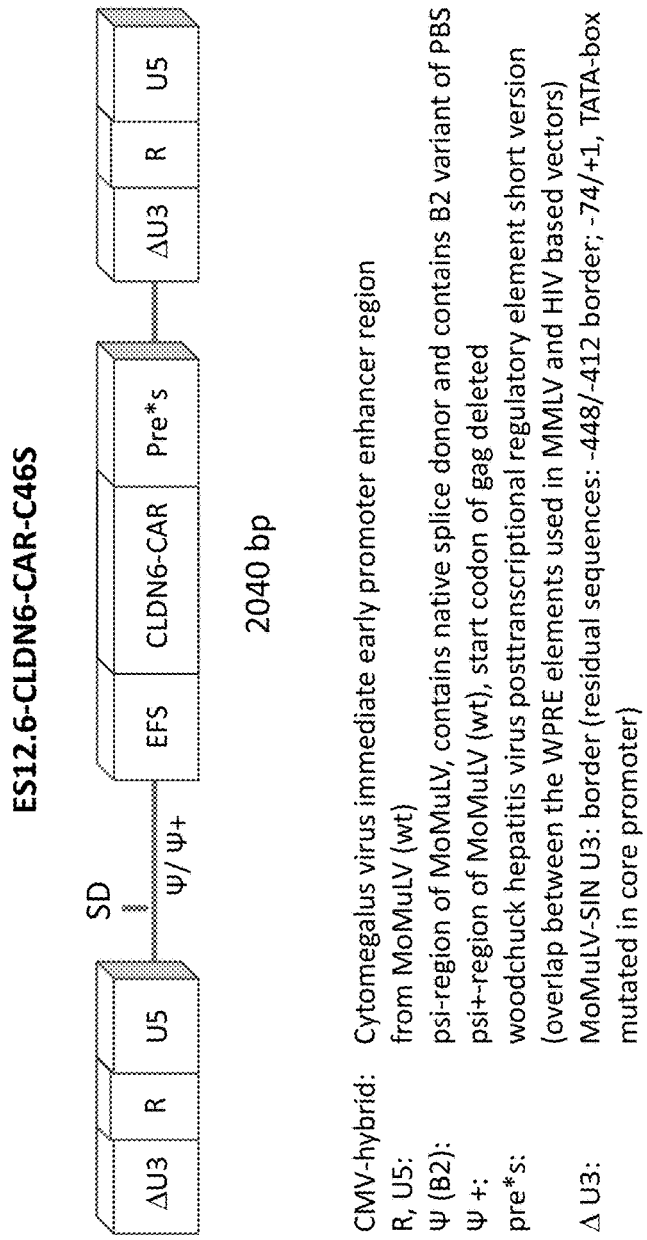

FIG. 19: Schematic representation of the retroviral SIN construct used for stable CAR expression. The plasmid pES12.6-CLDN6-CAR-C46S was used for transient generation of GALV-enveloped SIN-vector using HEK293T cells.

Figure 20:
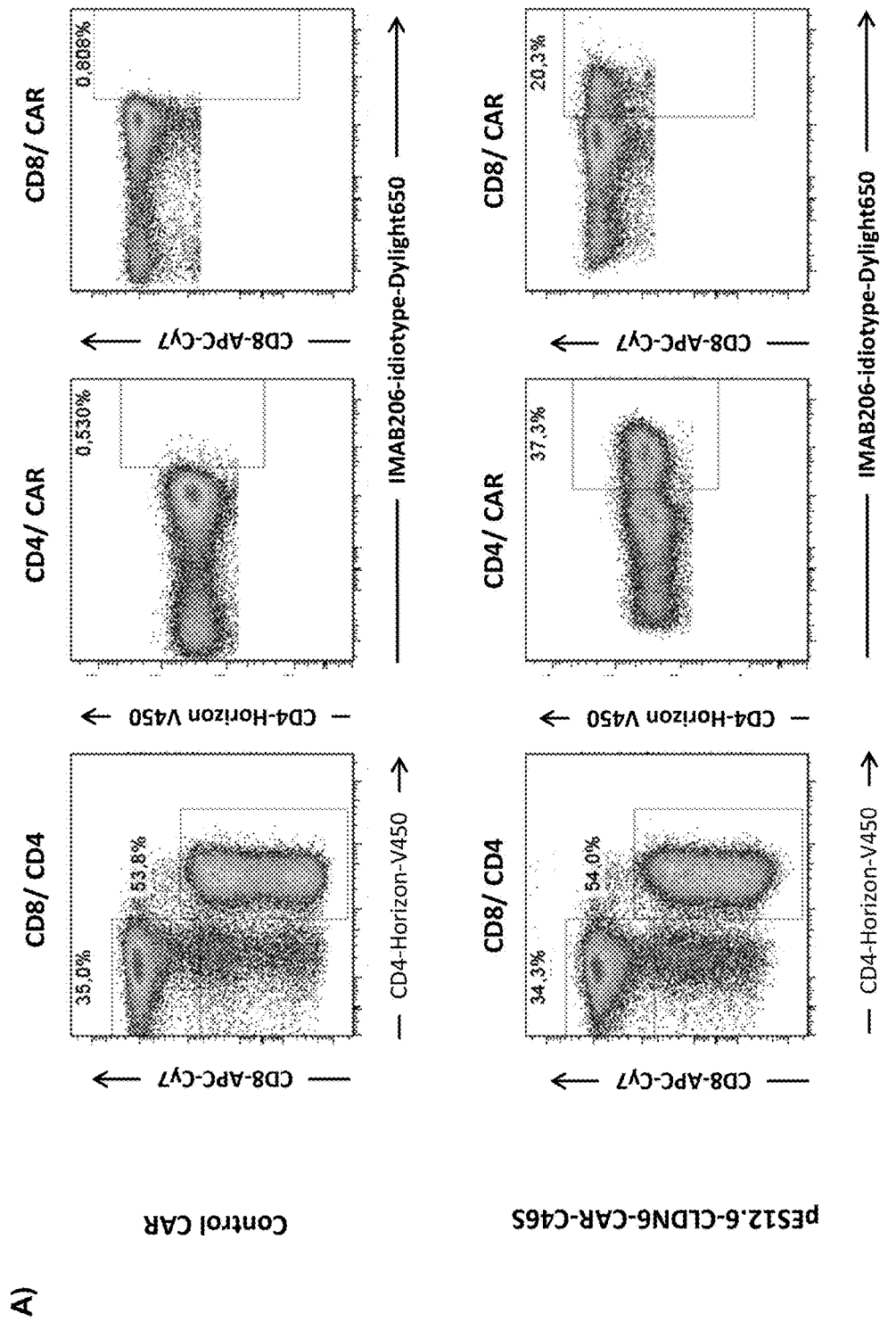
Figure 20:
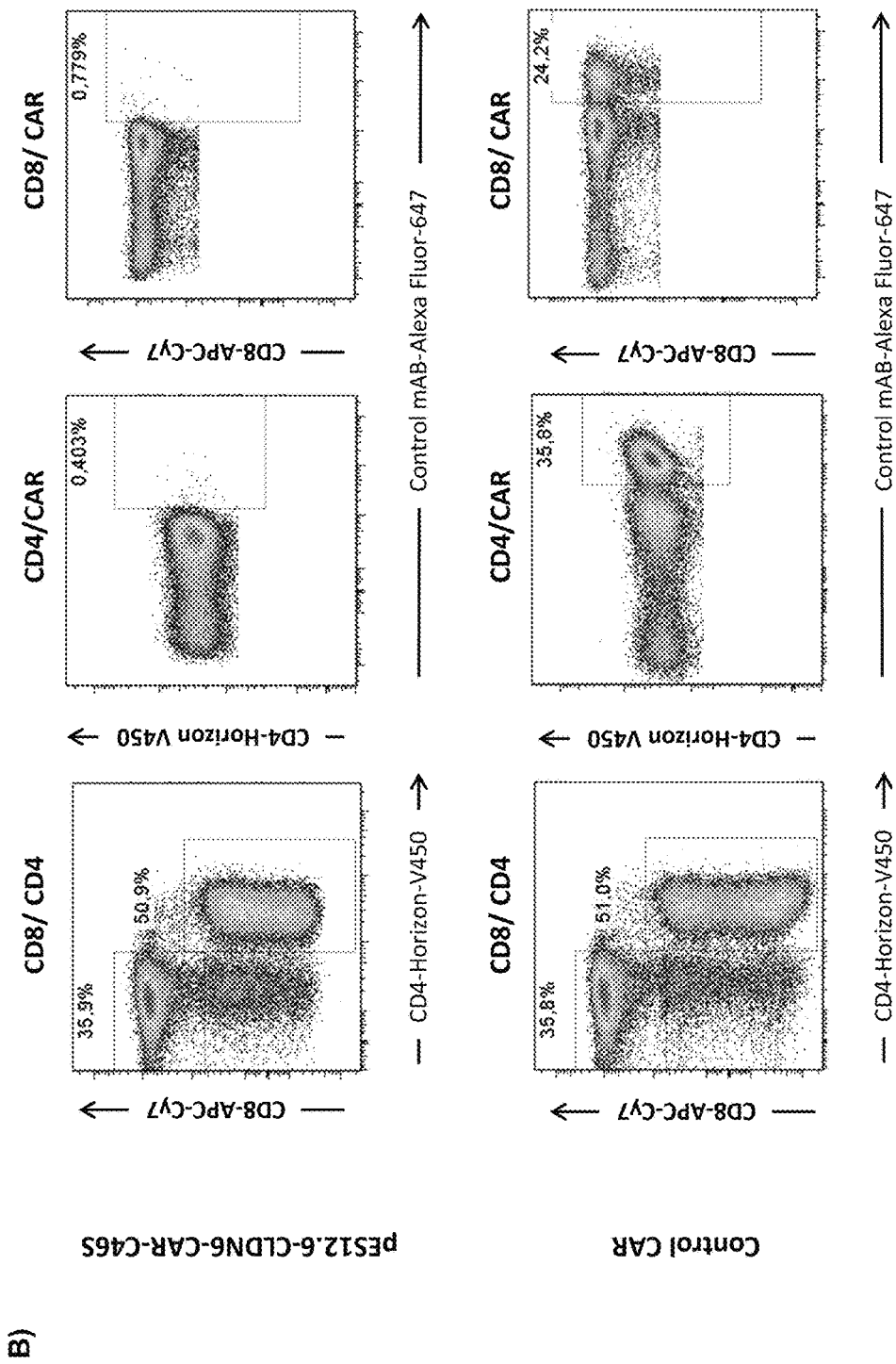

FIG. 20: Detection of CLDN6-CAR and CAR against an unrelated tumor antigen on transduced human T cells used for adoptive transfer into NSG mice. Cells were stained with fluorochrome-conjugated antibodies (BD Biosciences) directed against CD8 and CD4 as well as with idiotype-specific antibodies directed against the respective scFv part of the CLDN6-CAR (anti-IMAB206, Ganymed Pharmaceuticals AG) and the CAR against an unrelated tumor antigen, respectively. Cells were gated on single CD8$^+$ or CD4$^+$ lymphocytes. Transduced T cells were used for adoptive cell transfer in OV90-SC12-engrafted NSG mice. The transduction rate for the CLDN6-CAR and the CAR against an unrelated tumor antigen was about 37% of CD4$^+$ and 20% of CD8$^+$ as well as 36% of CD4$^+$ and 24 of CD8$^+$ cells, respectively. Graphs are displayed in logarithmic scale.

FIG. 21: Anti-tumoral activity of CLDN6-CAR transduced T cells in an ovarian carcinoma model. $1\times10^7$ human OV90-SC12 tumor cells (ATCC CRL11732) were injected subcutaneously into NSG mice (10 mice/group). After 4 days, the mice were treated with a single intravenous injection of $1\times10^7$ CD3/CD28 bead stimulated, retrovirally transduced human T cells (about 37% of CD4 and 20% of CD8 were CLDN6-CAR positive). A) Scheme of the experimental set up. B) Delay of tumor growth in CLDN6-CAR treated mice compared to control groups (no T cells, untransduced T cells, and T cells transduced with CAR against an unrelated tumor antigen). Tumor monitoring by volume measurements and analysis of peripheral blood was performed weekly. Results are expressed as mean tumor volume ±SEM with n=10 mice for all groups. Tumor volume was calculated using the following formula: V=½*(length*square width). The plot for the CLDN6-CAR treated mice is significantly different from the control treatment group for t=31 days (*ANOVA, P<0.05). C) Tumor-growth curves of the individual mice of each group are shown. Please note, 2 mice in the unrelated tumor antigen group had to be sacrificed on day 24 due to high tumor burden (marked with +).

Figure 22:
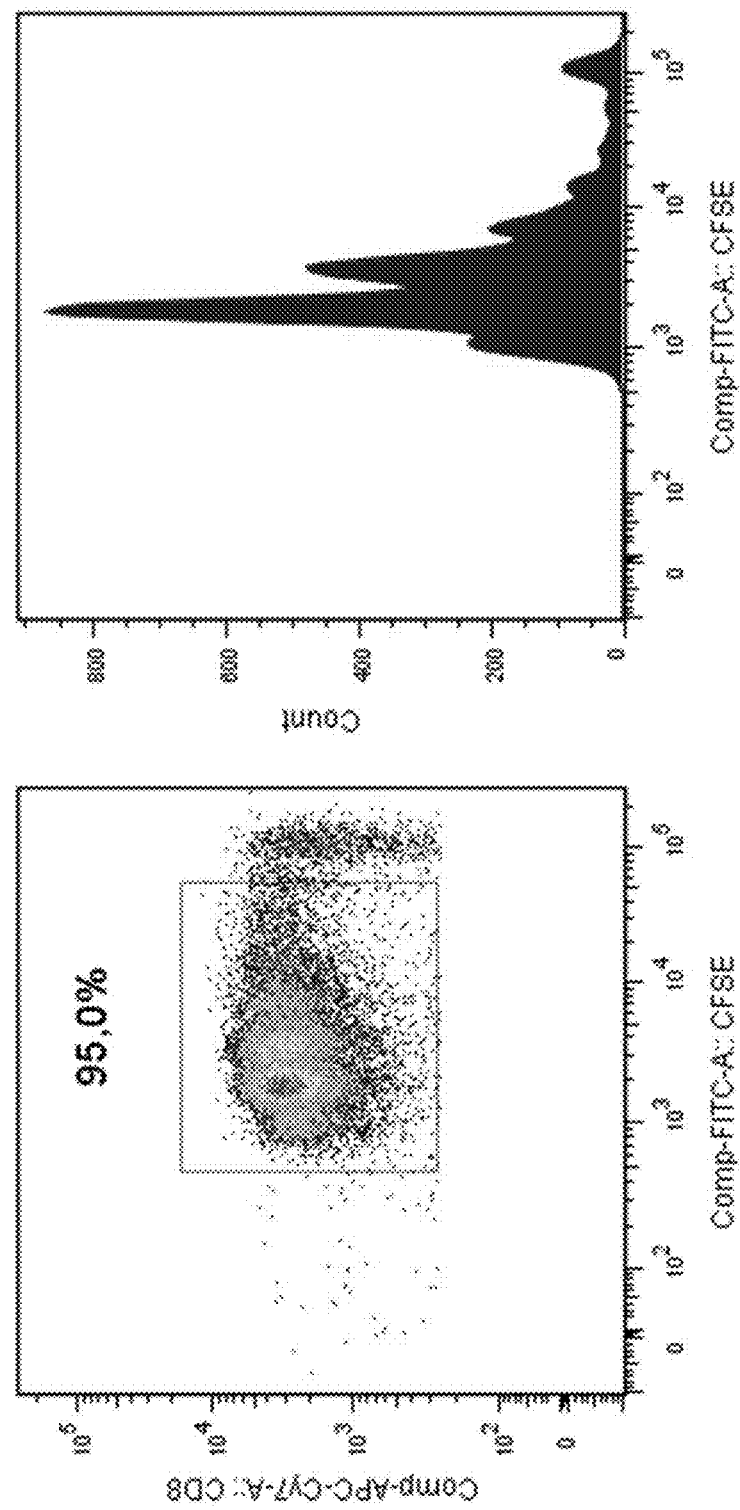
Figure 22:
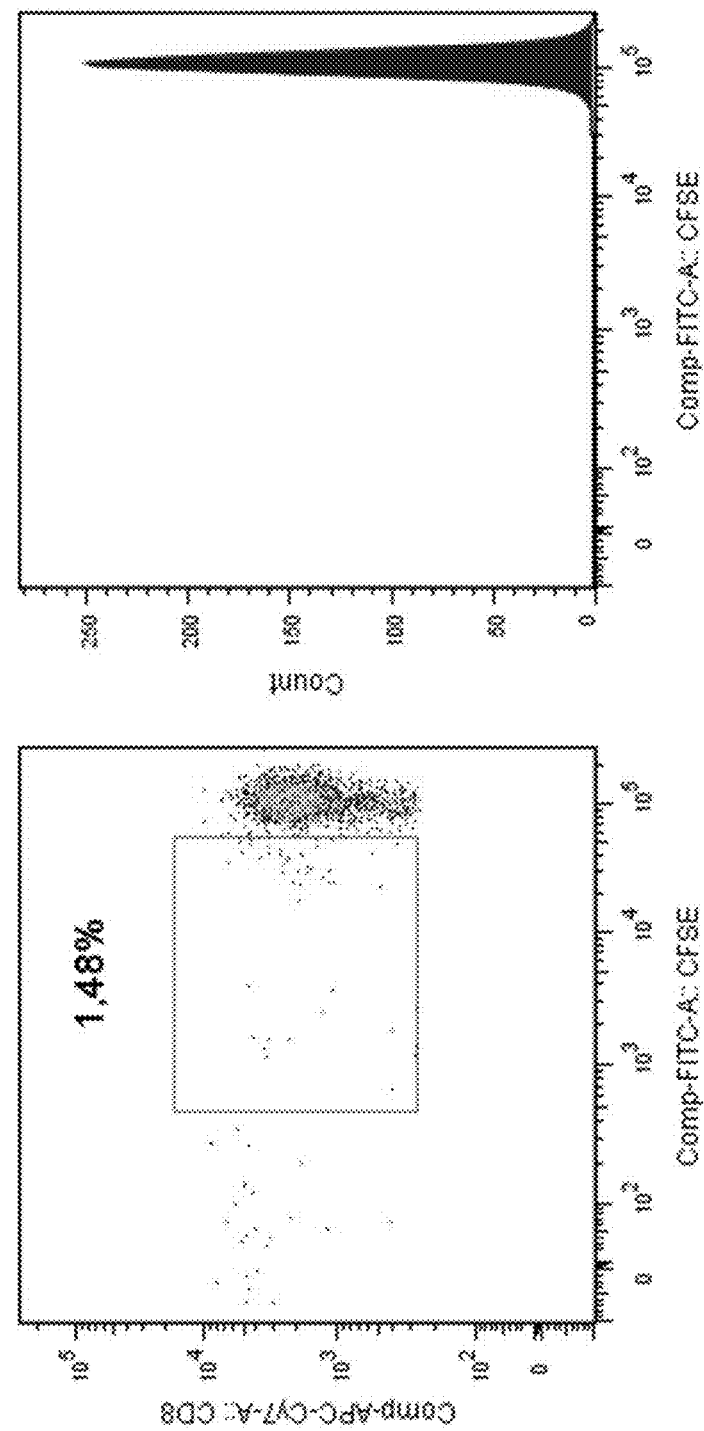

FIG. 22. Proliferation of CAR T cells after co-culture with CLND6 expressing iDCs. CD8$^+$ T cells were transfected with IVT-RNA encoding a CAR directed against A) CLDN6 or B) an unrelated tumor antigen as negative control, labeled with CFSE (carboxyfluorescein succinimidyl ester) and cocultured with CLDN6-transfected autologous iDCs for 4 days. Proliferation of CAR T cells was analyzed based on the dilution of CFSE by flowcytometry. Cells were gated on single living CD8$^+$ T lymphocytes.

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

Cell Lines and Reagents

The human chronic myeloid leukemia cell line K562 (Lozzio, C. B. & Lozzio, B. B (1975), Blood 45, 321-334) was cultured under standard conditions. K562 cells stably transfected with HLA-A*0201 (Britten, C. M. et al. (2002), J. Immunol. Methods 259, 95-110) (referred to e.g. as K562-A*0201) were used for validation assays. The primary human newborn foreskin fibroblast cell line CCD-1079Sk (ATCC No. CRL-2097) was cultured according to the manufacturers' instructions.

The human CLDN6 expressing ovarian carcinoma cell line OV-90-SC12 was used for in vivo validation of the CLDN6-CAR.

The culture medium for PA-1-SC12_A0201_luc_gfp_F7 is composed of 86% RPMI 1640+ Glutamax (Co. Gibco, Cat-No. 61870), 10% FCS (Co. Biochrome, Cat-No. S0615), 1% Sodium Pyruvate (100 mM) (Co. Gibco, Cat-No. 11360), 1% MEM Non-Essential Amino Acids Solution (100×) (Co. Gibco, Cat-No. 11140), 2% Sodium Bicarbonate 7, 5% solution (Co. Gibco, Cat-No. 25080).

The culture medium for OV-90-SC12 is composed of 41.5% MCDB 105 (Co. Sigma Aldrich, Cat-No. M6395-1L), 41.5% Medium 199 (Co. Sigma Aldrich, Cat-No. M2154-500 mL), 15% FCS (Co. Biochrome, Cat-No. S0615), 2% Sodium Bicarbonate 7.5% solution (Co. Gibco, Cat-No. 25080).

The culture medium for SK-MEL-37 is composed of 90% DMEM+ Glutamax (Co. Gibco, Cat-No. 31966), 10% FCS (Co. Biochrome, Cat-No. S0615). The culture medium for MDA-MB-231_luc_tom is composed of 88% RPMI 1640+ Glutamax (Co. Gibco, Cat-No. 61870), 10% FCS (Co. Biochrome, Cat-No. S0615), 1% Sodium Pyruvate (100 mM) (Co. Gibco, Cat-No. 11360), 1% MEM Non-Essential Amino Acids Solution (100×) (Co. Gibco, Cat-No. 11140). Feeding and/or splitting of the cell lines was done every 2 to 3 days.

Peripheral Blood Mononuclear Cells (PBMCs), Monocytes and Dendritic Cells (DCs)

PBMCs were isolated by Ficoll-Hypaque (Amersham Biosciences, Uppsala, Sweden) density gradient centrifugation from buffy coats. HLA allelotypes were determined by PCR standard methods. Monocytes were enriched with anti-CD14 microbeads (Miltenyi Biotech, Bergisch-Gladbach, Germany). Immature DCs (iDCs) were obtained by differentiating monocytes for 5 days in cytokine-supplemented culture medium as described in Kreiter et al. (2007), Cancer Immunol. Immunother., CII, 56, 1577-87.

Peptides and Peptide Pulsing of Stimulator Cells

Pools of N- and C-terminally free 15-mer peptides with 11 amino acid overlaps corresponding to sequences of Claudin-6 or HIV-gag (referred to as antigen peptide pool) were synthesized by standard solid phase chemistry (JPT GmbH, Berlin, Germany) and dissolved in DMSO to a final concentration of 0.5 mg/ml. Nonamer peptides were reconstituted in PBS 10% DMSO. For pulsing stimulator cells were incubated for 1 h at 37° C. in culture medium using different peptide concentrations.

Vectors for In Vitro Transcription (IVT) of RNA

All constructs are variants of the previously described pST1-sec-insert-2βgUTR-A(120)-Sap1 plasmid (Holtkamp, S. et al. (2006), Blood 108, 4009-4017). To obtain plasmids encoding human TCR chains, cDNA coding for TCR-α or TCR-ß$_1$ and TCR-ß$_2$ constant regions were amplified from human CD8+ T cells and cloned into this backbone. For generation of plasmids encoding murine TCR chains, cDNAs coding for TCR-α, -β$_1$ and -β$_2$ constant regions were ordered from a commercial provider and cloned analogously (GenBank accession numbers M14506, M64239 and X67127, respectively). Specific V(D)J PCR products were introduced into such cassettes to yield full-length TCR chains (referred to as pST1-human/murineTCRαß-2ßgUTR-A(120)).

Analogously, individual HLA class I and II alleles cloned from PBMCs of donors and beta-2-microglobulin (B2M) cDNA from human DCs were inserted into this backbone (referred to as pST1-HLA class I/II-2ßgUTR-A(120) and pST1-B2M-2ßgUTR-A(120)).

Plasmids coding for pp65 antigen of CMV (pST1-sec-pp65-MITD-2ßgUTR-A(120)) and NY-ESO-I (pST1-sec-NY-ESO-1-MITD-2ßgUTR-A(120)) linked to a secretion signal (sec) and the MHC class I trafficking signal (MITD) were described previously (Kreiter, S. et al. (2008), J. Immunol. 180, 309-318). PLAC1 encoding plasmid pST1-sec-PLAC1-MITD-2ßgUTR-A(120) was generated by cloning a cDNA obtained from a commercial provider (GenBank accession number NM_021796) into the Kreiter et al. backbone. TPTE encoding plasmids pST1-αgUTR-TPTE-2ßgUTR-A(120) and pST1-αgUTR-TPTE-MITD-2ßgUTR-A(120) were generated by cloning a cDNA obtained from a commercial provider (GenBank accession number AF007118) into a variant of the Holtkamp et al. vector featuring an additional alpha-globin 5'-untranslated region.

Primers were purchased from Operon Biotechnologies, Cologne, Germany.

Generation of In Vitro Transcribed (IVT) RNA and Transfer into Cells

Generation of IVT RNA was performed as described previously (Holtkamp, S. et al. (2006), Blood 108, 4009-4017) and added to cells suspended in X-VIVO 15 medium (Lonza, Basel, Switzerland) in a pre-cooled 4-mm gap sterile electroporation cuvette (Bio-Rad Laboratories GmbH, Munich, Germany). Electroporation was performed with a Gene-Pulser-II apparatus (Bio-Rad Laboratories GmbH, Munich, Germany) (T cells: 450 V/250 µF; IVSB T cells: 350 V/200 µF; SupT1 (ATCC No. CRL-1942): 300 V/200 µF; human DC: 300 V/150 µF; K562: 200 V/300 µF).

In Vivo Priming of T Cells by Intranodal Immunization of HLA A2.1/DR1 Mice with IVT RNA T cells of A2/DR1 mice (Pajot A. et al. (2004), Eur. J. Immunol. 34, 3060-69) were primed in vivo against the antigen of interest by repetitive intranodal immunization using antigen-encoding IVT RNA (Kreiter S. et al. (2010), Cancer Research 70, 9031-40). For intranodal immunizations, mice were anesthetized with xylazine/ketamine. The inguinal lymph node was surgically exposed, 10 µL RNA (20 µg) diluted in Ringer's solution and Rnase-free water were injected slowly using a single-use 0.3-ml syringe with an ultrafine needle (31 G, BD Biosciences), and the wound was closed. After six immunization cycles the mice were sacrificed and spleen cells were isolated.

Harvest of Spleen Cells

Following their dissection under sterile conditions, the spleens were transferred to PBS containing falcon tubes. The spleens were mechanically disrupted with forceps and the cell suspensions were obtained with a cell strainer (40 µm). The splenocytes were washed with PBS centrifuged and resuspended in a hypotonic buffer for lysis of the erythrocytes. After 5 min incubation at RT, the reaction was stopped by adding 20-30 ml medium or PBS. The spleen cells were centrifuged and washed twice with PBS.

Single-Cell Sorting of Antigen-Specific CD8+ T Cells after CD137 Staining

For antigen-specific restimulation $2.5 \times 10^6$/well spleen cells from immunized A2/DR1 mice were seeded in a 24-well plate and pulsed with a pool of overlapping peptides encoding the antigen of interest or a control antigen. After 24 h incubation cells were harvested, stained with a FITC-conjugated anti-CD3 antibody, a PE-conjugated anti-CD4 antibody, a PerCP-Cy5.5-conjugated anti-CD8 antibody and a Dylight-649-conjugated anti-CD137 antibody. Sorting was conducted on a BD FACS Aria flow cytometer (BD Biosciences). Cells positive for CD137, CD3 and CD8 were sorted, one cell per well was harvested in a 96-well V-bottom-plate (Greiner Bio-One) containing human CCD-1079Sk cells as feeder cells, centrifuged at 4° C. and stored immediately at −80° C.

RNA Extraction, SMART-Based cDNA Synthesis and Unspecific Amplification from Sorted Cells RNA from sorted T cells was extracted with the RNeasy Micro Kit (Qiagen, Hilden, Germany) according to the instructions of the supplier. A modified BD SMART protocol was used for cDNA synthesis: BD PowerScript Reverse Transcriptase (BD Clontech, Mountain View, Calif.) was combined with oligo(dT)-T-primer long for priming of the first-strand synthesis reaction and TS-short (Eurogentec S. A., Seraing, Belgium) introducing an oligo(riboG) sequence to allow for creation of an extended template by the terminal transferase activity of the reverse transcriptase and for template switch (Matz, M. et al. (1999) Nucleic Acids Res. 27, 1558-1560). First strand cDNA synthesized according to the manufacturer's instructions was subjected to 21 cycles of amplification with 5 U PfuUltra Hotstart High-Fidelity DNA Polymerase (Stratagene, La Jolla, Calif.) and 0.48 µM primer TS-PCR primer in the presence of 200 µM dNTP (cycling conditions: 2 min at 95° C. for, 30 s at 94° C., 30 s at 65° C., 1 min at 72° C. for, final extension of 6 min at 72° C.). Successful amplification of TCR genes was controlled with either human or murine TCR-β constant region specific primers and consecutive clonotype-specific human or murine Vα-/Vß-PCRs were only performed if strong bands were detected.

First strand cDNA for the amplification of HLA class I or II sequences was synthesized with SuperScriptII Reverse Transcriptase (Invitrogen) and Oligo(dT) primer with 1-5 µg RNA extracted from patient-derived PBMCs.

Design of PCR Primers for TCR and HLA Amplification

For design of human TCR consensus primers, all 67 TCR-VB and 54 TCR-Vα genes (open reading frames and pseudogenes) as listed in the ImMunoGeneTics (IMGT) database (http://www.imgt.org) together with their corresponding leader sequences were aligned with the BioEdit Sequence Alignment Editor (e.g. http://www.bio-soft.net). Forward primers of 24 to 27 bp length with a maximum of 3 degenerated bases, a GC-content between 40-60% and a G or C at the 3' end were designed to anneal to as many leader sequences as possible and equipped with a 15 bp 5' extension featuring a rare restriction enzyme site and Kozak sequence. Reverse primers were designed to anneal to the first exons of the constant region genes, with primer TRACex1_as binding to sequences corresponding to amino acids 7 to 16 of Cα and TRBCex1_as to amino acids (aa) 8 to 16 in Cβ1 and Cβ2. Both oligonucleotides were synthesized with a 5' phosphate. Primers were bundled in pools of 2-5 forward oligos with identical annealing temperature.

This strategy was replicated for the design of murine TCR consensus primers, aligning 129 listed TCR-Vα and 35 listed TCR-Vβ genes. Reverse primers mTRACex1_as and mTRBCex1_as are homologous to sequences corresponding to as 24 to 31 and 8 to 15, respectively.

HLA consensus primers were designed by aligning all HLA class I and II sequences listed on the Anthony Nolan Research Institute website (www.anthonynolan.com) with the BioEdit Sequence Alignment Editor. Forward primers of 23 to 27 bp length with a maximum of 3 degenerated but code-preserving bases annealing to as many as possible HLA sequences of one locus were equipped with a 5'-phosphate and Kozak sequence extension. Reverse primers were designed analogously but without introduction of wobble bases and equipped with a 14 bp 5'-extension encoding an AsiSI restriction enzyme site.

PCR Amplification and Cloning of V(D)J Sequences 3-6 μl of preamplified cDNA from isolated T cells was subjected to 40 cycles of PCR in the presence of 0.6 μM Vα-/Vβ-specific oligo pool, 0.6 μM Cα- or Cβ-oligo, 200 μM dNTP and 5 U Pfu polymerase (cycling conditions: 2 min at 95° C., 30 s at 94° C., 30 s annealing temperature, 1 min at 72° C., final extension time of 6 min at 72° C.). PCR products were analyzed using Qiagen's capillary electrophoresis system. Samples with bands at 400-500 bp were size fractioned on agarose gels, the bands excised and purified using a Gel Extraction Kit (Qiagen, Hilden, Germany). Sequence analysis was performed to reveal the sequence of both the V(D)J domain and β constant region, as TRBCex1_as and mTRBCex1_as primer, respectively, match to both TCR constant region genes β1 and β2 in human and mouse, respectively. DNA was digested and cloned into the IVT vectors containing the appropriate backbone for a complete TCR-α/β chain.

Flow Cytometric Analyses

Cell surface expression of transfected TCR genes was analyzed by flow cytometry using PE-conjugated anti-TCR antibody against the appropriate variable region family or the constant region of the TCR β chain (Beckman Coulter Inc., Fullerton, USA) and FITC-/APC-labeled anti-CD8/-CD4 antibodies (BD Biosciences). Cell surface expression of transfected CARs was analyzed using a Dylight-650-conjugated idiotype-specific antibody (Ganymed Pharmaceuticals) recognizing the scFv fragment contained in all CLDN6-CAR constructs. HLA antigens were detected by staining with FITC-labeled HLA class II-specific (Beckman Coulter Inc., Fullerton, USA) and PE-labeled HLA class I-specific antibodies (BD Biosciences). CLDN6 surface expression on target cells was analyzed by staining with an Alexa-Fluor647-conjugated CLDN6-specific antibody (Ganymed Pharmaceuticals). Flow cytometric analysis was performed on a FACS CANTO II flow cytometer using the FACS Diva software (BD Biosciences).

Luciferase Cytotoxicity Assay

For assessment of cell-mediated cytotoxicity a bioluminescence-based assay was established as an alternative and optimization to $^{51}$Cr release. In contrast to the standard chromium release assay, this assay measures lytic activity of effector cells by calculating the number of viable luciferase expressing target cells following coincubation. The target cells were stably or transiently transfected with the luciferase gene coding for the firefly luciferase from firefly Photinus pyralis (EC 1.13.12.7). Luciferase is an enzyme catalyzing the oxidation of luciferin. The reaction is ATP-dependent and takes place in two steps:

luciferin+ATP→luciferyl adenylate+PP$_i$

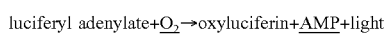

luciferyl adenylate+O$_2$→oxyluciferin+AMP+light

Target cells were plated at a concentration of $10^4$ cells per well in white 96-well plates (Nunc, Wiesbaden, Germany) and were cocultivated with varying numbers of TCR-transfected T cells in a final volume of 100 μl. 3 h later 50 μl of a D-Luciferin (BD Biosciences) containing reaction mix (Luciferin (1 μg/μl), HEPES-buffer (50 mM, pH), Adenosine 5'-triphosphatase (ATPase, 0.4 mU/μl, Sigma-Aldrich, St. Louis, USA) was added to the cells. By addition of ATPase to the reaction mix luminescence resulting from luciferase released from dead cells was diminished.

After a total incubation time of 4 h bioluminescence emitted by viable cells was measured using the Tecan Infinite 200 reader (Tecan, Crailsheim, Germany). Cell-killing activity was calculated in regard to luminescence values obtained after complete cell lysis induced by the addition of 2% Triton-X 100 and in relationship to luminescence emitted by target cells alone. Data output was in counts per second (CPS) and percent specific lysis was calculated as follows:

$$(1-(CPS_{exp}-CPS_{min})/(CPS_{max}-CPS_{min}))*100.$$

Maximum luminescence (maximum counts per second, CPSmax) was assessed after incubating target cells without effectors and minimal luminescences (CPSmin) was assessed after treatment of targets with detergent Triton-X-100 for complete lysis.

ELISPOT (Enzyme-Linked ImmunoSPOT Assay)

Microtiter plates (Millipore, Bedford, Mass., USA) were coated overnight at room temperature with an anti-IFNγ antibody 1-D1k (Mabtech, Stockholm, Sweden) and blocked with 2% human albumin (CSL Behring, Marburg, Germany). 2-5×$10^4$/well antigen presenting stimulator cells were plated in triplicates together with 0.3-3×$10^5$/well TCR-transfected CD4+ or CD8+ effector cells 24 h after electroporation. The plates were incubated overnight (37° C., 5% CO$_2$), washed with PBS 0.05% Tween 20, and incubated for 2 hours with the anti-IFNγ biotinylated mAB 7-B6-1 (Mabtech) at a final concentration of 1 μg/ml at 37° C. Avidin-bound horseradish peroxidase H (Vectastain Elite Kit; Vector Laboratories, Burlingame, USA) was added to the wells, incubated for 1 hour at room temperature and developed with 3-amino-9-ethyl carbazole (Sigma, Deisenhofen, Germany).

CFSE (Carboxyfluorescein Succinimidyl Ester) Proliferation Assay

CD8+ T cells were transfected with TCR or CAR RNA and labeled with 2.5 μM CFSE. Labeled T cells were washed and cocultured with RNA-transfected autologous monocytes or iDCs (E:T (effector cells:target (tumor) cells)=10:1). After 4 days of coculture cells were harvested and proliferation was analyzed by flow cytometry based on the progressive halving of CFSE fluorescence within daughter cells following cell divisions.

Retroviral Construct for Stable CAR Expression

For stable expression of the CLDN6-CAR or the CAR against an unrelated tumor antigen used as a negative control the retroviral SIN vector ES12.6 was used (FIG. 19).

Transduction of Human T Cells

For the mouse adoptive cell transfer (ACT) experiments, human T lymphocytes were enriched from PBMCs of healthy donors by removal of monocytes after 2 h of plastic adherence. T lymphocytes were cultured in X-Vivo (Lonza) medium supplemented with 5% human AB serum (Invitrogen), 100 U/ml IL2 (Proleukin S, Novartis), 20 ng/ml IL7 (Miltenyi), 10 ng/ml IL15 (Miltenyi) and stimulated with magnetic anti-CD3/anti-CD28 beads (Dynabeads; Invitrogen) at a 1:3 CD3 cell to bead ratio and transduced on days 3 and 4 post stimulation with retroviral supernatants. Cells were expanded in X-Vivo15 medium supplemented with 5% human AB serum, 300 U/ml IL2, 20 ng/ml IL7 and 10 ng/ml IL15. Incubation 37° C., 5% $CO_2$, 95% rH (FIG. 20).

Mouse Model for In-Vivo Validation of Antitumoral Activity

Xenograft tumors were established by subcutaneous injection of $1 \times 10^7$ OV90-SC12 human ovarian tumor cells into 8-14 week-old NOD.Cg-Prkdcscid Il2rgtm1Wjl/SzJ (NSG) mice (The Jackson Laboratory, Bar Harbor, Me.). After 4 days, mice were treated with a single intravenous injection of $1 \times 10^7$ of CAR transduced T cells (20-37% CAR positive). Tumor monitoring was performed weekly by volume measurements using caliper (FIG. 21(a)).

Example 2: Isolation of High-Affinity HLA-A*02-Restricted Murine TCRs Specific for Claudin-6

We validated the immunogenic potential of CLDN6 in A2/DR1 mice by repetitive intranodal immunization with CLDN6 encoding IVT-RNA and used spleen cells of these mice for isolation of CLDN6-specific T cells and subsequent cloning of the corresponding TCR genes (FIG. 5). Spleen cells of immunized mice were analyzed for the successful induction of CLDN6-specific T cells and their reactivity against predicted HLA-A*02 binding CLDN6 peptides ex-vivo by IFNγ-ELISPOT assay (FIG. 6).

Significant frequencies of CLDN6-specific T cells could be induced In all three mice by RNA immunization, whereas T cell reactivity was focused on two CLDN6 peptides predicted, that were with the best HLA-A*02 binding score (Cl6-A2-1 and Cl6-A2-2).

For isolation of CLDN6-specific T cells, spleen cells of immunized mice were restimulated in-vitro and sorted by flow cytometry based on the activation-induced upregulation of CD137 (FIG. 7).

CLDN6-specific CD8+ T cells could be retrieved from all three immunized A2/DR1 mice and a total of 11 CLDN6-specific TCRs were cloned from single-sorted murine T cells.

TCRs were subjected to immunological validation assays, which revealed that six CLDN6-TCRs recognized the HLA-A*0201-restricted epitope CLDN6-91-99 (Cl6-A2-1) and four CLDN6-TCRs were specific for CLDN6-14-22 (Cl6-A2-2), whereas both epitopes were previously identified by ex-vivo ELISPOT analysis (FIG. 8). One CLDN6-TCR ($TCR_{CD8}$-CLDN6#7) recognized the peptide CLDN6-7-15 (Cl6-A2-3).

Example 3: Comparative Testing of Murine TCRs Specific for CLDN6 91-99

Figure 9:
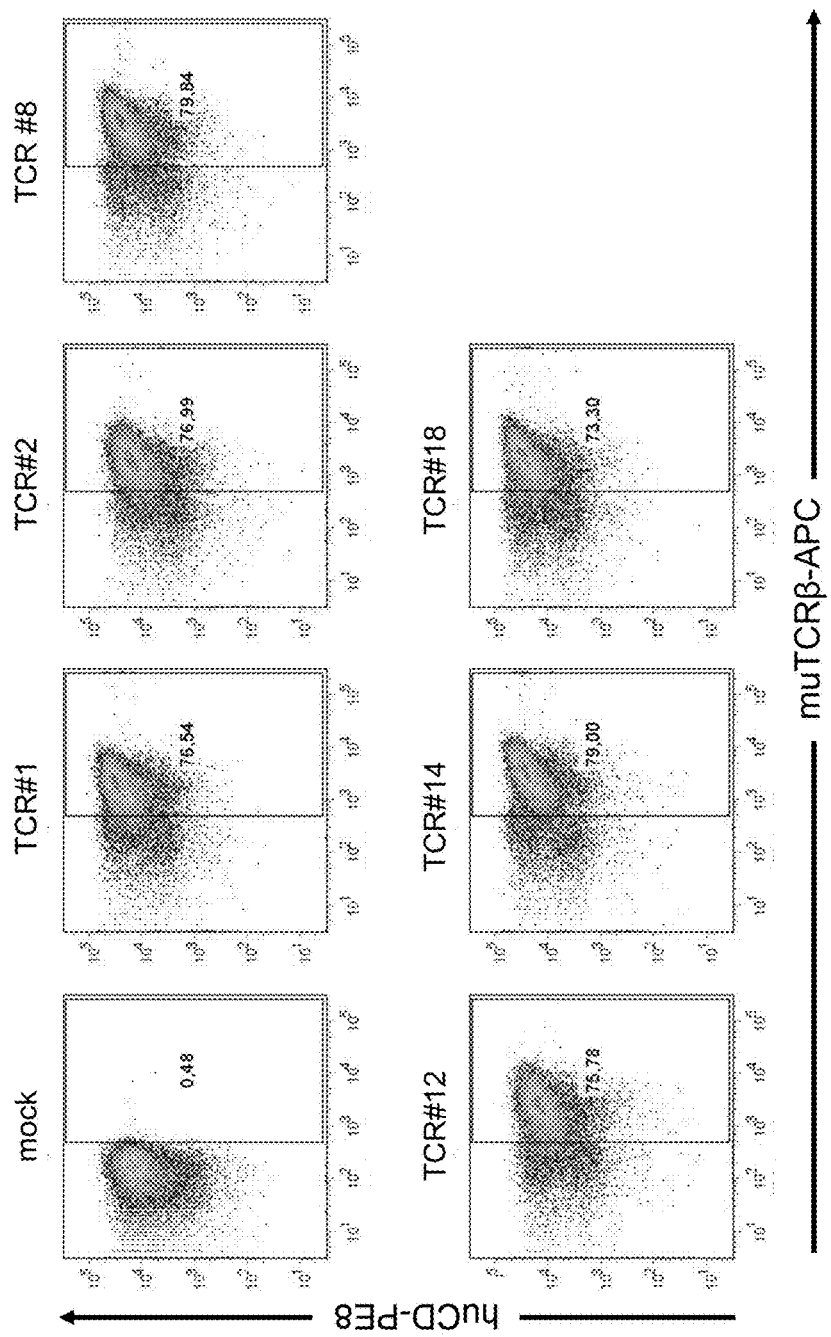

In total six murine TCRs were identified that all recognize the HLA-A*02-restricted epitope CLDN6-91-99. In order to confirm that this epitope is naturally processed and presented by endogenously CLDN6 expressing tumor cell lines and to evaluate the potential of the identified murine TCRs to mediate killing of such cells a luciferase-based cytotoxicity assay was performed. Human preactivated CD8+ T cells were transfected with TCR RNA and surface expression was analyzed by flow cytometry (FIG. 9). All murine TCRs were expressed on a high percentage of human CD8+ T cells after RNA transfer as indicated by staining with an fluorochrome-conjugated antibody specific for the constant domain of the murine TCR-β chain. TCR-transfected T cells were subjected to luciferase-based cytotoxicity assay together with the CLDN6-expressing tumor cell lines PA1 (teratoma) and NIH-Ovcar3 (ovarian carcinoma). The CLND6-negative breast cancer cell line MDA-MB-231 served as negative control. All TCRs mediated efficient lysis of CLDN6-expressing tumor cell lines ranging from 38-94% of PA1 and 29-76% of NIH-Ovcar3, while no lysis could be observed with untransfected T cells (FIG. 10). Most target cells were lysed when the $mTCR_{CD8}$-CLDN6 #1, #8 or #18 were used.

In order to analyze, if the murine TCRs can mediate specific proliferation of human T cells after coculture with autologous antigen-expressing target cells a CFSE proliferation assay was performed (FIG. 11). TCR-transfected CD8+ T cells were cocultured with autologous monocytes transfected with titrated amounts of CLDN6 RNA. All TCRs mediated specific proliferation indicated by the dilution of the CFSE proliferation dye after 4 days of coculture with CLDN6-RNA-transfected CD14+ cells, whereas again $mTCR_{CD8}$-CLDN6 #1, #8 or #18 showed the best results, especially when low amounts of CLDN6 RNA were transfected into the target cells. We decided to use $mTCR_{CD8}$-CLDN6 #18 as a gold standard for the lead structure selection together with CLDN6 targeting CAR formats.

Example 4: Generation and In-Vitro Validation of Claudin-6-Specific CARs

We evaluated two different CAR formats to specifically target CLDN6 on CLDN6 expressing target cells. One of them represents a novel format based on the linkage of the scFv with the constant domain of the murine TCRß chain and coexpression of the constant domain of the TCRα chain (CAR/Cα) (Voss R H et al., (2011) Molecular Therapy 19, supplement, S86) (FIG. 3). The second format represents a classical 2nd generation CAR (CAR-28ζ) that contains the signaling and costimulatory moieties of CD3ζ and CD28, respectively. A deletion of the lck binding moiety in the CD28 endodomain abrogates IL2 secretion upon CARengagement to prevent induction of regulatory T cells (Kofler D. M. et al., (2011) Molecular Therapy 19 (4), 760-767). A modification of the IgG1 Fc 'spacer' domain in the extracellular moiety of the CAR avoids 'off-target' activation and unintended initiation of an innate immune response (Hombach A. et al., (2010) Gene Therapy 17, 1206-1213).

As CARs provide HLA independent scFv-mediated antigen-binding they are functional in both CD4+ and CD8+ T cells. Therefore, we first analyzed the CAR surface expression on CD4+ and CD8+ T cells after transfection of CAR RNA into bulk PBMCs.

Both, the novel CAR/Cα and the classical 2nd generation CAR (CAR-28ζ) are expressed on the surface of human T cells after RNA transfer (FIG. 12). The CAR-28ζ was significantly better expressed on the surface of CD4+ and CD8+ T cells than the CAR/Cα. The latter one was transferred either by cotransfection of the CAR and the Cα chain or as a 2 A peptide-based bicistronic vector for simultaneous expression of CAR and Cα genes. Flow cytometry analysis demonstrated that the 2 A-based linkage of CAR and Cα results in decreased surface expression compared to coexpression of the two components. As a bicistronic vector would be used for clinical testing the linkage of the two CAR/Cα components has to be further improved.

To analyze the specific tumor cell lysis mediated by the different CLDN6-targeting receptor formats a luciferase-based cytotoxicity assay was performed. CAR- or TCR-transfected preactivated CD8+ T cells were cultured with CLDN6-positive or negative tumor cell lines at different effector-to-target ratios and the specific lysis was calculated after 4 h of coculture (FIG. 13). All CAR- and TCR-transfected T cells demonstrated significant specific lysis of CLDN6 expressing tumor cell lines compared to untransfected T cells.

A prerequisite for the proliferation and persistence of CAR-engineered T cells in the patient is the presence of antigen as demonstrated by promising clinical trial results of CD19-specific CARs in hematologic malignancies. In analogy to the expansion of endogenous T cells by RNA immunization, we wanted to analyze, if CAR T cells could also be expanded using RNA-vaccination of target cells to provide natural CLND6 for CAR T cell stimulation. An in vitro proliferation assay was performed using CAR-transfected CD8+ T cells together with CLDN6 or control RNA-transfected autologous iDCs (FIG. 14). The mTC R$_{CD8}$-CLDN6 #18 mediated best proliferation in response to CLDN6-transfected target cells (73%). The CLDN6-CAR-28ζ also resulted in a significant proportion of proliferating T cells (44%), while the CLDN6-CAR/Cα failed to induce proliferation probably due to the lack of CD28-mediated costimulation. As induction of proliferation is a prerequisite for successful antitumoral activity, we decided to use CAR-28ζ format for further lead structure selection.

Example 5: CLDN6-CAR-28ζ Lead Structure Selection for Preclinical and Clinical Testing The CLDN6-CAR-28ζ scFv fragment that is responsible for antigen recognition contains an unpaired cysteine. As such a free cysteine could result in misfolding of the CAR protein under certain circumstances or in unwanted interactions with other cyteines by the formation of disulfide bonds, we decided to eliminate this cysteine and exchanged it by a serine, a glycine or an alanine.

We than comparatively analyzed the resulting CLDN6-CAR-28ζ constructs regarding surface expression (FIG. 15, 16) and cytotoxicity (FIG. 17). Except of the glycine variant all mutated constructs demonstrated surface expression and lysis comparable to the wild-type variant.

In order to compare the affinity of the mutated CAR constructs their cytotoxic potential in response to autologous iDCs transfected with titrated amounts of CLDN6 RNA was analyzed. Even extremely little amounts of CLDN6 RNA (0.001 µg) resulted in significant lysis of target cells mediated by all CAR constructs. As the serine variant of the CLDN6-CAR-28ζ showed slightly better results regarding surface expression and cytotoxicity, we decided to use this variant for preclinical testing.

Example 6: In-Vivo Antitumoral Activity of the CLDN6-CAR

After having determined the antitumor activity against CLDN6 expressing tumor cell lines in-vitro the antitumor ability in tumor-bearing mice was determined. Therefore, the potency of CLDN6-CAR transduced human T cells was compared to T cells transduced with a control CAR against an unrelated tumor antigen and untransduced T cells in a xenograft model. A total of $1\times10^7$ cells of the human ovarian carcinoma cell line OV90-SC12 were injected subcutaneously in NSG mice. Four days after tumor engraftment the mice were treated with a single intravenous injection of $1\times10^7$ of CAR-transduced T cells. Tumor monitoring was performed weekly by volume measurements using caliper. Treatment of the mice with CLDN6-CAR-transduced T cells significantly slowed tumor growth compared to control groups treated with unrelated tumor antigen-CAR-transduced, untransduced T cells or a group not receiving T cells (FIGS. 21 (b) and (c)).

Example 7: In-Vitro Proliferation of CLDN6-CAR T Cells in Response to CLDN6-Expressing Target Cells In analogy to the expansion of endogenous T cells by RNA immunization, the stimulation and expansion of CAR T cells using RNA-vaccination of target cells to provide natural CLND6 was analyzed by in vitro proliferation assay. CD8$^+$ T cells were transfected with IVT-RNA encoding a CAR against CLDN6 or an unrelated tumor antigen as negative control, labeled with CFSE (carboxyfluorescein succinimidyl ester) and cocultured with CLDN6-transfected autologous iDCs for 4 days (FIG. 22). The CLDN6-CAR mediated proliferation of nearly all CD8$^+$ T cells in response to CLDN6-transfected iDC could be observed (95%), while only background proliferation (1.5%) could be observed for unrelated tumor antigen-CAR transfected T cells indicating that proliferation was not depending on the CAR backbone but was CLDN6-specific.

---

CLDN6-specific T cell epitopes

A2-1 (aa 91-99)
ALFGLLVYL

A2-2 (aa 14-22)
TLLGWVNGL

A2-3 (7-15)
QILGVVLTL

CLDN6-specific T cell receptors
TCR$_{CD8}$-mC16#1:
SEQ ID NO: 6; >Vα9N.3 J13 C
MLLALLSVLGIHFLLRDAQAQSVTQPDARVTVSEGASLQLRCKYSYFGT
PYLFWYVQYPRQGLQLLLKYYPGDPVVQGVNGFEAEFSKSNSSFHLRKA
SVHWSDWAVYFCAVSMSSGTYQRFGTGTKLQVVPNIQNPEPAVYQLKDP
RSQDSTLCLFTDFDSQINVPKTMESGTFITDKTVLDMKAMDSKSNGAIA
WSNQTSFTCQDIFKETNATYPSSDVPCDATLTEKSFETDMNLNFQNLSV
MGLRILLLKVAGFNLLMTLRLWSS SEQ ID NO: 7; >Vβ29 D1 J2.5 C2
MRVRLISAVVLCFLGTGLVDMKVIQMPRYLIKRMGENVLLECGQDMSHE
TMYWYRQDPGLGLQUYISYDVDSNSEGDIPKGYRVSRKKREHFSLILDS
AKTNQTSVYFCASSSQNQDTQYFGPGTRLLVLEDLRNVTPPKVSLFEPS
KAEIANKQKATLVCLARGFFPDHVELSWWVNGKEVHSGVSTDPQAYKES

CLDN6-specific T cell epitopes

NYSYCLSSRLRVSATFWHNPRNHFRCQVQFHGLSEEDKWPEGSPKPVTQ
NISAEAWGRADCGITSASYHQGVLSATILYEILLGKATLYAVLVSGLVL
MAMVKKNS

TCR$_{CD8}$-mC16#2:
SEQ ID NO: 8; >Vα6N.6 J23 C
MDSFPGFVAVILLILGRTHGDSVTQTEGGQVTVSESKSLIINCTYSATSI
GYPNLFWYVRYPGEGLQLLLKVITAGQKGSSRGFEATYNKEATSFHLQK
ASVQESDSAVYYCALNNQGKLIFGQGTKLSIKPNIQNPEPAVYQLKDPR
SQDSTLCLFTDFDSQINVPKTMESGTFITDKTVLDMKAMDSKSNGAIAW
SNQTSFTCQDIFKETNATYPSSDVPCDATLTEKSFETDMNLNFQNLSVM
GLRILLLKVAGFNLLMTLRLWSS

SEQ ID NO: 9; >Vβ13.2 D1 J2.4 C2
MGSRLFFVLSSLLCSKHMEAAVTQSPRNKVAVTGGKVTLSCNQTNNHNN
MYWYRQDTGHGLRLIHYSYGAGSTEKGDIPDGYKASRPSQENFSLILEL
ATPSQTSVYFCASGGDSQNTLYFGAGTRLSVEDLRNVTPPKVSLFEPS
KAEIANKQKATLVCLARGFFPDHVELSWWVNGKEVHSGVSTDPQAYKES
NYSYCLSSRLRVSATFWHNPRNHFRCQVQFHGLSEEDKWPEGSPKPVTQ
NISAEAWGRADCGITSASYHQGVLSATILYEILLGKATLYAVLVSGLVL
MAMVKKNS

TCR$_{CD8}$-mC16#3:
SEQ ID NO: 18; >Vα16N J6 C
MLILSLLGAAFGSICFAATSMAQKVTQTQTSISVVEKTTVTMDCVYETR
DSSYFLFWYKQTASGEIVFLIRQDSYKKENATVGHYSLNFQKPKSSIGL
IITATQIEDSAVYFCAMRDSSGGNYKPTFGKGTSLVVHPYIQNPEPAVY
QLKDPRSQDSTLCLFTDFDSQINVPKTMESGTFITDKTVLDMKAMDSKS
NGAIAWSNQTSFTCQDIFKETNATYPSSDVPCDATLTEKSFETDMNLNF
QNLSVMGLRILLLKVAGFNLLMTLRLWSS

SEQ ID NO: 19; >Vβ2 D2 J2.4 C2
MGSIFLSCLAVCLLVAGPVDPKIIQKPKYLVAVTGSEKILICEQYLGHN
AMYWYRQSAKKPLEFMFSYSYQKLMDNQTASSRFQPQSSKKNHLDLQIT
ALKPDDSATYFCASSQEDWGSQNTLYFGAGTRISVEDLRNVTPPKVSL
FEPSICAEIANKQKATINCLARGFFPDHVELSWWVNGKEVHSGVSTDPQ
AYKESNYSYCLSSRLRVSATFWHNPRNHFRCQVQFHGLSEEDKWPEGSP
KPVTQNISAEAWGRADCGITSASYHQGVLSATILYEILLGKATLYAVLV
SGLVLMAMVKKNS

TCR$_{CD8}$-mC16#7:
SEQ ID NO: 28; >Vα6N.7 or Vα6D.7_4 J26 C
MDSFPGFMTVMLLIFTRAHGDSVTQTEGQVALSEEDFLTIHCNYSASGY
PALFWYVQYPGEGPQFLFRASRDKEKGSSRGFEATYDKGTTSFHLRKAS
VQESDSAVYYCALGNNYAQGLTFGLGTRVSVFPYIQNPEPAVYQLKDPR
SQDSTLCLFTDFDSQINVPKTMESGTFITDKTVLDMKAMDSKSNGAIAW
SNQTSFTCQDIFKETNATYPSSDVPCDATLTEKSFETDMNLNFQNLSVM
GLRILLLKVAGFNLLMTLRLWSS

SEQ ID NO: 29; >Vβ13.3 D1 J1.4_02 C1
NIGSRLFTVVLILLCAKHMEAAVTQSPRSKVAVTGGKVTLSCHQTNNHD
YMYWYRQDTGHGLRLIHYSYVADSTEKGDIPDGYKASRPSQENFSLILE
LASLSQTAVYFCASSTGNERLFFGHGTKLSVEDLRNVTPPKVSLFEPS
KAEIANKQKATLVCLARGFFPDHVELSWWVNGKEVHSGVSTDPQAYKES
NYSYCLSSRLRVSATFWHNPRNHFRCQVQFHGLSEEDKWPEGSPKPVTQ
NISAEAWGRADCGITSASYQQGVLSATILYEILLGKATLYAVLVSTINV
MAMVKRKNS

TCR$_{CD8}$-mC16#8:
SEQ ID NO: 10; >Vα16N J13 C
MLILSLLGAAFGSICFATSMAQKVTQTQTSISVVEKTTVTMDCVYETRD
SSYFLFWYKQTASGEIVFLIRQDSYKKENATVGHYSLNFQKPKSSIGLI
ITATQIEDSAVYFCAMREAANSGTYQRFGTGTKLQVVPNIQNPEPAVYQ
LKDPRSQDSTLCLFTDFDSQINVPKTMESGTFITDKTVLDMKAMDSKSN
GAIAWSNQTSFTCQDIFKETNATYPSSDVPCDATLTEKSFETDMNLNFQ
NLSVMGLRILLLKVAGFNLLMTLRLWSS

SEQ ID NO: 11; >Vβ2 D1 J1.3 C1
MGSIFLSCLAVCLLVAGPVDPKIIQKPKYLVAVTGSEKILICEQYLGHN
AMYWYRQSAKKPLEFMFSYSYQKLMDNQTASSRFQPQSSKKNHLDLQIT
ALKPDDSATYFCASSQQNSGNTLYFGEGSRLIVVEDLRNVTPPKVSLFE
PSKAEIANKQKATLVCLARGFFPDHVELSWWVNGKEVHSGVSTDPQAYK
ESNYSYCLSSRLRVSATFWHNPRNHFRCQVQFHGLSEEDKWPEGSPKPV
TQNISAEAWGRADCGITSASYQQGVLSATILYEILLGKATLYAVLVSTL
VVMAMVKRKNS

TCR$_{CD8}$-mC16#10:
SEQ ID NO: 20; >Vα13D.4_03 J42 C
MKRLVCSLLGLLCTQVCWVKGQQVQQSPASLVLQEGENAELQCNFSSTA
TRLQWFYQRPGGSLVSLLYNPSGTKHTGRLTSTTVTKERRSSLHISSSQ
TTDSGTYFCAMSSNSGGSNAKLTFGKGTKLSVKSNIQNPEPAVYQLKDP
RSQDSTLCLFTDFDSQINVPKTMESGTFITDKTVLDMKAMDSKSNGAIA
WSNQTSFTCQDIFKETNATYPSSDVPCDATLTEKSFETDMNLNFQNLSV
MGLRILLLLKVAGFNLLMTLRLWSS

SEQ ID NO: 21; >Vβ4_02 D2 J2.7 C2
MGCRLLSCVAFCLLGIGPLETAVFQTPNYRVTRVGNEVSFNCEQTLDHN
TMYWYKQDSKKLLKIMFSYNNKQLIVNETVPRRFSPQSSDKAHLNRIK
SVELEDSAVYLCASSDWGDSYEQYFGPGTRLTVEDLRNVTPPKVSLFE
PSKAEIANKQKATLVCLARGFFPDHVELSWWVNGKEVHSGVSTDPQAYK
ESNYSYCLSSRLRVSATFWHNPRNHERCQVQFHGLSEEDKWPEGSPKPV
TQNISAEAWGRADCGITSASYHQGVLSATILYEILLGKATLYAVLVSGL
VLMAMVKKNS

TCR$_{CD8}$-mC16#12:
SEQ ID NO: 12; >Vα3.3 J50 C
MKTVTGPLFLCFWLQLNCVSRGEQVEQRPPHLSVREGDSAVITCTYTDP
NSYYFFWYKQEPGASLQLLMKVFSSTEINEGQGFTVLLNKKDKRLSLNL
TAAHPGDSAAYFCAVESSSFSKLVFGQGTSLSVVPNIQNPEPAVYQLKD
PRSQDSTLCLFTDFDSQINVPKTMESGTFITDKTVLDMKAMDSKSNGAI
AWSNQTSFTCQDIFKETNATYPSSDVPCDATLTEKSFETDMNLNFQNLS
VMGLRILLLLKVAGFNLLMTLRLWSS

SEQ ID NO: 13; >Vβ26 D2 J2.5 C2
MATRLLCYTVLCLLGARILNSKVIQTPRYLVKGQGQKAKMRCIPEKGHP
VVFWYQQNKNNEFKFLINFQNQEVLQQIDMTEKRFSAECPSNSPCSLEI
QSSEAGDSALYLCASSLTGGAQDTQYFGPGTRLLVLEDLRNVTPPKVSL
FEPSKAEIANKQKATLVCLARGFFPDHVELSWWVNGKEVHSGVSTDPQA
YKESNYSYCLSSRLRVSATFWHNPRNHFRCQVQFHGLSEEDKWPEGSPK
PVTQNISAEAWGRADCGITSASYHQGVLSATILYEILLGKATLYAVLVS
GLVLMAMVKKNS

TCR$_{CD8}$-mC16#13:
SEQ ID NO: 22; >Vα16N J22 C
MLILSLLGAAFGSICFAATSMAQKVTQTQTSISVVEKTTVTMDCVYETR
DSSYFLFWYKQTASGEIVFLIRQDSYKKENATVGHYSLNFQKPKSSIGL
IITATQIEDSAVYFCAMRVASSGSWQLIFGSGTQLTVMPDIQNPEPAVY
QLKDPRSQDSTLCLFTDFDSQINVPKTMESGTFITDKTVLDMKAMDSKS
NGAIAWSNQTSFTCQDIFKETNATYPSSDVPCDATLTEKSFETDMNLNF
QNLSVMGLRILLLKVAGFNLLMTLRLWSS

SEQ ID NO: 23; >Vβ2 D1 J2.1 C2
MGSIFLSCLAVCLLVAGPVDPKIIQKPKYLVAVTGSEKILICEQYLGHN
AMYWYRQSAKKPLEFMFSYSYQKLMDNQTASSRFQPQSSKKNHLDLQIT
ALKPDDSATYFCASSQGDNNYAEQFFGPGTRLTVEDLRNVTPPKVSLFE
EPSKAEIANKQKATLVCLARGFFPDHVELSWWVNGKEVHSGVSTDPQAY
KESNYSYCLSSRLRVSATFWHNPRNHFRCQVQFHGLSEEDKWPEGSPKP
VTQNISAEAWGRADCGITSASYHQGVLSATILYEILLGKATLYAVLVSG
LVLMAMVKKNS

TCR$_{CD8}$-mC16#14:
SEQ ID NO: 14;> Vα4N.4 or Vα4D.4_03 J6 C
MQRNLVAVLGILWVQICWVRGDQVEQSPSALSLHEGTGSALRCNFTTTM
RAVQWFRKNSRGSLINLFYLASGTKENGRLKSAFDSKERYSTLHIRDAQ
LEDSGTYFCAAEGGGNYKPTFGKGTSLVVHPYIQNPEPAVYQLKDPRSQ
DSTLCLFTDFDSQINVPKTMESGTFITDKTVLDMKAMDSKSNGAIAWSN
QTSFTCQDIFKETNATYPSSDVPCDATLTEKSFETDMNLNFQNLSVMGL
RILLLKVAGFNLLMTLRLWSS

SEQ ID NO: 15; >Vβ31 D1 J1.1 C1
MLYSLLAFLLGMFLGVSAQTIHQWPVAEIKAVGSPLSLGCTIKGKSSPN
LYWYWQATGGTLQQLFYSITVGQVSNVQLNLSASRPKDDQFILSTEKL
LLSHSGFYLCAWSSPPINTEVFFGKQTRLTVVEDLRNVTPPKVSLFEPSK
AEIANKQKATLVCLARGFFPDHVELSWWVNGKEVHSGVSTDPQAYKESN
YSYCLSSRLRVSATFWHNPRINTHFRCQVQFHGLSEEDKWPEGSPKPVT
QNISAEAWGRADCGITSASYQQGVLSATILYEILLGKATLYAVLVSTLV
VMAMVKRKNS

TCR$_{CD8}$-mC16#15:
SEQ ID NO: 24; >Vα3.1 J39 C
MKTVTGPLLLCFWLQLNCVSRGEQVEQRPPHLSVREGDSAIICTYTDS
ATAYFSWYKQEAGAGLQLLMSVLSNVDRKEEQGLTVLLNKKDKRLSLNL
TAAHPGDSAVYFCATNAGAKLTFGGGTRLTVRPDIQNPEPAVYQLKDPR
SQDSTLCLFTDFDSQINVPKTMESGTFITDKTVLDMKAMDSKSNGAIAW

CLDN6-specific T cell epitopes

SNQTSFTCQDIFKETNATYPSSDVPCDATLTEKSFETDMNLNFQNLSVM
GLRILLLKVAGFNLLMTLRLWSS

SEQ ID NO: 25; >Vβ4 D2 J2.7 C2
MGCRLLSCVAFCLLGIGPLETAVFQTPNYHVTQVGNEVSFNCKQTLGHD
TMYWYKQDSKKLLKIMFSYNNKQLIVNETVPRRFSPQSSDKAHLNLRIK
SVEPEDSAVYLCASSLYWGDSYEQYFGPGTRLTVLEDLRNVTPPKVSLF
EPSKAEIANKQKATLVCLARGFFPDHVELSWWVNGKEVHSGVSTDPQAY
KESNYSYCLSSRLRVSATFWHNPRNHFRCQVQFHGLSEEDKWPEGSPKP
VTQNISAEAWGRADCGITSASYHQGVLSATILYEILLGKATLYAVLVSG
LVLMAMVKKKNS

TCR$_{CD8}$-mC16#17:
SEQ ID NO: 26; >Vα14.3 or Vα14D.3/DV8_08 J22 C
MDKNLTASFLLLGLHLAGVSGQQEKRDQQQVRQSPQSLTVWEGETAILN
CSYENSAFDYFPWYQQFPGEGPALLISILSVSDKKEDGRFTIFFNKREK
KLSLHIADSQPGDSATYFCAASLSSGSWQLIFGSGTQLTVMPDIQNPEP
AVYQLKDPRSQDSTLCLFTDFDSQINVPKTMESGTFITDKTVLDMKAMD
SKSNGAIAWSNQTSFTCQDIFKETNATYPSSDVPCDATLTEKSFETDMN
LNFQNLSVMGLRILLLKVAGFNLLMTLRLWSS

SEQ ID NO: 27; >Vβ3 D2 J2.7 C2
MDIWLLGWIIFSFLEAGHTGPKVLQIPSHQIIDMGQMVTLNCDPVSNHL
YFYWYKQILGQQMEFLVNFYNGKVMEKSKLFKDQFSVERPDGSYFTLKI

CLDN6-specific T cell epitopes

QPTALEDSAVYFCASSLVGGYEQYFGPGTRLTVLEDLRNVTPPKVSLFE
PSKAEIANKQKATLVCLARGFFPDHVELSWWVNGKEVHSGVSTDPQAYK
ESNYSYCLSSRLRVSATFWHNPRNHFRCQVQFHGLSEEDKWPEGSPKPV
TQNISAEAWGRADCGITSASYHQGVLSATILYEILLGKATLYAVLVSGL
VLMAMVKKKNS

TCR$_{CD8}$-mC16#18:
SEQ ID NO; 16; >Vα6D.6_02 J4 C
MDSSPGINAVILLILGRTHGDSVTQTEGPVTVSESESLIINCTYSATSI
AYPNLFWYVRYPGEGLQLLLKVITAGQKGSSRGFEATYNKETTSFHLQK
ASVQESDSAVYYCALGETGSFNKLTFGAGTRLAVCPYIQNPEPAVYQLK
DPRSQDSTLCLFTDFDSQINVPKTMESGTFITDKTVLDMKAMDSKSNGA
IAWSNQTSFTCQDIFKETNATYPSSDVPCDATLTEKSFETDMNLNFQNL
SVMGLRILLLKVAGFNLLMTLRLWSS

SEQ ID NO: 17; >Vβ26 D1 J2.7 C2
MATRLLCYTVLCLLGARILNSKVIQTPRYLVKGQGQKAKMRCIPEKGHP
VVFWYQQNKNNEFKFLINFQNQEVLQQIDMTEKRFSAECPSNSPCSLEI
QSSEAGDSALYLCASSLGIYEQYFGPGTRLTVLEDLRNVTPPKVSLFEP
SKAEIANKQKATLVCLARGFFPDHVELSWWVNGKEVHSGVSTDPQAYKE
SNYSYCLSSRLRVSATFWHNPRNHFRCQVQFHGLSEEDKWPEGSPKPVT
QNISAEAWGRADCGITSASYHQGVLSATILYEILLGKATLYAVLVSGLV
LMAMVKKKNS

The invention claimed is:

1. A method of treating a cancer disease comprising administering a pharmaceutical composition to a patient having claudin-6 (CLDN6)-expressing cancer cells, the pharmaceutical composition comprising a nucleic acid having a nucleic acid sequence encoding an artificial T cell receptor which specifically binds CLDN6 and comprises an amino acid sequence at least 95% identical to SEQ ID NO: 46, wherein the binding domain for CLDN6 comprises the complementarity-determining regions CDR1, CDR2, and CDR3 of the heavy chain variable region according to SEQ ID NO: 32 and the complementarity-determining regions CDR1, CDR2, and CDR3 of the light chain variable region according to SEQ ID NO: 39.

2. A method for inducing an immune response in a subject having claudin-6 (CLDN6)-expressing cancer cells, the method comprising administering to the subject a pharmaceutical composition comprising a nucleic acid having a nucleic acid sequence encoding an artificial T cell receptor which specifically binds CLDN6 and comprises an amino acid sequence at least 95% identical to SEQ ID NO: 46, wherein the binding domain for CLDN6 comprises the complementarity-determining regions CDR1, CDR2, and CDR3 of the heavy chain variable region according to SEQ ID NO: 32 and the complementarity-determining regions CDR1, CDR2, and CDR3 of the light chain variable region according to SEQ ID NO: 39.

3. A method of killing cancer cells in a subject having CLDN6-expressing cancer cells, comprising the step of providing to the subject a therapeutically effective amount of a nucleic acid having a nucleic acid sequence encoding an artificial T cell receptor which specifically binds CLDN6 and comprises an amino acid sequence at least 95% identical to SEQ ID NO: 46, wherein the binding domain for CLDN6 comprises the complementarity-determining regions CDR1, CDR2, and CDR3 of the heavy chain variable region according to SEQ ID NO: 32 and the complementarity-determining regions CDR1, CDR2, and CDR3 of the light chain variable region according to SEQ ID NO: 39.

4. A method of killing cancer cells in a subject having CLDN6-expressing cancer cells, comprising the step of providing to the subject a therapeutically effective amount of a cell comprising a nucleic acid having a nucleic acid sequence encoding an artificial T cell receptor which specifically binds CLDN6 and comprises an amino acid sequence at least 95% identical to SEQ ID NO: 46, wherein the binding domain for CLDN6 comprises the complementarity-determining regions CDR1, CDR2, and CDR3 of the heavy chain variable region according to SEQ ID NO: 32 and the complementarity-determining regions CDR1, CDR2, and CDR3 of the light chain variable region according to SEQ ID NO: 39.

5. A method of killing cancer cells in a subject having CLDN6-expressing cancer cells, comprising the step of providing to the subject a therapeutically effective amount of an immunoreactive cell obtainable from a method comprising the step of transducing a T cell with a nucleic acid having a nucleic acid sequence encoding an artificial T cell receptor which specifically binds CLDN6 and comprises an amino acid sequence at least 95% identical to SEQ ID NO: 46, wherein the binding domain for CLDN6 comprises the complementarity-determining regions CDR1, CDR2, and CDR3 of the heavy chain variable region according to SEQ ID NO: 32 and the complementarity-determining regions CDR1, CDR2, and CDR3 of the light chain variable region according to SEQ ID NO: 39.

6. A method of killing cancer cells in a subject having CLDN6-expressing cancer cells, comprising the step of providing to the subject a therapeutically effective amount of an artificial T cell receptor which specifically binds CLDN6 and comprises an amino acid sequence at least 95% identical to SEQ ID NO: 46, wherein the binding domain for CLDN6 comprises the complementarity-determining regions CDR1, CDR2, and CDR3 of the heavy chain variable region according to SEQ ID NO: 32 and the complementarity-determining regions CDR1, CDR2, and CDR3 of the light chain variable region according to SEQ ID NO: 39.

7. The method of claim 1, 2, 3, 4, 5 or 6, wherein the artificial T cell receptor comprises a binding domain, said binding domain comprises a heavy chain variable region (VH) and a light chain variable region (VL), and wherein the VH comprises an amino acid sequence of SEQ ID NO: 32 and the VL comprises an amino acid sequence of SEQ ID NO: 39.

8. The method of claim 1, 2, 3, 4, 5 or 6, wherein the artificial T cell receptor comprises an amino acid sequence of SEQ ID NO: 46.

\* \* \* \* \*